(12) United States Patent
Dean et al.

(10) Patent No.: US 9,672,302 B2
(45) Date of Patent: *Jun. 6, 2017

(54) PRODUCING A THREE-DIMENSIONAL MODEL OF AN IMPLANT

(71) Applicant: OSTEOPLASTICS, LLC, Shaker Heights, OH (US)

(72) Inventors: Howard David Dean, Columbus, OH (US); Krishnamoorthy Subramanyan, Palatine, IL (US); Alexandros T. Moullas, Salonika (GR); Robert A. Ratcheson, Hamilton, MT (US)

(73) Assignee: Osteoplastics, LLC, Shaker Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/075,498

(22) Filed: Mar. 21, 2016

(65) Prior Publication Data

US 2016/0203241 A1    Jul. 14, 2016

Related U.S. Application Data

(63) Continuation of application No. 14/277,275, filed on May 14, 2014, which is a continuation of application (Continued)

(51) Int. Cl.
*A61B 5/00* (2006.01)
*G06F 17/50* (2006.01)
(Continued)

(52) U.S. Cl.
CPC .............. *G06F 17/50* (2013.01); *A61B 5/103* (2013.01); *A61B 5/1075* (2013.01); *A61B 34/10* (2016.02);

(Continued)

(58) Field of Classification Search
CPC ....... A61B 5/055; A61B 5/1075; A61B 6/032; G06T 15/08; G06T 17/00;

(Continued)

(56) References Cited

U.S. PATENT DOCUMENTS 4,436,684 A    3/1984 White
4,704,686 A    11/1987 Aldinger
(Continued)

FOREIGN PATENT DOCUMENTS

DE    39 33 459 A1    4/1991
DE    196 42 247 C1   1/1998
(Continued)

OTHER PUBLICATIONS

International Search Report of corresponding International Application No. PCT/US2000/022053, dated Feb. 26, 2001.

(Continued)

*Primary Examiner* — Amanda Lauritzen Moher
(74) *Attorney, Agent, or Firm* — Mueting, Raasch & Gebhardt, P.A.

(57) ABSTRACT

Determining a shape of a medical device to be implanted into a subject produces an image including a defective portion and a non-defective portion of a surface of a tissue of interest included in the subject. The tissue of interest is segmented within the image. A template, representing a normative shape of an external anatomical surface of the tissue of interest, is superimposed to span the defective portion. An external shape of an implant, is determined as a function of respective shapes of the defective portion as seen in the template, for repairing the defective portion.

9 Claims, 56 Drawing Sheets

Related U.S. Application Data

No. 12/720,518, filed on Mar. 9, 2010, now Pat. No. 8,781,557, which is a continuation-in-part of application No. 10/089,467, filed as application No. PCT/US00/22053 on Aug. 11, 2000, now abandoned, said application No. 12/720,518 is a continuation-in-part of application No. 10/129,308, filed as application No. PCT/US00/41821 on Nov. 3, 2000, now Pat. No. 7,702,380.

(60) Provisional application No. 61/148,393, filed on Aug. 11, 1999, provisional application No. 60/148,277, filed on Aug. 11, 1999, provisional application No. 61/148,275, filed on Aug. 11, 1999, provisional application No. 60/163,323, filed on Nov. 3, 1999.

(51) Int. Cl.
| | |
|---|---|
| A61B 5/107 | (2006.01) |
| A61B 34/10 | (2016.01) |
| G05B 19/4099 | (2006.01) |
| G06T 19/00 | (2011.01) |
| A61B 5/103 | (2006.01) |
| A61F 2/30 | (2006.01) |
| G06T 15/00 | (2011.01) |
| A61F 2/28 | (2006.01) |

(52) U.S. Cl.
CPC ........ *A61F 2/2875* (2013.01); *A61F 2/30942* (2013.01); *G05B 19/4099* (2013.01); *G06T 15/00* (2013.01); *G06T 19/00* (2013.01); *A61B 2034/108* (2016.02); *G05B 2219/49023* (2013.01); *G06T 2210/41* (2013.01); *Y10S 128/923* (2013.01); *Y10S 623/911* (2013.01)

(58) Field of Classification Search
CPC . G06T 2207/20084; G06T 2207/30008; G06T 2207/30052; G06T 2210/41; G06T 7/0012; G06T 7/0051; G06T 7/0081
See application file for complete search history.

(56) References Cited

U.S. PATENT DOCUMENTS

| | | | |
|---|---|---|---|
| 4,936,862 A | 6/1990 | Walker et al. | |
| 4,976,737 A | 12/1990 | Leake | |
| 5,121,333 A | 6/1992 | Riley et al. | |
| 5,156,777 A | 10/1992 | Kaye | |
| 5,274,565 A | 12/1993 | Reuben | |
| 5,357,429 A | 10/1994 | Levy | |
| 5,360,446 A | 11/1994 | Kennedy | |
| 5,370,692 A * | 12/1994 | Fink | B29C 41/36 128/898 |
| 5,522,019 A | 5/1996 | Bala et al. | |
| 5,554,190 A | 9/1996 | Draenert | |
| 5,647,018 A | 7/1997 | Benjamin | |
| 5,682,886 A | 11/1997 | Delp et al. | |
| 5,735,277 A | 4/1998 | Schuster | |
| 5,740,802 A | 4/1998 | Nafis et al. | |
| 5,741,215 A | 4/1998 | D'Urso | |
| 5,752,962 A | 5/1998 | D'Urso | |
| 5,768,134 A | 6/1998 | Swaelens et al. | |
| 5,798,924 A | 8/1998 | Eufinger et al. | |
| 5,813,984 A | 9/1998 | Haaga et al. | |
| 5,824,085 A | 10/1998 | Sahay et al. | |
| 5,871,018 A | 2/1999 | Delp et al. | |
| 6,049,743 A | 4/2000 | Baba | |
| 6,126,690 A | 10/2000 | Ateshian et al. | |
| 6,146,390 A | 11/2000 | Hellibrun et al. | |
| 6,205,411 B1 | 3/2001 | DiGioia, III et al. | |
| 6,206,927 B1 | 3/2001 | Fell et al. | |
| 6,254,639 B1 | 7/2001 | Peckitt | |
| 6,327,491 B1 | 12/2001 | Franklin et al. | |
| 6,415,171 B1 | 7/2002 | Gueziec et al. | |
| 6,424,332 B1 | 7/2002 | Powell | |
| 6,445,943 B1 | 9/2002 | Ferre et al. | |
| 6,459,948 B1 | 10/2002 | Ateshian et al. | |
| 6,470,207 B1 | 10/2002 | Simon et al. | |
| 6,923,817 B2 | 8/2005 | Carson et al. | |
| 6,937,696 B1 | 8/2005 | Mostafavi | |
| 7,702,380 B1 | 4/2010 | Dean | |
| 7,747,305 B2 | 6/2010 | Dean et al. | |
| 2001/0027271 A1 | 10/2001 | Franck et al. | |
| 2002/0059049 A1 | 5/2002 | Bradbury et al. | |
| 2003/0216669 A1 | 11/2003 | Lang et al. | |
| 2004/0167390 A1 | 8/2004 | Alexander et al. | |
| 2007/0233272 A1 | 10/2007 | Boyce et al. | |
| 2008/0015433 A1 | 1/2008 | Alexander et al. | |
| 2012/0010711 A1 | 1/2012 | Antonyshyn et al. | |
| 2012/0072185 A1 | 3/2012 | Lang et al. | |
| 2016/0196651 A1* | 7/2016 | Dean | G06T 7/0012 345/419 |

FOREIGN PATENT DOCUMENTS

| | | |
|---|---|---|
| EP | 0 255 797 A1 | 2/1988 |
| GB | 2 324 470 A | 10/1998 |
| RU | 2 073 490 C1 | 2/1997 |
| WO | WO 92/00045 A1 | 1/1992 |

OTHER PUBLICATIONS

International Preliminary Examination Report of International Application No. PCT/US2000/041821, dated Sep. 23, 2002.
International Search Report of International Application No. PCT/US2000/041821 , dated Jul. 13, 2001.
Amari, "Topological Organization of Nerve Fields" *Bulletin of Mathematical Biology*, 1980; 42:339-64.
Badouel, "An Efficient Ray-Polygon Intersection" *Graphics Gems*, Academic Press, San Diego. 1990; 390-393.
Barry et al. "A recursive evaluation algorithm for a class of Catmull-Rom Splines" *SIGGRAPH Comput. Graphics*, 1988; 22(4):199-204.
Barsky et al. "Determining a set of B-spline control vertices to generate an interpolating surface" *Comput. Graph. Image Process*, 1980; 14(3):203-226.
Bartels, "Splines in Interactive Computer Graphics" *Numerical Analysis: Lecture Notes in Mathematics*, 1984; 1066:1-29.
Besl et al., "Three-Dimensional Object Recognition" *ACM Computing Surveys*, 1985; 17(1):75-145.
Besl et al., "A method for registration of 3-D Shapes" *IEEE Transactions on Pattern Analysis and Machine Intelligence*, 1992; 14(2):239-256.
"Biomedical applications: Computer-Assisted Paleoanthropology Tutorial", University of Zurich, Germany, Retrieved from: http:\\www.ifi.unizh.ch/staff/zolli/cap/biomedical.htm, Retrieved Date: Nov. 1, 2000 (5 pages total).
Bookstein, "Principal Warps: Thin-Plate Splines and the Decomposition of Deformations" *IEEE T Pattern Anal. and Machine Intell.*, 1989; 11(6):567-585.
Bookstein et al., "A proposal for the apprehension of curving craniofacial form in three dimensions" in *Craniofacial Morphogenesis and Dysmorphogenesis*, Vig and Burdi (Eds.), Center for Human Growth and Development, University of Michigan Press, Ann Arbor, MI, 1988; 127-140.
Bricault et al., "From Volume Medical Images to Quadratic Surface Patches" *Computer Vision and Image Understanding*, Jul. 1997; 67(1):24-38.
Buckley et al., "Three-dimensional magnetic resonance-based morphometrics and ventricular dysmorphology in schizophrenia" *Biological Psychiatry*, Jan. 1, 1999; 45(1):62-67.
Carr et al., "Surface interpolation with radial basis functions for medical imaging" *IEEE T. Med. Imaging.*, Feb. 1997; 16(1):96-107.
Catmull et al., "A Class of Local Interpolating Splines" *Computer Aided Geometric Design*, Barnhill and Reisenfeld (Eds.), Academic Press, New York, 1974; 317-326.

(56) References Cited

OTHER PUBLICATIONS

Christiansen et al., "Conversion of Complex Contour Line Definitions into Polygonal Element Mosaics" *ACM SIGGRAPH Computer Graphics Newsletter*, 1978; 12(3):187-192.
Coons, "Surface patches and B-spline curves" *Computer Aided Geometric Design*, Barnhill and Riesenfeld (Eds.) Academic Press, New York, 1974; 1-16.
Cutting et al., "A Spline-based approach for averaging three-dimensional curves and surfaces" *SPIE Mathematical Methods in Medical Imaging II*, 1993; 2035, 29-44. Accessed online at <http://proceedings.spedigitallibrary.org/> on May 26, 2015.
Cutting et al., "A three-dimensional smooth surface analysis of untreated Crouzon's syndrome in the adult" *J. Craniofac. Surg.* 1995; 6(6):444-53.
De Boor, "On Calculating with B-Splines" *J. Approx. Theory*, 1978; 6:50-62.
Dean, "The Middle Pleistocene Homo erectus / Homo sapiens transition: New Evidence From Space Curve Statistics" Ph.D Thesis, City University of New York, 1993; 261 pages.
Dean et al., "Homology: Selection of landmarks, space curves and pseudolandmarks in the creation of deformable templates" in *Proceedings in Current Issues in Statistical Shape Analysis*, Mardia and Gill (Eds.), Univ. of Leeds Press, Leeds, England. 1995; 203-206.
Dean et al., "Three dimensional MR-based morphometric comparison of schizophrenic and normal cerebral ventricles" *Visualization in Biomedical Computing, Lecture Notes in Computer Science*, 1996; 1131, 363-372.
Dean et al., "3D Soft Tissue Face Bolton Standards" Proceedings Conference on Computer Integrated Surgery, International Society for Computer Assisted Surgery, Linz, Austria, Sep. 1-5, 1997; Wiley, New York. Abstract Only.
Dean et al., "Comparison of Traditional Brain Segmentation Tools with 3D Self-Organizing Maps" *Informational Processing in Medical Imaging, Lecture Notes in Computer Science*, 1997; 1230:393-8.
Dean et al., "Accuracy and precision of 3D cephalometric landmarks from biorthogonal plain film X-rays" SPIE Medical Imaging 98, 1998; 3335:50-58.
Dean et al., "Average African-American 3D-CT Skull Images: The Potential Clinical Importance of Ethnicity and Sex," *J. Craniofac. Surg.*, 1998; 9(4):348-359.
Dean et al., "Validation of Object-induced MR Distortion Correction for Frameless Stereotactic Neurosurgery" *IEEE Trans. Medical Imaging*, Oct. 1998; 17(5):810-16.
Dean et al., "Deformable Templates for Preoperative Computer-Aided Design and Fabrication of Large Cranial Implants" *International Congress Series*, Jun. 2003; 1256:710-5.
Declerck et al. "Automatic Retrieval of Anatomical Structures in 3D Medical Images" *Computer Vision, Virtual Reality and Robotics in Medicine, Lecture notes in Computer Science*, 1995; 905:153-162.
Desbrun et al., "Implicit Fairing of Irregular Meshes Using Diffusion and Curvature Flow" *SIGGRAPH '99, Proceedings of the 26th annual conference on Computer Graphics and Interactive Techniques*, 1999; 317-324.
Doi et al., "An Efficient Method of Triangulating Equi-Valued Surfaces by Using Tetrahedral Cells" *IEICE Transactions on Information and Systems*, 1991; E74-D(1): 214-224.
Eck et al., "Automatic Reconstruction of B-Spline Surfaces of Arbitrary Topological Type" *In: Proceedings of SIGGRAPH*, 1996; 325-334.
Eppley et al., "Computer-generated patient models for reconstruction of cranial and facial deformities" *J. Craniofac. Surg.* 1998; 9(6):548-56.
Eufinger et al., "Reconstruction of craniofacial bone defects with individual alloplastic implants based on CAD/CAM-manipulated CT-data" *J. Crania Maxillo-facial Surgery*, Jun. 1995 23(3): 175-81.
Eufinger et al., "Reconstruction of an extreme frontal and frontobasal defect by microvascular tissue transfer and a prefabricated titanium implant" *Plast. Reconsrt. Surg.* 1999; 104(1):198-203.
Eufinger et al., "The use of individual surgical templates in computer-assisted surgery" *Int. Congress Series*, 2001; 1230:230-4.
Falcao et al., "User-Steered Image Segmentation Paradigms: Live Wire and Live Lane" *Graphical Models and Image Proc.* Jul. 1998; 60(4):233-60.
Forsey et al., "Hierarchical B-spline refinement," *Comput. Graphics (Proc. ACM Siggraph)*, 22 (1988) 205-212.
Goodall, "Procrustes methods in the statistical analysis of shape" *Journal of the Royal Statistical Society*. Series B, 53:285-339. (1991).
Gottschalk et al., "OBB Tree: a hierarchical structure for rapid interference detection," *Comput. Graphics (Proc. ACM Siggraph)*, Proc. 23rd Annual Conf. (1996) 171-180.
Gueziec et al., "The Wrapper algorithm for surface extraction in volumetric data" in *Symposium on Applications of Computer Vision in Medical Image Processing*, pp. 227-231. 1991.
Gueziec et al., "The wrapper: A surface optimization algorithm that preserves highly curved areas," in *Proc. Visualization in Biomedical Computing'94, SPJE* 2359-58, 631-642, SPIE, Bellingham, Washington 1994.
Gueziec et al., "Smoothing and matching of 3-D space curves" *Inter. Journal of Computer Vision*, 1994; 12:79-104.
Gueziec et al., "Exploiting triangulated surface extraction using tetrahedral decomposition" *IEEE T Vis. Comput. Graphics*, 1995; 1:328-342.
Gueziec, "Surface representation with deformable splines: Using decoupled variables" *IEEE Computational Science and Engineering*, 1995; 2:69-80.
Heissler et al., "Custom-made cast titanium implants produced with CAD/CAM for the reconstruction of cranium defects" *Int. J. Oral Maxillofac. Surg.*, 1998; 27:334-8.
Hu, "Visual pattern Recognition by moment invariants" *IEEE Trans. Information Theory*, 1962; IT-8:179-87.
Hubbard, "Constructive solid geometry for triangulated polyhedra", *Technical Report CS-90-07*, 1-21, Dept. of Computer Science, Brown University, Providence, RI, 1990.
Jain et al., "Object matching using deformable templates," *IEEE Pattern Analysis and Machine Intelligence*, 1996; 18:267-77.
Joffe et al., "Validation of computer-assisted manufacture of titanium plates for cranioplasty," *Int. J. Oral. Maxillofac. Surg.*, 1999; 28:309-13.
Jolly et al., "Vehicle segmentation and classification using deformable templates," *IEEE Pattern Analysis and Machine Intelligence*, 1996; 18(3):293-308.
Kalvin et al., "Constructing topologically connected surfaces for the comprehensive analysis of 3-D medical structures" *SPIE Medical Imaging 91*, 1991; 1445: 247-58. Accessed online at <http://proceedings.spedigitallibrary.org/> on May 26, 2015.
Kass et al., "Snakes: Active contour models" *Int. J. Comput. Vis.*, 1988; 321-331.
Kendall, "Shape manifolds, procrustean metrics and complex projective spaces" *Bulletin of the London Mathematical Society*, 1994; 16:81-121.
Kent et al., "Ridge curves and shape analysis" Technical Report, Stat 96/05, Dept. of Statistics, University of Leeds, UK. (Also in Proc. of British Machine Vision Conference) 1996.
Kirkpatrick et al., "Optimization by simulated annealing" *Science*, 1983; 220:671-80.
Kohonen "Self-Organized Formation of Topologically Correct Feature Maps" *Biological Cybernetics*, 1982; 43:59-69.
Kohonen "Physiological interpretation of the self-organizing map algorithm," *Neural Networks*, 1993; 6(1):895-905.
Kohonen et al., "Engineering applications of the self-organizing map" *Proceedings of the IEEE*, 1996; 84:1358-84.
Linney et al., "Three-dimensional visualization of data on human anatomy: Diagnosis and surgical planning," *J. Audiov. Media Med.*, 1993; 16:4-10.
Lorensen et al. "Marching cubes: a high resolution 3d surface construction algorithm" *Comput. Graphics. (Proc. ACM Siggraph)*, 1987; 21(4):163-169.

(56) References Cited

OTHER PUBLICATIONS

Macaraeg, "Three Dimensional Changes in the Soft Tissue Face of Ten Bolton Study Males as seen in Bi-Orthogonal Cephalograms and 3D CT Images" Department of Anatomy, Case Western Reserve University. May 1999.
Maes et al., "Multimodality image registration by maximization of mutual information" *IEEE T. Med. Imaging*, 1997; 16:187-198.
Marr et al., "Theory of Edge Detection" *Proc. R. Soc. London, Ser B, Biol. Sci.*, 1980; 207(1167):187-217.
Marsh et al., A Discussion of "Computer-designed prostheses for orbitocranial reconstruction" by Tosh, Ellis and Steward, *Plast. Reconstr. Surg.*, 1988; 323-4.
"Mapping Human Anatomy from MRI Data for Improved Product Development," Medical Device a* Diagnostic Industry Magazine, Mar. 1, 1997, available at http://www.mddionline.com/article/mapping-human-anatomy-mri-data-improved-product-development. 5 pgs.
Metropolis et al., "Equation of State Calculations by Fast Computing Machines" *The Journal of Chemical Physics*, 1953; 21(6):1087-1092.
Mitchell et al., "The Discrete Geodesic Problem" *Siam J. Comput.* 1987; vol. 16(4):647-668.
Mohler et al., "Custom implants for reconstruction of craniofacial defects" *Arch. Surg.*, 1976; 111:452-455.
Moller, "A Fast Triangle-Triangle Intersection Test" *J. Graphics Tools*, 1997; 2:25-30.
Monga et al., "Using Partial Derivatives of 3D Images to Extract Typical Surface Features" *Computer Vision and Image Understanding*, Mar. 1995; 61(2):171-189.
Mortenson et al. "Interactive Segmentation with Intelligent Scissors" *Graph. Models and Image Proc.*, 1998; 60:349-84.
Noordmans H.J. et al., "Localisation of subdural EEG electrode bundles in an interactive volume rendering framework" Medical Image Computing and Computer-Assisted Intervention—Miccai '99, Second International Conference, Proceedings (Lecture Notes in Computer Science vol. 1679),—Cambridge, UK, Sep. 19-22, 1999, pp. 734-741 ,XP001 0113911999, Berlin, Germany, Springer-Verlag, Germany, ISBN: 3-540-66503-X, abstract (previously cited in U.S. Appl. No. 10/129,308, filed Sep. 3, 2002).
Ezquerra, N. et al, "Knowledge Guided Segmentation of 3D Imagery," *CVGIP: Graph. Models and Image Proc.*, vol. 58, pp. 510-523, 1996.
Ozkan, M. et al., "Neural-Network-Based Segmentation of Multi-Model Medical Images: A Comparative and Prospective Study", *IEEE Trans. Medical Imaging*, vol. 12, pp. 534-544, 1993.
Park et al., *Biomater. Sci. Polym. Ed* 1998; 9:89-110.
Rajan, D. S. et al., "CAD Model Slicing and Surface Smoothing for Building Rapid Prototyping Parts," *Industrial Electronics, Control and Instrumentation, 1996, Proc. 1996 IEEE IECON $22^{nd}$ Int. Conf.*, 1496-1501, Part 3, Taipei, Taiwan, 1996.
Richolt, J.A. et al., "Impingement Simulation of the Hip in SCFE Using 3D Models," *Comput. Aided. Surg.*, 4 (1999) 144-151.
Rhodes et al., "An Application of Computer Graphics and Networks to Anatomic Model and Prothesis Manufacturing" IEEE CG&A 7(2): pp. 12-25, Feb. 1987.
Rohlf, F.J. "Rotational Fit (Procrustes) Methods" in *Proc. of the Michigan Morphometrics Workshop*, Univ. Michigan Mus. Zoo, Ann Arbor, MI, 1989.
Rohlf, F.J., (1993) Relative Warp Analysis and an Example of its Application to Mosquito Wings. *Contributions to Morphometrics*, 131-159, Museum of Natural History, Madrid.
Rolf, A., "Seeded Region Growing," *IEEE Patt. Anal. Mach. Intell.*, vol. 16, pp. 641-647, 1994.
Sadjadi, F.A. et al., "Three Dimensional Moment Invariants," IEEE Patt. Anal. Mach. Intell., vol. 2, pp. 127-136, 1980.
Sailer, H.F. et al., "The Value of Stereolithographic Models for Preoperative Diagnosis of Craniofacial Deformities and Planning of Surgical Corrections," *Int. J. Oral. Maxillofac.* Surg. 27 (1988) 327-333.
Segal M. et al. "Partitioning Polyhedral Objects Into Noninterseecting Parts," *IEEE Comput.* Graphics, 8 (1988) 63-67.
Shoemake, K., "Linear Form Curves," in *Graphics Gems V*, Academic Press Inc., San Diego, CA (1995) 210-223.
Subramanyan et al., "A procedure to average 3D anatomical structures" Medical Image Analysis, 4 pages 317-334, 2000, 18 pages total.
Subramanyan, K., "Scanned Bi-Orthogonal Radio-Graphs as a Source for 3D Cephalometric Data," *SPIE Medical Imaging 96*, vol. 2710-73, pp. 717-724, 1996.
Subsol, G. et al., "A General Scheme for Automatically Build 3D Morphometric Anatomical Atlases: Application to a Skull Atlas," in Second Annual International Symposium on Medical Robotics and Computer Assisted Surgery, pp. 226-233, Wiley-Liss, New York, 1995.
Tampieri, F., "Newell's Method for Computing the Plane Equation of a Polygon," in *Graphics Gems III*, Academic Press, Inc., San Diego, CA (1992) 231-232.
Taubin, G., "A Signal Processing Approach to Fair Surface Design," *Comput. Graphics, (Proc. ACM Siggraph)*, (1995), 351-358.
Tek, H., et al., "Volumetric Segmentation of Medical Images by 3-D Bubbles," *Computer Vision and Image Understanding*, vol. 65, pp. 246-258, 1997.
Terzopoulos, D. et al., "Dynamic 3D Models with Local and Global Deformations: Deformable Superquadrics," *IEEE Pattern Analysis and Machine Intelligence*, vol. 13, pp. 703-724, 1991.
Thirion et al., "The Marching Lines Algorithm: new results and proofs" Technical Report No. 1881-1, *Institut National de Recherche en Informatique et en Automatique*, Apr. 1993; 32 pages.
Thirion, J.P., "Extremal Points: Definition and Application to 3D Image Registration", in *IEEE Conf. on Comput. Vis. and Pattern Recogn.*, 587-592, Seattle, WA 1994.
Thirion, J.P. et al., "The 3D Marching Lines Algorithm," Graphical Models and Image Processing, vol. 58, pp. 503-509, 1996.
Udupa, J.K., "Multidimensional Digital Boundaries," *CVGIP: Graph, Models and Image Proc.*, vol. 56, pp. 311-323, 1994.
Vanputten et al., *J. Prosthet. Dent.* 1992, 68:103-108.
Vollmer, J. et al., "Improved Laplacian Smoothing of Noisy Surface Meshes," *Comput. Graphics Forum*, 18 (1999) 131-138.
Wehmoller, M. et al., "CAD by Processing of Computed Tomography Data and CAM of Individually Designed Prostheses," *Int. J. Oral Maxillofac. Surg.*, 24 (1995) 90-97.
Wells W.et al.. "Video Registration Using Fiducials for Surgical Enhanced Reality" Proceedings of the Annual International Conference of the Engineering in Medicine and Biology Society. US, New York, IEEE, val. CONF. 15, Oct. 28, 1993 (Oct. 28, 1993), pp. 24-25, XP000431483 (previously cited in U.S. Appl. No. 10/129,308, filed Sep. 3, 2002).
Wernecke, J. et al., *The Inventor Mentor: Programming Object-Oriented 3D Graphics with Open Inventor*™, Release 2, Addison-Wesley Publishing Company, New York, 1994.
Zachow S. et al., "Optimized arrangement of osseointegrated implants: a surgical planning system for the fixation of facial prostheses" Proceedings of 13th International Symposium on Computer Assisted Radiology and Surgery (Cars '99), Paris, France, Jun. 23-26, 1999, pp. 942-946, XP001011401 1999, Amsterdam, Netherlands, Elsevier Science, Netherlands ISBN: 0-444-50290-4 (previously cited in U.S. Appl. No. 10/129,308, filed Sep. 3, 2002).
Eufinger, "Individual augmentation of the atrophic mandible based on CAD/CAM-manipulated computed tomography data—in vitro results" Int J Oral Maxillofac Surg, 1994; 23:399-402.

\* cited by examiner

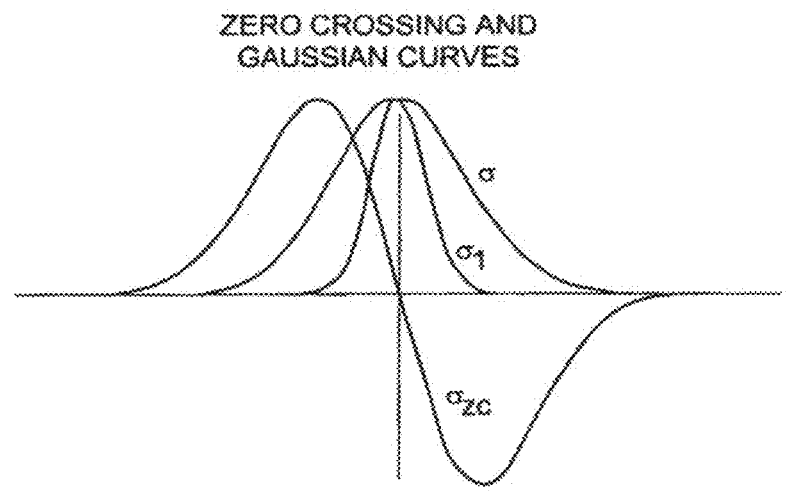
FIG. 6
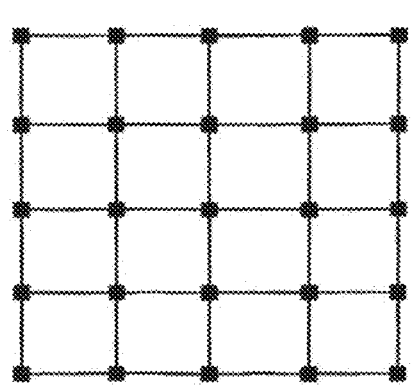 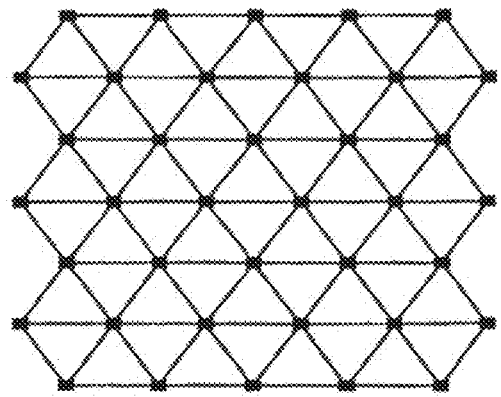
FIG. 7

A. Surface rendering of voxels in C.

B. Surface rendering of voxels in D.

C. Back projected soft tissue face voxels.

D. Back projected skull voxels.

E. Final processor ordered map.

UNORGANIZED MAP PRIOR
TO INPUT EVENT ORDERING

FINAL ORDERED MAP OF PROCESSORS
AND ASSOCIATED FEATURE CLUSTERS

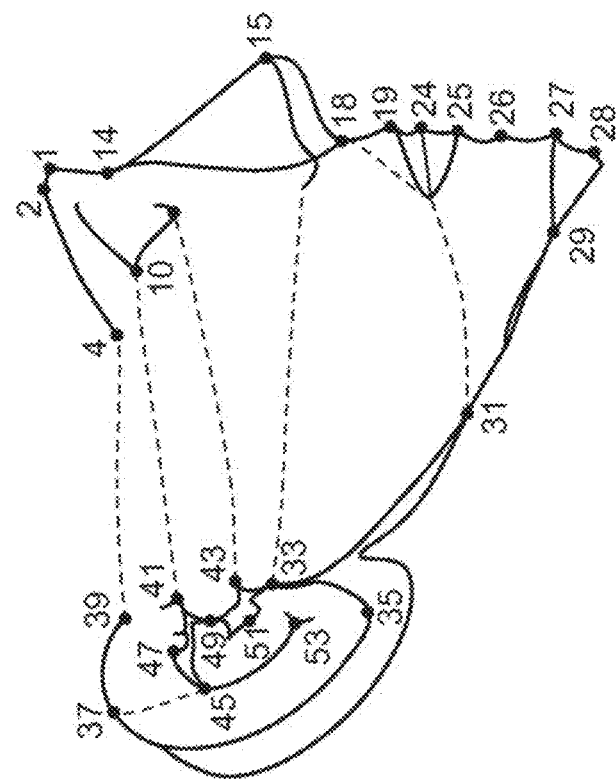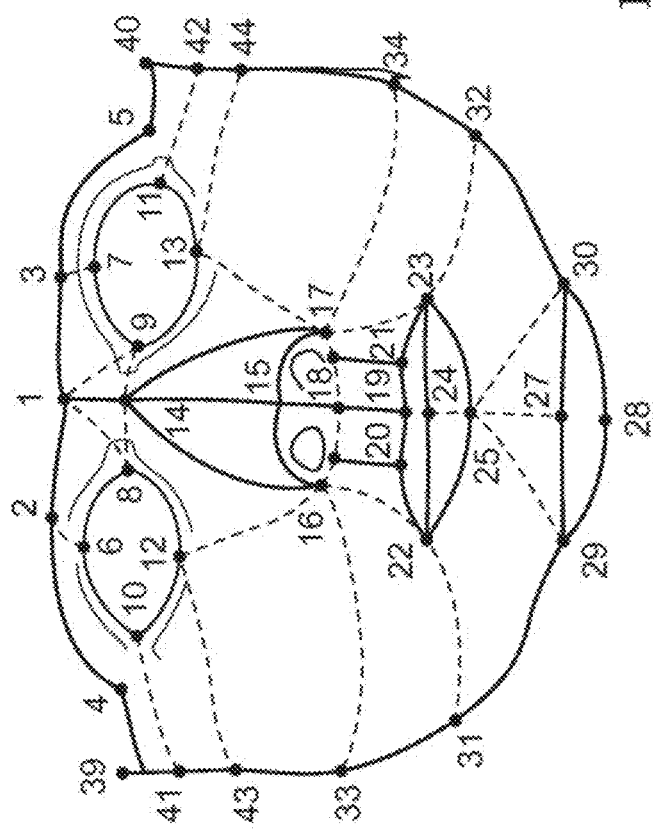
FIG. 19A

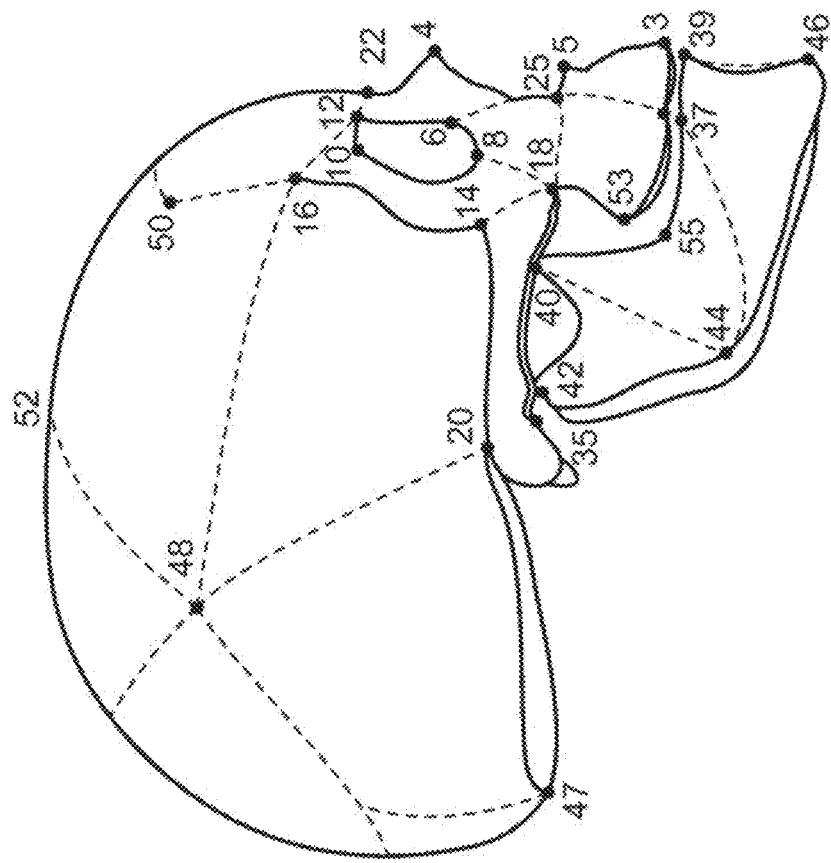
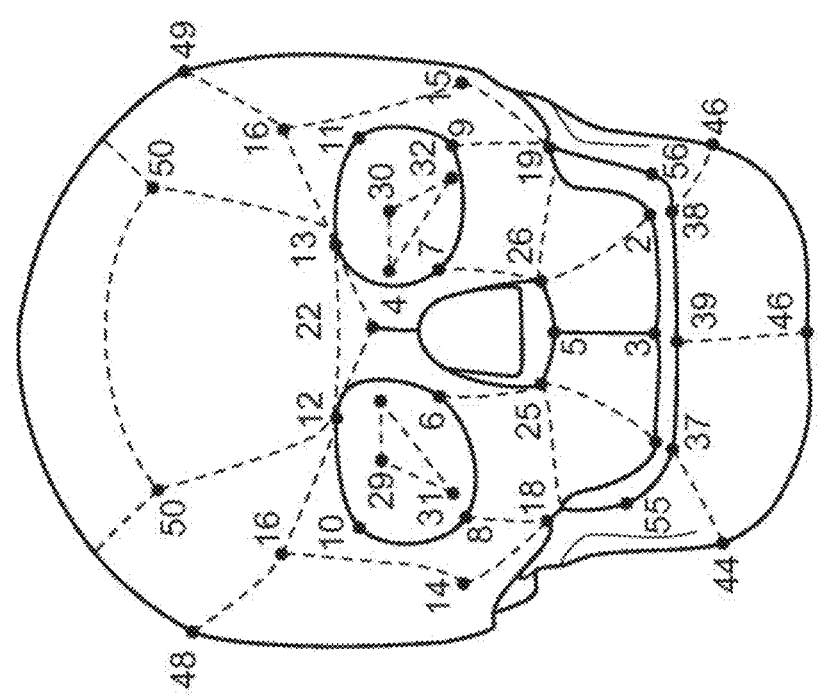
FIG. 19B

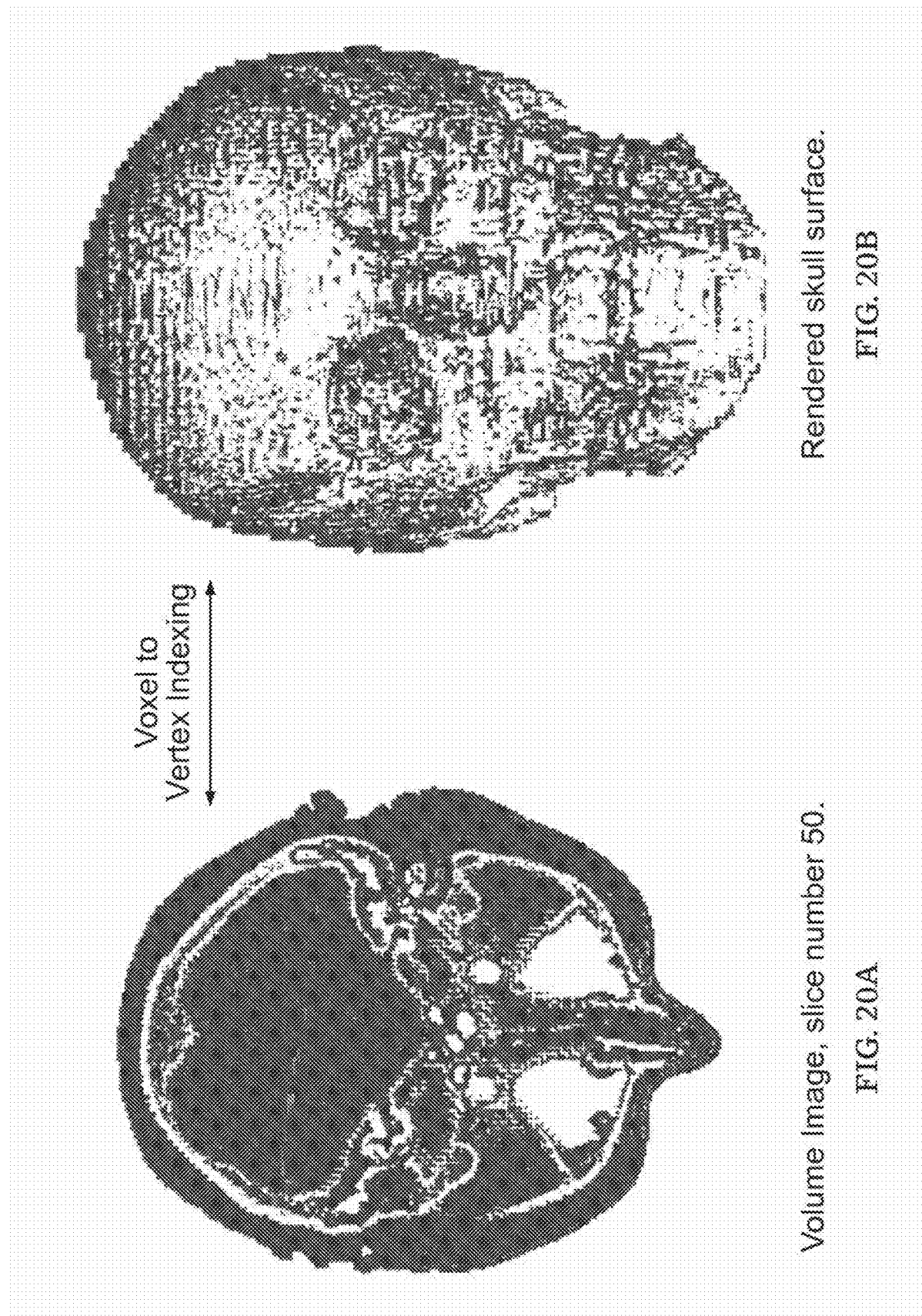

WIREFRAME TEMPLATE AND GRAPHICAL MANIFOLD.

TEMPLATE WARPED TO TYPE II LANDMARK POSITIONS.

Differential Characteristics of Surfaces.

$k_1, k_2$ - Principal Curvatures

Ridge Curve Definition.

PLANE CONTAINING TILING CURVE END POINTS A AND B
(TYPE II LANDMARKS) AND CENTER OF MASS

THREE DIMENSIONAL VIEW OF DEVIATION MEASURE, $d_m$.

Cross Section of Skull Surface Showing Search Planes.

Search plane sweeps on image surface.

Cost function determines which candidate control point is on the final ridge curve.

Initial Ridge Curve Control Point Search.

Fitted Ridge Curve Control Points.

Initial Tiling Curve Control Point Search.

Fitted Tiling Curve Control Points.

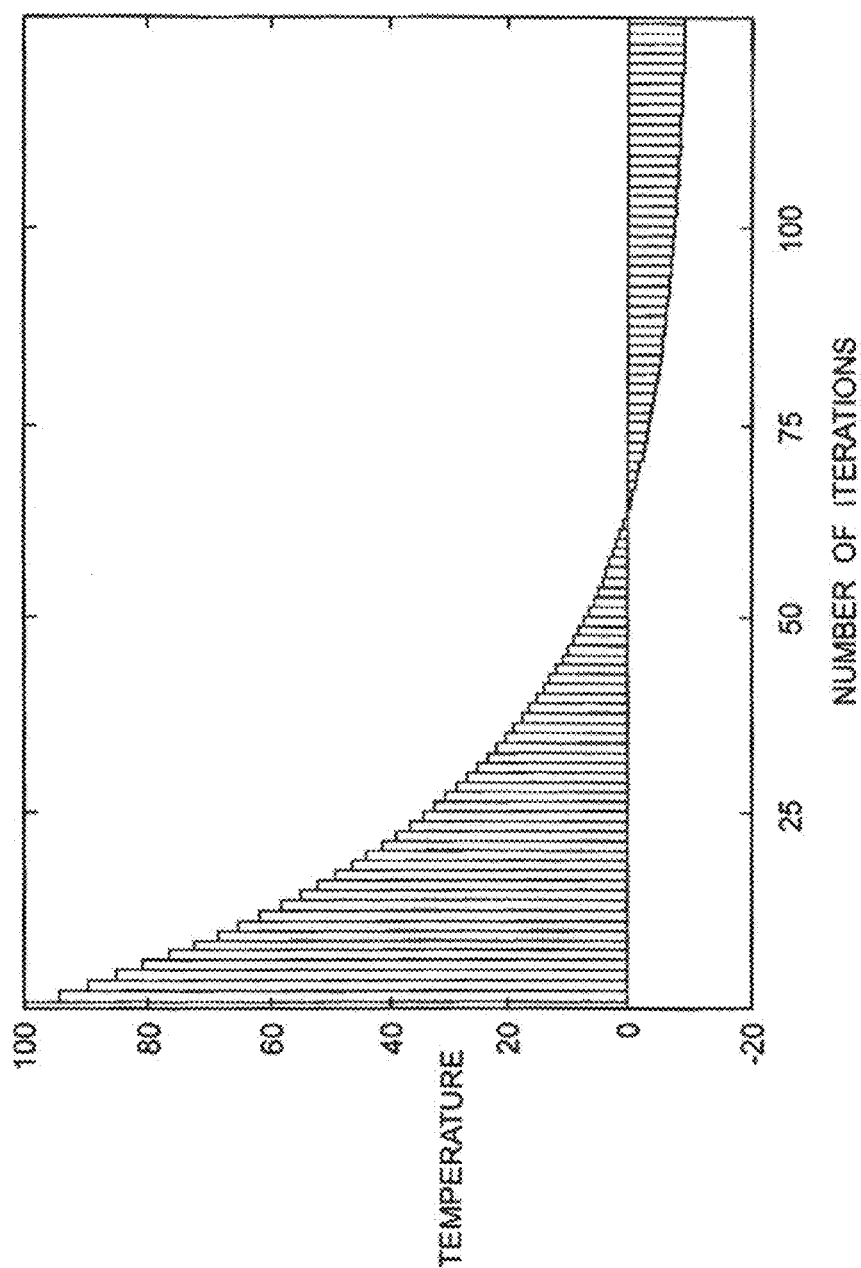

CURVE POINT NORMALS

SURFACE TILE POINT NORMALS

FITTED TEMPLATE SURFACE

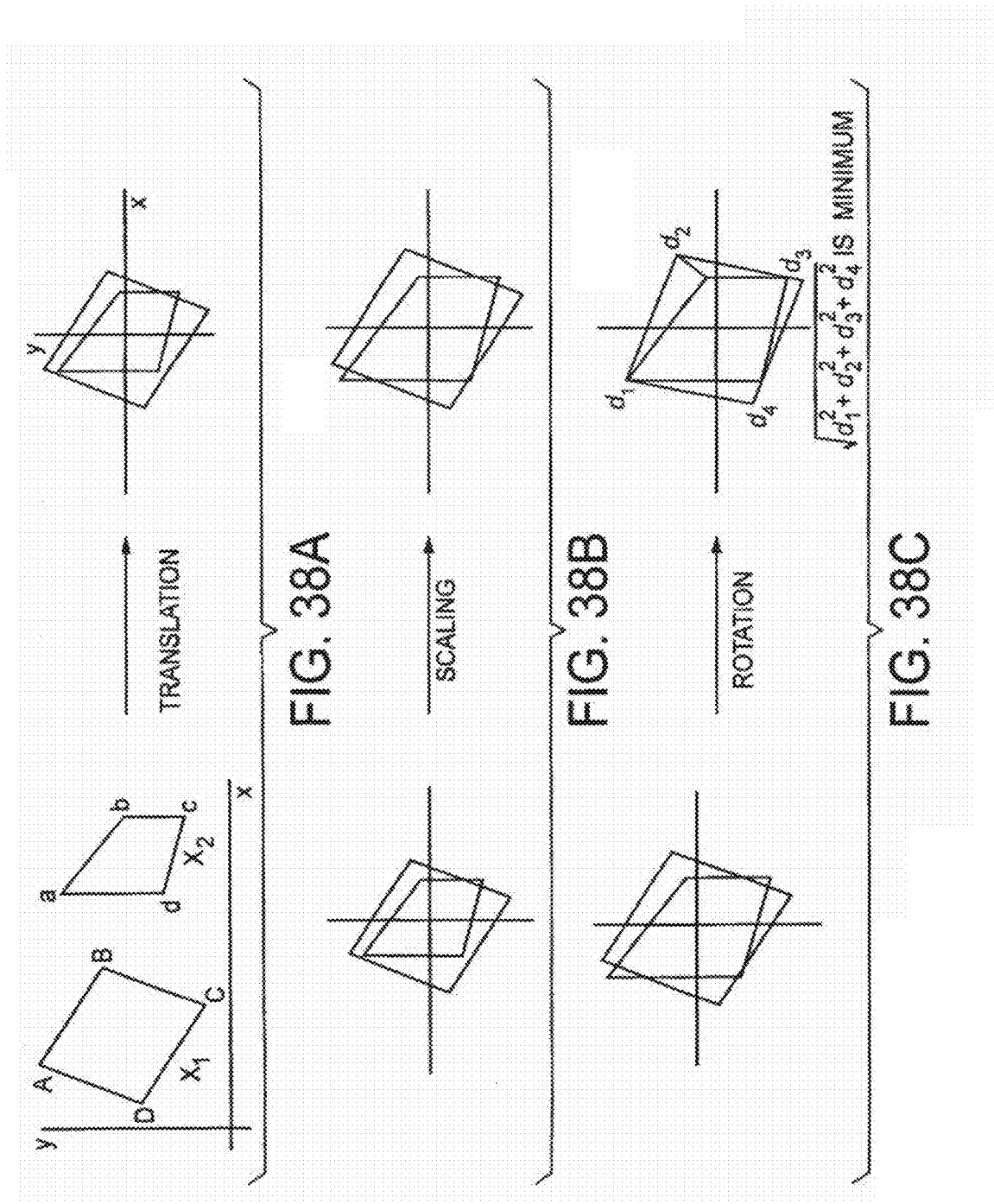

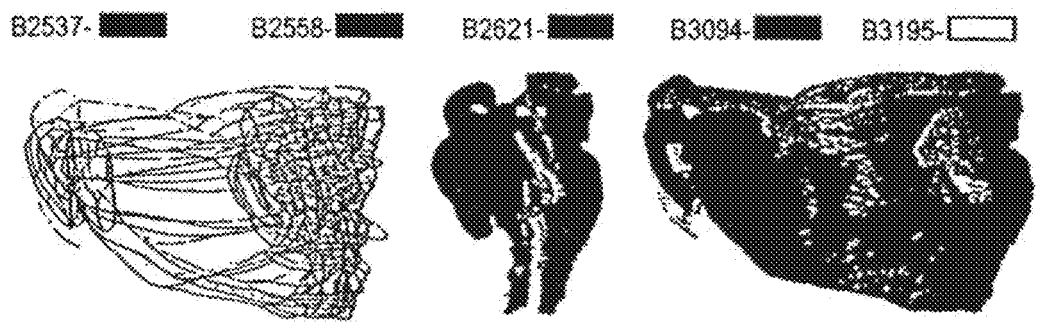
FIVE PATIENT FACE SURFACES (SPACE CURVES AND SURFACE TILES) IN THEIR ORIGINAL CT SPACE.
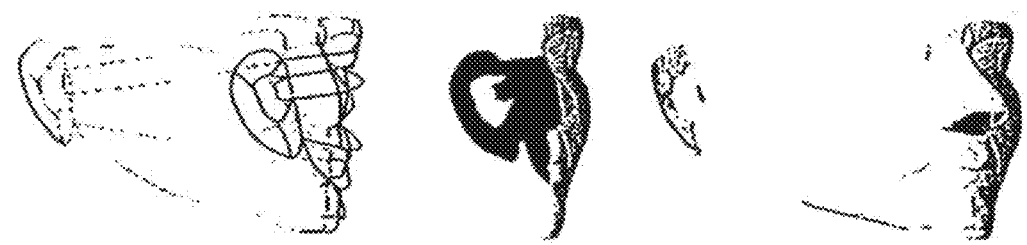
AVERAGE FACE SURFACE
(AVERAGE SPACE CURVES AND TRIANGULATED SURFACE TILES).
FIG. 40A

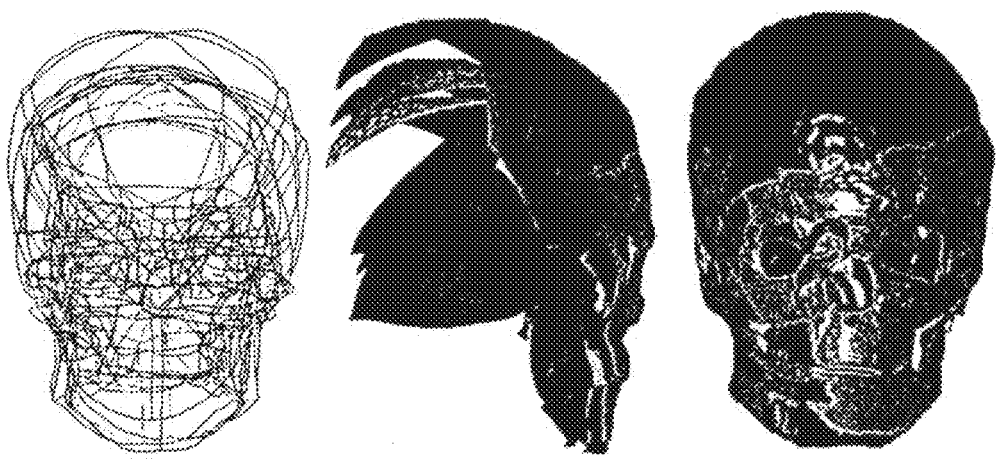
Five Patient Surfaces (Space curves and Surface Tiles) in their original CT space.
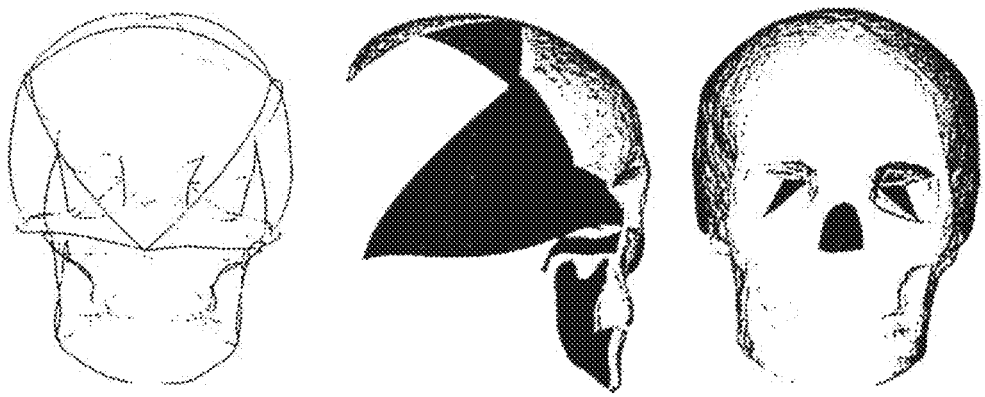
Average Boney Skull Surface (Average Space Curves and Trinagulated Surface Tiles).
FIG. 40B SSA soft tissue face sample members and average.
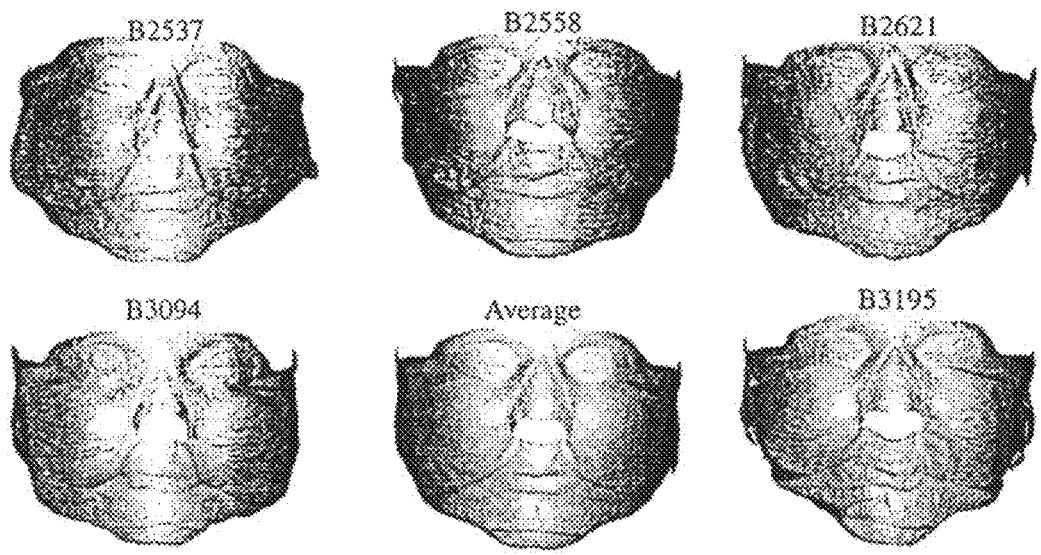
NYU soft tissue face sample members and average.
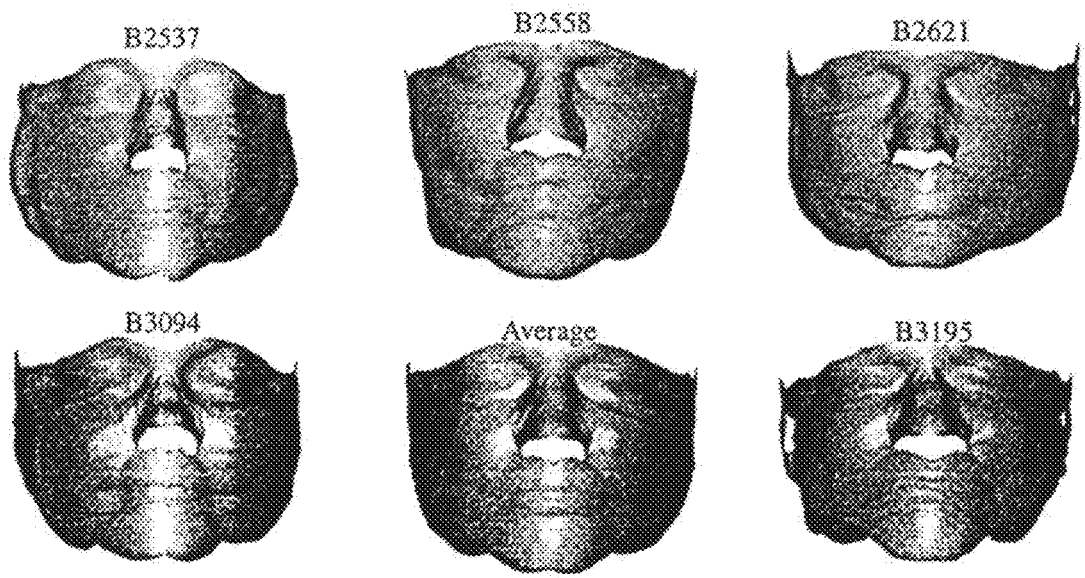
FIG. 41A

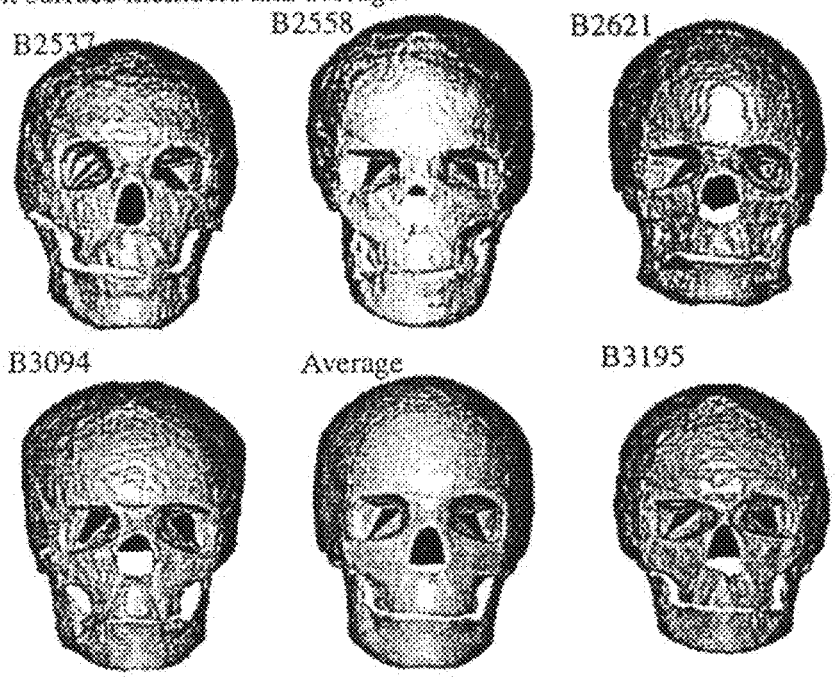
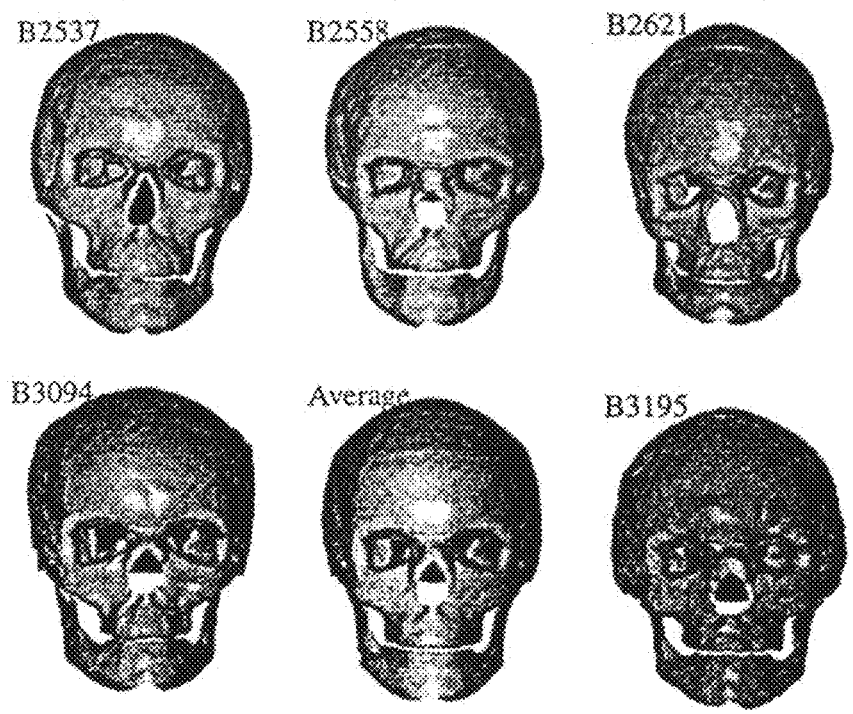
FIG. 41B

SSA Average Surfaces.
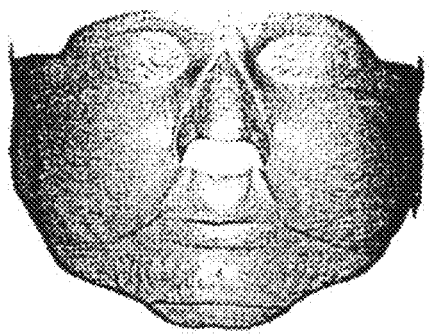
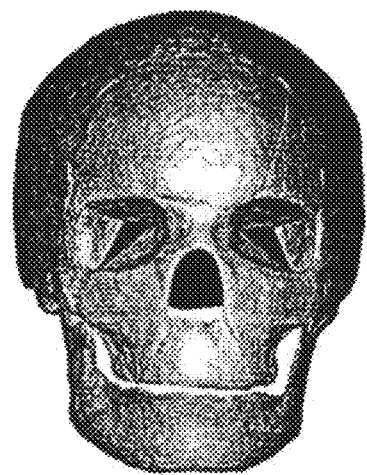
NYU Average Surfaces after Interpolated Normals.
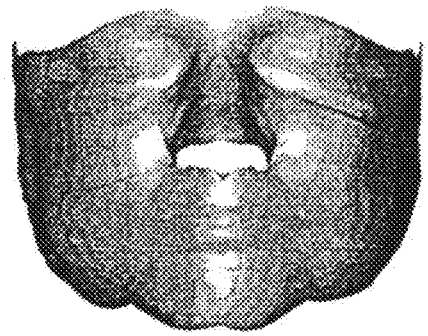
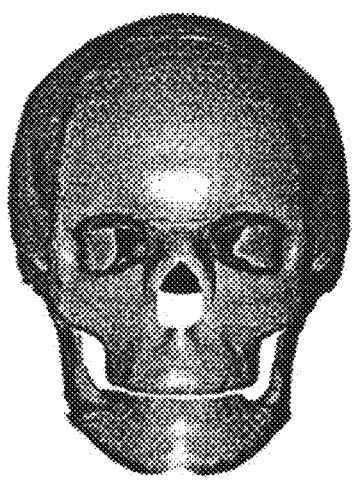
NYU Average Surfaces Prior to Normal Interpolation.
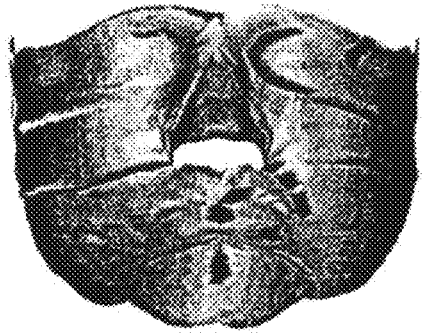
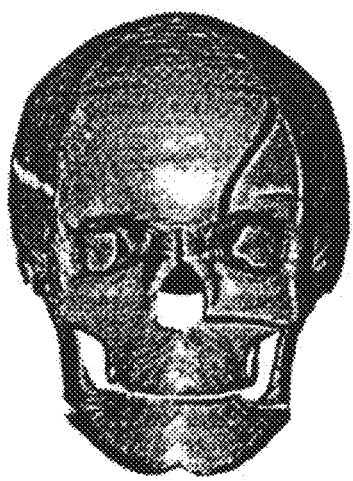
FIG. 44

PRODUCING A THREE-DIMENSIONAL MODEL OF AN IMPLANT

This application is a continuation of U.S. patent application Ser. No. 14/277,275, filed May 14, 2014, which is a continuation of U.S. patent application Ser. No. 12/720,518, filed on Mar. 9, 2010, which is a continuation-in-part of U.S. patent application Ser. No. 10/089,467, filed on Mar. 27, 2002, which is a §371 National Stage Application of PCT/US00/22053, filed on Aug. 11, 2000, which claims priority from U.S. Provisional Application Nos. 60/148,275, 60/148,277 and 60/148,393, which were all filed on Aug. 11, 1999. U.S. application Ser. No. 12/720,518 is also a continuation-in-part of U.S. patent application Ser. No. 10/129,308, filed on Sep. 3, 2002, which is a §371 National Stage Application of PCT/US00/41821, filed on Nov. 3, 2000, which claims priority from U.S. Provisional Application No. 60/163,323, filed on Nov. 3, 1999.

BACKGROUND OF THE INVENTION

The present invention relates to fabricating implants to replace bony structures. More specifically, the invention relates to a system and methodology for fabricating a "drop in" replacement for a particular segment of missing bony structure, in which the implant fits precisely within the contours of the missing segment and thus minimizes complications during the surgical procedure to install the implant, and subsequently during the healing process. It will be appreciated, however, that the invention is also amenable to other like applications.

Various systems and methods of fabricating prosthetic implants are known in the prior art. Examples of such prior systems and methods include U.S. Pat. Nos. 4,436,684; 5,274,565; 5,357,429; 5,554,190; 5,741,215; and 5,768,134. Each of these patents, however, suffer from many disadvantages that have collectively limited the usefulness of their methods and implants to the relevant field.

Neural Network Segmentation

Although clinical visualization of three dimensional organ surfaces embedded in an imaged volume is now common, segmentation techniques are often ineffective and time consuming. Current three dimensional (3D) surface segmentation is often dependent on the contrast and resolution of two dimensional (2D) anatomical boundaries identified by an operator proceeding slice by slice through the image volume. Existing automated 3D surface and volume segmentation algorithms, such as region growing, are most commonly based on voxel intensity, nearest neighbor similarity, and edge strength. An active contours energy minimization approach attempts to automate 2D outline detection. An extension to 3D suggests regions to be segmented by internally enveloping them with three dimensional bubbles. Another method based explicitly on high level volumetric shape features utilizes prior information obtained from previously imaged anatomical objects. This approach is based on prior morphological knowledge and a highly integrated set of model based grouping operations. The use of prior information allows the last method to be more adaptive to an expected surface when it encounters noise due to artifact or non-descript structures such as in thin areas. However, detection of anatomical surfaces as complex as the skull or soft tissue face with prior information alone is computationally expensive. It is likely manual work will be necessary where the signal is too low, especially in regions with high artifact noise or where artifact-interrupted surface morphology may obfuscate a match with database information. The relationship of artifacts to surface morphology is dependent on both surface proximity to the artifact-generating structure and patient pose. To overcome these limitations, a third approach, combines semi-automatic image segmentation procedures with intelligent scissors. A user steers the image segmentation via live wire and live lane tools through the image volume.

Current slice-based segmentation methods tend to be time consuming. Imprecision correlates with the numbers of decisions the operator is forced to make. These are concentrated in areas of poor contrast, artifact, or insufficient geometry for the user to recognize local aspects of the patient's anatomy (i.e., the sufficiency of anatomical cues are heavily dependent on structural site and degree of curvature as well as how patient pose affects the representation in tomographic images). Difficulty in making segmentation decisions used on these three (3) types of information may be compounded by a user environment where an image volume is presented as a series of tomographic or projection images that lose resolution when reformatted. In all cases these two dimensional views require anticipation of how the segmented outlines will combine to form the 3D surface that the user wishes to render.

Deformable curve fitting for edge detection seems less adaptable than manual segmentation for determining the location of anatomical edges. Curve fitting runs into trouble when edges vary in signal strength, requiring multiple initialization and guidance steps to obtain best-fit. An operator familiar with the salient anatomy quickly adapts to provide continuity between areas of material inhomogeneities (i.e., varying pixel intensity) that may signal a break to an edge detection algorithm. It is possible that these edges can be spanned by the use of geometrically ideal shapes or those based on prier information. However, these simple models are less adaptable, or less decisive, than manual segmentation.

Neural networks, applied to volume image segmentation, are capable of modeling structural components in the image through the processing of the gray scale and spatial information recorded in volume images. They take advantage of the multidimensional nature of medical images. Neural network classification can be either supervised or unsupervised. To date, supervised neural networks have been preferred, despite their dependence on user interaction to train or correct their results. Unsupervised neural networks do not rely on pre-labeled samples. Rather, they require careful selection of input events that, when clustered, are useful to the user.

Fitting a Deformable Template to a Segmented Surface

There is debate as to whether comparison of three dimensional (3D) anatomical shapes should be done on the basis of whole objects or elementally. One conventional method for 3D anatomical surface parsing begins with identification of a specialized class of space curves, which are referred to as "ridge curves."

A consensus ridge curve definition would cite a maximum first principal curvature along sharp edges as allowing their representation as a space curve. The curvature found along ridge curves is regular enough that a class of curvature extremal landmarks can be readily detected. These are referred to in the literature as Type II landmarks, which may be extracted manually or automatically. These landmarks may form the initial seed points on which to register a wire frame (i.e., ridge curve and "geodesic" lines) plate. "Geodesic" space curves, a shortest path traversed on a graphical manifold, are useful as a means to link Type II landmarks. The resulting fitted ridge curve and "geodesic" wireframe are used as a means to tile out and parameterize 3D surface images. This toolkit allows parameterized (labeled) surface extractions, multi-surface registration, and averaging for cephalometric comparisons of the skull, soft tissue face, and cerebral ventricles.

In regards to parameterized 3D surface extraction, the toolkit facilitates an initially manual superimposition of a ridge curve-based deformable template to the perspectively rendered surface of interest at the Type II landmarks. However, there is only an approximate tie between the surface tile points bounded by ridge and "geodesic" space curves, and the surface voxels originally identified (segmented) in the raw CT or MR scan volume image data. The "geodesic" criteria are less appropriate and these lines have been renamed "tiling curves." Additionally, the entire surface is encoded as set of B-spline space curves, in order to facilitate whole surface averaging algorithms, (i.e., to average multiple surfaces space curve by space curve). The toolkit links biological labeling (homology mapping) and geometric surface subdivision, resulting in a homology mapped (tile name) parameterized (u, v space of tile) surface.

The primary basis for positioning multiple biological surfaces for conventional averaging is as specialized class of space curves referred to as "ridge curves". One definition of ridge curves describes them as biologically significant space curves found along sharp edges, corresponding to first principal curvature maxima. These sharp edges are the most bent part of the surface. Type II landmarks, identified as recurrent curvature maxima (bends), are found along ridge curve space curves. They span these landmarks with what are called "geodesics" in order to create three or four sided tiles ("tiling curves").

It has been proposed to add tile parameters (i.e., tile u,v coordinates and tile name) to the xyz point coordinates found in 3D skull surface images to produce a feature-preserving average or morphometric comparison of homologous landmark. A geometric subdivision (ridge curve and geodesic tile boundaries) of the surface links biological labels (homology mapping) to tile grid (u, v) parameterization of the extracted points (x, y, z). The toolkit begins superimposition of the ridge curve and geodesic (tiling curve) deformable wireframe template with the identification of Type II landmarks. Using a thin plate spline, the ridge curve and geodesic template wireframe is warped to the surface's Type II landmarks. Superimposition of the interceding ridge curve and geodesic wire segments to best position proceeds automatically.

Averaging of Multiple Tiled Out Specimens

When too much of the patient is missing from the image, it is useful to match the average to the patient to obtain a reasonable shape to fill the defect. Unlike images of individuals, averages are usually relatively smooth and symmetric (right to left). However, estimating the shape of a defect of large size with an average of too few subjects is also not helpful. In this case, it may be better to use the image of a single relative.

Homology-based 3D surface averaging requires appropriate superimposition of sample member surface points within a shared reference frame. The toolkit obtains this position in a series of global warping and local unwarping maneuvers. First an average of all sample specimen's Type II landmarks is obtained. Each specimen is then globally warped to these landmarks and then locally unwarped. A rough average of the ridge and geodesic curve sample is produced. Next, because the space curve sample members are fit to the resulting rough average space curve, perpendicular bisectors may be positioned equidistantly along the rough average. An average of the intercepted points appropriately samples the shape of each space curve on the entire surface. The u, v parameters determine the number of points along either side of the four (4) sided tiles and, therefore, contain u x v internal space curves, which are averaged in the same manner as the boundary curves. This method insures that these sampling planes (perpendicular bisectors) are never parallel to the sampled data.

The present invention provides a new and improved apparatus and method which overcomes the above-referenced problems and others.

The present invention relates to fabricating implants to replace bony structures. More specifically, the invention relates to a system and methodology for fabricating a "drop in" (i.e., the prosthetic's fit is prefabricated taking into account all of the subject's anatomy surrounding the site where it will sit) quality replacement for a particular segment of missing bony structure, in which the implant fits precisely replacing the contours of the missing segment and thus minimizes length and complications during the surgical procedure to install the implant, and subsequently facilitates the healing process. Current standard of care is to mass produce a "shape" that matches the patient's anatomy in only few dimensions that are obtained by external measurements. Often parts of the patient's anatomy must be removed to get a good fit. Anything else is referred to as a "custom tooling" device by the FDA. This patent presents a method to prefabricate as custom (i.e., fits all dimensions of the defect site) prosthetic from imaging data. The implant requires only placement and minimal fixation by the attending clinician. It will be appreciated, however, that the invention is also amenable to other like applications.

Various systems and methods of fabricating prosthetic implants are known in the prior art. Examples of such prior systems and methods include U.S. Pat. Nos. 4,434,684; 5,274,565; 5,357,429; 5,554,190; 5,741,215; and 5,768,134. Each of these patents, however, suffer from many disadvantages that have collectively limited the usefulness of their methods and implants to the relevant field.

The primary disadvantage of these methods is that they do not provide a mechanism for ensuring that the implant will be a "drop in" replacement for the missing bony material. More specifically, the implant may not be the correct shape and/or size and, therefore, not properly fit the prosthetic into the patient. Without a proper lit, there can be a wide variety of complications with the implant, including complications that arise during the surgical process as well as during the healing process. Ultimately, these complications may result in the patient experiencing pain, disuse, atrophy, implant or surrounding structure mechanical failure, and/or the body rejecting the implant. Thus, it is a critical disadvantage of these prior art systems and methods that they do not provide the ability to ensure a custom fit, "drop in" replacement for the missing body segment.

The present invention provides a new and improved apparatus and method which overcomes the above-referenced problems and others.

SUMMARY OF THE INVENTION

A method for determining a shape of a medical device to be implanted into a subject produces an image including a defective portion and a non-defective portion of a surface of a tissue of interest included in the subject. The tissue of interest is segmented within the image. A template, representing a normative shape of an external anatomical surface of the tissue of interest, is superimposed to span the defective portion. An external shape of an implant, is determined as a function of respective shapes of the defective portion as seen in the template, for repairing the defective portion.

In accordance with one aspect of the invention, a volumetric image of the tissue of interest is produced. In accordance with a more limited aspect of the invention, one of a CT and MR image is produced.

In accordance with another aspect of the invention, a position for seating the implant into the defective portion is determined. The implant is tapered as a function of a seating strategy and a space available for the implant.

In accordance with another aspect of the invention, the template is superimposed to the surface of the tissue of interest via warping.

In accordance with another aspect of the invention, the template is warped to an external surface of the non-defective portion of the tissue of interest.

In accordance with another aspect of the invention, a ridge and tiling curve homology map is produced of another anatomical surface. The average nonnative shape is produced from control surface image representations of the anatomical surface of interest.

In accordance with a more limited aspect of the invention, the normative shape is determined from a mirror image of the tissue of interest.

In accordance with another aspect of the invention, the normative shape is modified as a function of a shape of the non-defective portion of the anatomical surface of interest.

A system determines a shape of a medical device to be implanted into a subject. An imaging device produces an image including a defective portion and a non-defective portion of a tissue of interest included in the subject. A segmenting means segments the tissue of interest. A template spans the defective portion. The template represents a normative shape of an external anatomical surface of the tissue of interest. A determining means determines an external shape of an implant, as a function of respective shapes of the defective portion and the template, for repairing the defective portion.

In accordance with one aspect of the invention, the image is a volumetric image of the anatomical surface of interest.

In accordance with a more limited aspect of the invention, the volumetric image is one of a CT and MR image.

In accordance with another aspect of the invention, the template specifies a seated edge, which is fixed to the subject, and a surface shape, which is not affixed to the subject.

In accordance with another aspect of the invention, the template is warped to a deformed bone.

In accordance with another aspect of the invention, the template is warped to an external surface of the non-defective portion of the tissue of interest.

In accordance with another aspect of the invention, the normative shape of the template is determined from an additional tissue representative of the hard tissue of interest.

In accordance with another aspect of the invention, the normative shape of the template is determined as a function of an average shape of the tissue of interest.

A method for repairing a defect in a tissue of interest included in a subject produces a volumetric image showing a defective portion, which includes the defect, and a non-defective portion of the hard tissue of interest within the subject. The tissue of interest is segmented from the image. A template, having an average shape of the tissue of interest, is warped over the defective and non-defective portions. A shape of the implant is determined, as function of respective shapes of the defective portion and the template. The implant is inserted into the defective portion for repairing the defect.

In accordance with one aspect of the invention, the implant is cast.

In accordance with another aspect of the invention, a mirror of another tissue of interest, representing a bilateral mirror image of the tissue of interest, is homology mapped. The normative shape is determined from the mirrored other section of tissue.

One advantage of the present invention is that it presents an unsupervised neural network algorithm (i.e., self organizing feature map, or SOFM) for automated and accurate 3D surface segmentation, the latter being a necessity for computer generation of cranial implants, diagnostic cephalometrics and image guided surgery.

Another advantage of the present invention is that user interaction in the SOFM algorithm is limited to determining which segmented surfaces represent the anatomy desired by the user.

Another advantage of the present invention is that it rapidly assembles automatically segmented, and anatomically valid (i.e., no correction required), surfaces into a surface of interest for rendering of 3D surfaces found in volume images.

Another advantage of the present invention is that it saves time over manually identifying each pixel or currently available semi-automatic methods.

Another advantage of the present invention is that it locates continuous surfaces, even in areas of thin structure, or imaging artifact (e.g., metallic artifact in x-ray or CT).

Another advantage of the present invention is that it combines spatial and intensity information to track 3D surfaces for segmentation.

Another advantage of the present invention is that it provides a means for anatomically valid segmentation (because 3D surfaces are tracked oblique to the scan plane, irrespective of patient pose (orientation of scan planes are determined relative the patient anatomy) in the scanner).

Another advantage of the present invention is that it provides a warping method that gives precise, accurate and efficient ridge curve-based template registration for extraction of a parameterized surface.

Another advantage of the present invention is that a fitted template allows matching of mirrored (filling defect with right or left opposing side data) or average (normative) surfaces, and production of averages. The template establishes the homology for these three types of surface matching (i.e., mirroring, one-to-one fit, averaging).

Another advantage of the present invention is that it provides a reduced time for the warping method that is largely due to an automated (simulated annealing) search for ridge and tiling curves in the volume image.

Another advantage of the present invention is that it provides faster and more reproducible and, consequently, more reliable automated ridge and tiling curve fitting, especially for internal tile points which were previously generated from an error map between an ideal surface and the true surface.

Another advantage of the present invention is that it provides a new basis for determining tiling curve and internal tile point location by establishing more reliable homology mapping of these features.

Another advantage of the present invention is that it provides a template fitting and surface averaging method that will work well on the entire external surface of the body, as well as many internal organs.

Another advantage of the present invention is that it encodes the entire surface as series of B-spline space curves, including the internal tile points.

Another advantage of the present invention is that all surface operations (e.g., registration or averaging) may be accomplished with series of homologous space curves, rather than whole surfaces, thereby allowing for computationally less expensive serial or parallel processing of space curve sets.

Another advantage of the present invention is that it improves the homology assignment of both tiling curves and internal the points through new surface extraction techniques.

Another advantage of the present invention is that it uses average 3D surface images to model surfaces in patient images for rapid prototyping of prosthetic implants.

Still further advantages of the present invention will become apparent to those of ordinary skill in the art upon reading and understanding, the following detailed description of the preferred embodiments.

A method for creating a 3-dimensional model of a tissue of interest, included within a subject, and a plurality of fiducials positions the fiducials in a fixed relationship to the subject. Data representing a volume image of the fiducials and the tissue of interest is obtained. Respective measurements between the fiducials in the fixed relationship to the subject and in the image data are validated. The tissue of interest and the fiducials are segmented from the image data. Points of the tissue of interest and the fiducials are rendered as a 3-dimensional surface representation. The 3-dimensional model of the tissue of interest and the fiducials is created as a function of the surface representation.

In accordance with one aspect of the invention, the positioning of the fiducials includes placing markers on the subject. The markers have a density for creating an identifiable spot in the volume image.

In accordance with another aspect of the invention, the positioning of the fiducials includes placing a frame of markers, which have a density for creating an identifiable spot in the volume image, around the tissue of interest.

In accordance with another aspect of the invention, the validating includes comparing distances between the markers in the fixed relationship to the subject and in the image data.

In accordance with another aspect of the invention, positional errors detected in the validating step are mathematically corrected.

In accordance with another aspect of the invention, respective measurements between the fiducials in the fixed relationship to the subject and in the surface representation are validated.

In accordance with a more limited aspect of the invention, respective measurements between the fiducials in the fixed relationship to the subject and in the 3-dimensional model are validated.

In accordance with another aspect of the invention, the image data is interpolated for smoothing the surface representation.

In accordance with another aspect of the invention, the fiducials are bridged to the tissue of interest.

One advantage of the present invention is that a drop in implant is created.

Another advantage of the present invention is that an implant having substantially the correct shape and/or size is created.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 6 illustrates Gaussian and Zero crossing curves;

FIG. 7 illustrates processor network configurations according to the present invention;

FIGS. 12A and 12B display the resulting triangulated surface rendered soft tissue face and skull. FIGS. 12C and 12D present the voxel back projection from the selected feature cluster nodes; FIG. 12E presents the feature cluster map;

FIGS. 19A and 19B illustrate Type II landmarks of the soft tissue face and boney skull templates;

FIGS. 20A and 20B illustrate a CT slice highlighting segmented surface voxels of interest which are indexed to vertices (points) in an adjacent rendered manifold surface;

FIG. 29 illustrates a temperature cooling schedule from an initial temperature 100 to a final temperature −10.

FIG. 38A illustrates a translation of two shapes into a shared two dimensional common coordinate system;

FIG. 38B illustrates scaling adjustments between the two shapes;

FIG. 38C illustrates the rotation, in order to obtain the Procrustes distance (square root of sum of squared) between homologous point landmarks pairs: A . . . D, a . . . d;

FIG. 40A illustrates a soft tissue face average surface generation;

FIG. 40B illustrates a skull average surface generation;

FIG. 41A illustrates a soft tissue face surface average comparison of various methods;

FIG. 41B illustrates a boney skull surface average comparison of various methods;

FIG. 44 illustrates an inter-method average surface continuity.

DETAILED DESCRIPTION

Figure 1:
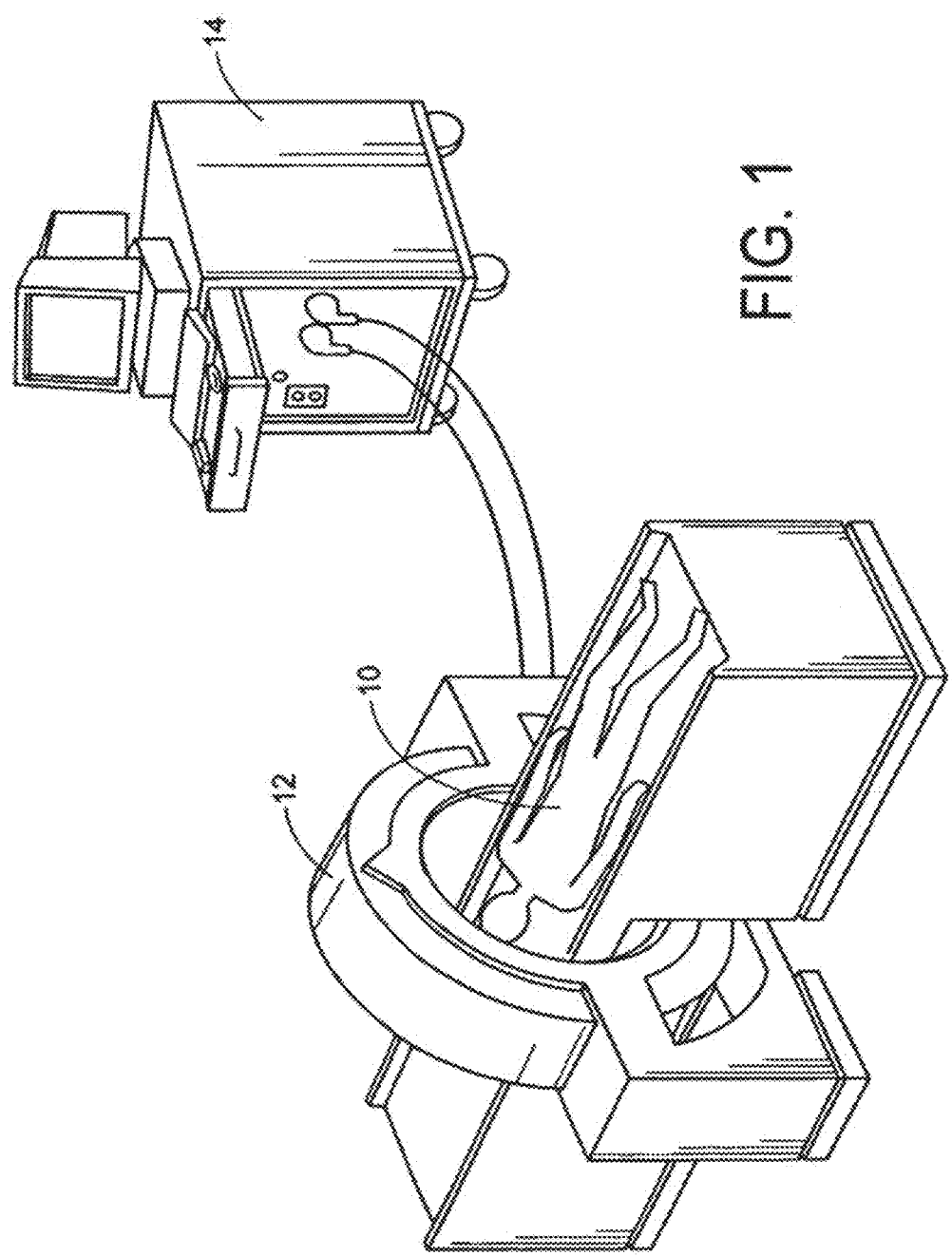
FIG. 1 illustrates a system of the present invention.
Figure 1A:
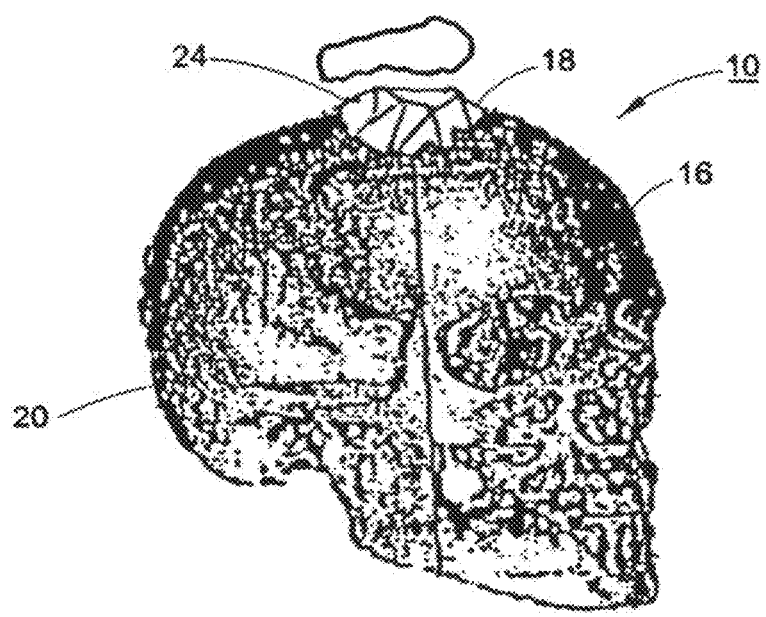
FIG. 1A illustrates a bone of interest according to the present invention.
Figure 2:
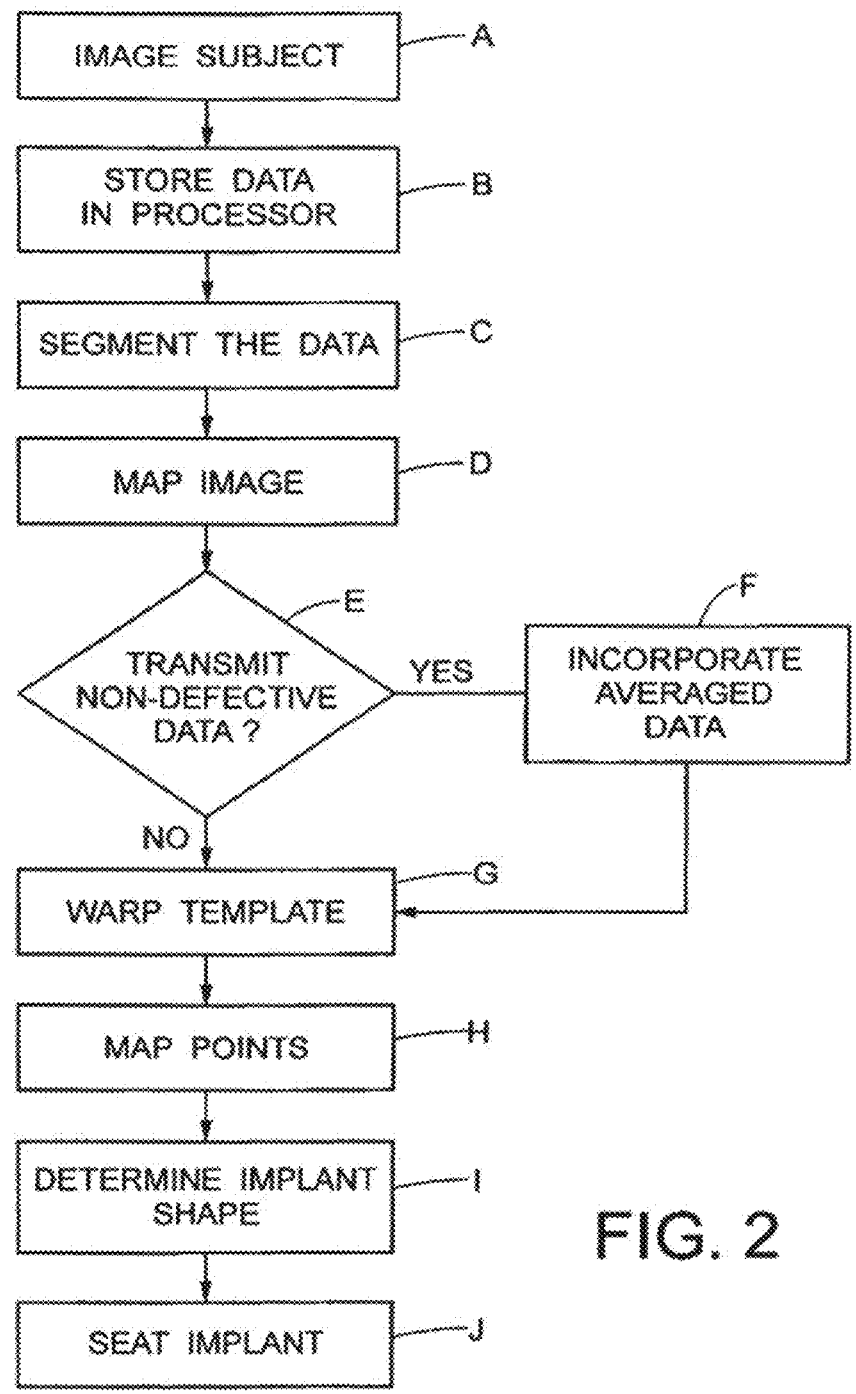
FIG. 2 illustrates a flowchart according to the present invention.

With reference to FIGS. 1A, and 2, a subject 10, or patient, is imaged using an imaging device 12 in a step A. Preferably, the image is a volumetric image obtained using a computerized tomography ("CT") scanner according to a preferred protocol. However, other images, obtained using other imaging techniques (e.g., magnetic resonance) are also contemplated. Once the data is captured from the CT scanner 12, it is stored in a processor 14 (preferably, a transportable storage medium) in a step B (although it could be transferred over a network). Then, the processor 14 segments the data in a step C for extracting a region of the image including a target tissue (e.g., liver, lung, or hard tissue such as bone) 16 of interest within the subject; the extracted region 16 includes two (2) portions (i.e., one portion having a defect 18 and one portion 20 without the defect). Preferably, the non-defective portion 20 substantially surrounds the defective portion. An external surface of the extracted region 16 of the image is mapped in a step D. A decision is made in a step E whether to register the mapped data of the non-defective portion of the extracted region to a memory device in the processor 14, which includes normative (average) data for various bones as a function of various factors (e.g., race, sex, age, etc) of the subject. If the data is transmitted to the memory device, the data representing points on the mapped surface of the non-defective portion of the extracted region are incorporated into averaged data for the respective bone based on the various factors of the subject in a step F.

After the image is segmented and mapped, a template 24 is superimposed in a step G, to an external surface of a normative shape of the target tissue 16 (i.e., without the defect 18). Preferably the template is superimposed via warping. However, a best fit process is also contemplated. The template specifies a "seated" edge, which is fixed to the subject (patient), and the remaining surface shape, which is not affixed to the subject.

It is to be understood that the normative shape represents a desired or average shape of the target tissue. Preferably, the normative shape is determined in a bilateral structure from a substantially mirror image of the target tissue (e.g., a defect is present in a left side of a skull and complete data is available for a right (control) side of a skull). However, if too much of the target tissue is missing on the affected side, or the defect crosses the midline in a way that prevents establishing the midline, appropriate normative average surfaces (which, as described below, are already homology mapped) are used. In this case, the normative average data is brought in and registered to the homology mapped normative surface surrounding the defect. Once the template is warped, points on the template are mapped, in a step H, to points on the external surface of the normative shape of the bone of interest 16.

A shape of an implant 26 to be "dropped in" the defect 18 is determined, in a step I, as a function of a difference between the mapped points on the external surface of the target tissue and the external surface of the template. The implant 26 is seated (fit) in the defect 18 of the target tissue 16 in a step J. A fit of the implant (seating and shape relative to surrounding anatomy) is analyzed in order to produce an image description of the best shape for the implant on computer, not manually. That image description is saved in industry standard format, such as stereolithography (STL), and printed on a 3D rendering device (e.g., stereolithographic printer). The fit is then accomplished using a tapering scheme based on the seating strategy and space available for the implant.

If the implant is not produced in biocompatible material, it is cast in an implantable material. It is to be understood that the present methods work with inert casting materials (e.g., bioplastics such as Polymethymethacrylate) or future tissue engineered materials.

A stereolithography manufacturing method is contemplated for forming the either the implant master shape or the actual implant.

I. Segmentation

As described below, the step C of segmenting the image is preferably executed using self organizing feature maps ("SOFM"), which are used for computationally encoding neural maps.

The SOFM incorporates a modified Hebbian rule. The resulting mapping of data ordering resembles observed neurological patterns. Since then, the SOFM has found widespread use in many practical engineering applications. The SOFM derives primarily from observations of two biologically equivalent computational hypotheses defined as:

(1) The Hebbian Rule: "A synapse is strengthened or stabilized when pre- and post synaptic activations are correlated." Change in synaptic strength is defined as:

$$s_{i+1} = s_i + \alpha \cdot \eta \quad (1)$$

where $s_i$ is a connection strength at time t, $\eta$ is an output (IP in FIG. 4) equal to $s_i \times \xi$, $\xi$ is an input pattern, and $\alpha$ is a factor, a user-selected value, that is made to decrease for each iteration, to ensure it reaches zero. This, in turn, ensures appropriate synaptic strength formation and system stabilization.

Figure 3:
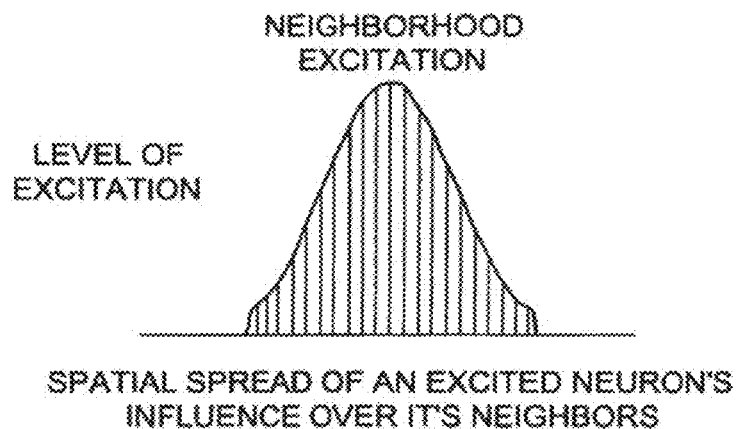
FIG. 3 illustrates a local negative feedback which excites neuron drop off allowing coordinated input of simulated neuronal field to a neural network.
Figure 4:
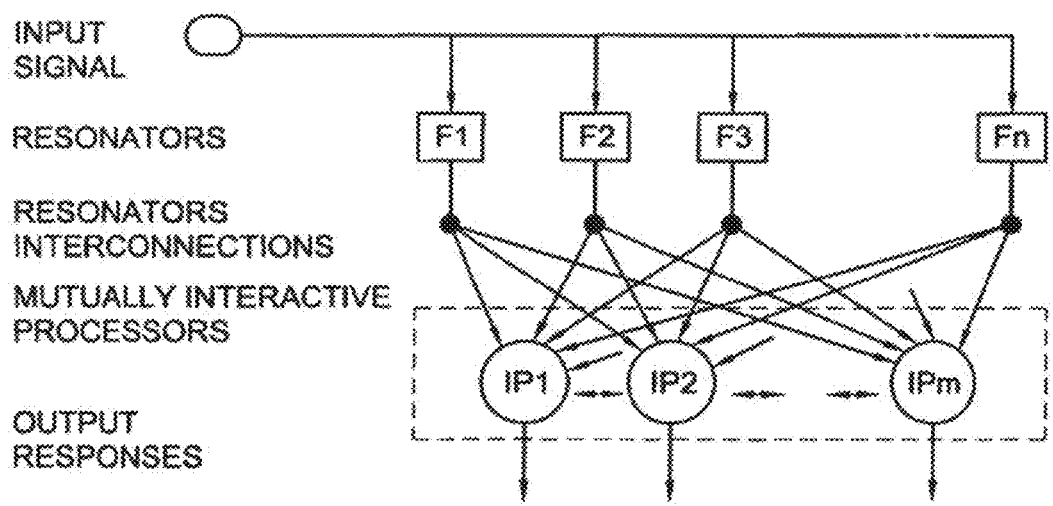
FIG. 4 illustrates event inputs to a Network.

(2) Local Feedback: Each neuron laterally influences the neighboring neurons to either an excitatory or inhibitory state. This results in a competition which enables the formation of a map. FIG. 3 is an example of an excitation function. The SOFM based 3D surface segmentation presented here extends the concepts of ordered feature maps. In the neural network, each normalized input feature vector is scaled or weighted by multiplication with a user-assigned constant vector. This process begins with an event generation step, which results in a pattern $\xi = \{\xi_1, \xi_2, \ldots, \xi_n\}$ that is sent to a "resonator" from which potential connection are made. The weights determine feature connection strengths. The scaling results in a vector xi=c*F, with c the feature connection strengths and F the input vector are shown in FIG. 4. Processor weights adapt to input stimulation and in so doing the neural network organizes an ordered map.

The unit $\mu$ has connection weights, $\mu_1, \mu_2, \ldots, \mu_n$, which are expressed as a column vector mi=$[\mu_1, \mu_2, \ldots, \mu_n]^T$. The discriminant function of a unit is defined as:

$$\eta_i = \sum_{j=1}^{n} \mu_{ij} \xi_j = m_i^T \xi \quad (2)$$

For unit k after selecting a winner from each iteration, the weight vector is updated as:

$$m_i(t\_1) = \frac{m_i(t) + \alpha \cdot (\xi - m_i(t))}{\|m_i(t) + \alpha \cdot (\xi - m_i(t))_N\|} \quad (3)$$

where t is the discrete point at which events are sequentially sent to the network. $\|O\|_N$ is the normalization process, ensuring the weight vectors are bounded. The network's selectivity improves as more input vectors are presented. Network formation requires no initial correlation or order between any of the voxel input data elements. Hence, no initialization or operator assistance is required during feature cluster formation. Iterative steps lead array units to represent the topological order of different combinations of input image features.

1. Voxel Input Data Elements (VIDE)

One dimensional feature maps with voxel intensity input data have been extended to include six (6) voxel input data elements (i.e., patterns) in a two dimensional processor and feature map for interactive surface segmentation. The image feature vector is generated for each input voxel, its elements are: (1) A distance from volume centroid to voxel location in three dimensional space; (2) The histogram equalized or normalized voxel intensity; (3) The Gaussian smoothed voxel intensity; 4) The difference of Gaussians; 5) The Laplacian zero crossings; and, 6) Invariant image moments.

The calculation of VIDE parameters is explained below. In general, intensity information is incorporated to provide voxel differentiation. Spatial distance parameters provide positional information, such as where a surface is located. Gaussian parameters used in self organizing map-based segmentation provide additional adaptive qualities to the 3D surface detection operation by smoothing artifact noise and compensating for scan protocol sequellae (resolution, pose, and beam strength). The "difference of Gaussian" parameter extends smoothing across a detected surface by introducing effects from local and distant voxels (i.e., the maximum distance between voxels is that of the surface detected but not elsewhere in the image volume). The "zero crossing" parameter provides transitional information important for some kinds of edge detection. The "moment invariant" parameters provide a positional and scale invariant signature of a surface in each region of the image volume; a computationally intensive parameter, moment invariants are initially set to 10 weight (Table I), and raised here only in small, user-defined, regions (e.g., the margins of thin structures) for fine tuning.

This set of voxel input data element vectors have normalized values of: spatial location via distance transform, voxel density with respect to nearest neighbors via Gaussian and difference of Gaussians, and boundary changes captured via Laplacian zero crossings. The two Gaussian input elements prevent feature inclusion of the spurious background noise commonly associated with 3D images. These parameters are computed during a preprocessing and feature-extraction procedure (see FIG. 5). All VIDEs are normalized to a unit range of 0 to 1.0. This bounds the neural network output (i.e., second layer produced from VIDE input).

The voxel input data element vectors are defined as row vectors $F_n = [E_{dn}, V_n, g, g_d, Z_c, m]$ with six (6) elements, shown in Table I, where n varies from 1 to the total number of input image voxels. The weighting factors are defined for each element in order to prefer one element over the others. The resultant VIDE vector $\xi$ is defined as:

$$\xi = \kappa F_n = [\kappa_1 E_{dn}, \kappa_2 V_n, \kappa_3 g, \kappa_4 g_d, \kappa_5 Z_c, \kappa_6 m] \quad (4)$$

where $\kappa_1$ defines the percentage of preference assigned for each VIDE. The differential preference of input VIDE results in associations between neural network processors and the voxel clusters. Table I presents the default preferences for each element during experiments.

A. Input Element 1: Normalized Euclidean Distance ($E_{dn}$)

The radial distance from the image volume centroid is referred to as the moment of inertia. The image volume centroid is ($C_x, C_y, C_z$) as determined from:

$$C_x = \left(\sum_{z=0}^{d}\sum_{y=0}^{h}\sum_{x=0}^{w} xV(x,y,z)\right) \bigg/ \left(\sum_{x=0}^{d}\sum_{y=0}^{h}\sum_{x=0}^{w} x\right),$$

$$C_y = \left(\sum_{z=0}^{d}\sum_{y=0}^{h}\sum_{x=0}^{w} yV(x,y,z)\right) \bigg/ \left(\sum_{x=0}^{d}\sum_{y=0}^{h}\sum_{x=0}^{w} y\right), \quad (5)$$

$$C_z = \left(\sum_{z=0}^{d}\sum_{y=0}^{h}\sum_{x=0}^{w} zV(x,y,z)\right) \bigg/ \left(\sum_{x=0}^{d}\sum_{y=0}^{h}\sum_{x=0}^{w} z\right)$$

where $V(x,y,z)$ is voxel intensity, d,h,w are number of slices, slice height, and slice width. Euclidean distances are computed from the centroid to each input voxel as $E_d = \sqrt{(x-C_x)^2 + (y-C_y)^2 + (z-C_z)^2}$. This distance is normalized as $E_{dm} = E_d / \|E_d\|_{max}$.

B. Input Element 2: Normalized Voxel Density ($V_n$)

This value depends on a prior choice of gray scale histogram normalization or equalization via a lookup table procedure. The value $V_n = f(V(x,y,z))/\|f(V)\|_{max}$ is calculated from histogram mapping and normalized with the maximum value obtained from the entire volume. The best results are obtained via may scale equalization.

Input Element 3: Gaussian (g)

A 3D Gaussian is defined as:

$$G(x,y,z) = \frac{1}{2\pi\sigma^2} e^{-(x^2+y^2+z^2)/(2\sigma^2)} \quad (6)$$

where $\sigma$ defines the spread of the Gaussian curve as shown in FIG. 6. Use of two Gaussian features allows the neural network to produce feature clusters in noisy regions. Pre-computed numbers are used to normalize the 3D Gaussian. A kernel is computed from this Gaussian function with pre-specified kernel size ranging from 2 to 10. The smoothed voxel intensity results from the convolution of the kernel over the present voxel and its immediate three (3) dimensional neighbors.

D. Input Element 4: The Difference of Gaussians ($E_d$)

This is an extension of the above Gaussian input element with dual $\sigma_1, \sigma_2$ values, shown separately in FIG. 6. This is defined as:

$$G_d(x,y,z) = \|G_1(x,y,z) - G(x,y,z)\| \quad (7)$$

where $$G_1(x,y,z) = \frac{1}{2\pi\sigma_1^2} e^{-(x^2+y^2+z^2)/(2\sigma_1^2)}$$

and $G(x,y,z)$ is defined in equation 6. As in Equation 6, pre-computed numbers are used to normalize this Gaussian function. A kernel is computed from $G_d(x,y,z)$ and $g_d$ is (2×) obtained by convolving this kernel with the present voxel and its immediate neighbors (i.e., the 6 directly adjacent voxels).

E. Input Element 5: Laplacian Zero Crossing ($Z_c$)

Laplacian Zero Crossings are presented by as:

$$Z_c(x,y,z) = \sqrt{(Z_c(x) + Z_c(y) + Z_c(z))} \quad (8)$$

this value is obtained from the Laplacian computed in each axis in the image volume, where:

$$Z_c(x) = \left(\left(\sum_{m=d}^{-d}\sum_{m=d}^{-d} V(x, y+n, z+m) \cdot \operatorname{sgn}(n)\right) \bigg/ L\right)^2,$$

$$Z_c(y) = \left(\left(\sum_{m=d}^{-d}\sum_{m=d}^{-d} V(x+p, y, z+m) \cdot \operatorname{sgn}(n)\right) \bigg/ L\right)^2,$$

$$Z_c(z) = \left(\left(\sum_{m=d}^{-d}\sum_{m=d}^{-d} V(x+p, y+n, z) \cdot \operatorname{sgn}(n)\right) \bigg/ L\right)^2$$

and, where sgn(n) is the sign of the scalar x. L is equal to (2d+1)d where d is a predefined length; and V is voxel intensity.

F. Input Element 6: Moment Invariant ($m_1$)

The moment invariant is an image statistic that is invariant to rotation, translation, and scale in a region. Moment invariants are derived from the definitions of moments, centralized moments, and normalized central moments. The image moments are defined as:

$$m_{pqr} = \sum_x \sum_y \sum_z x^p y^q z^r f(x,y,z) \quad (9)$$

where p,q,r ∈ {0, 1, . . . , 1}. If $f(x,y,z)$ is a piece-wise continuous function with bounded support in a 3D image, then the bounding is set by an m×n×o voxel array. It is positioned at the selected voxel and bounded by length l. The centralized moment $\mu_{pqr}$ is defined as:

$$\mu_{pqr} = \sum_x \sum_y \sum_z (x-\bar{x})^p (y-\bar{y})^q (z-\bar{z})^r f(x,y,z) \quad (10)$$

where $\bar{x}=m_{100}/m_{000}$, $\bar{y}=m_{010}/m_{000}$, $\bar{z}=m_{001}/m_{000}$ (i.e., centroid coordinate) and the point (x,y,z) is called the image region centroid. The normalized central moment is defined as: $\eta_{pqr}=\mu_{pqr}/\mu_{000}$ where $\gamma=(p+q+r)/2+1$. From the normalized central moments, three (3) orthogonal invariant moments are defined as:

$\phi_1=\eta_{200}\cdot\eta_{020}\cdot\eta_{002}$, $\phi_2=2\eta_{110}\cdot\eta_{011}\cdot\eta_{101}$, $\phi_3=\eta_{020}\cdot\eta^2_{101}+\eta^2_{011}\cdot\eta_{200}+\eta^2_{110}\cdot\eta_{002}$ (11)

These three orthogonal moment invariants were selected because they are irreducible and distinct. When approaching tissue boundaries the moment invariants may provide information that complements the zero crossing data. The strength of the zero crossing 3D surface signal is expected to be more dependent on the object's pose (i.e., relation of surface orientation to scan orientation) than the moment invariants.

2. Back Projecting of Feature Clusters

Figure 5:
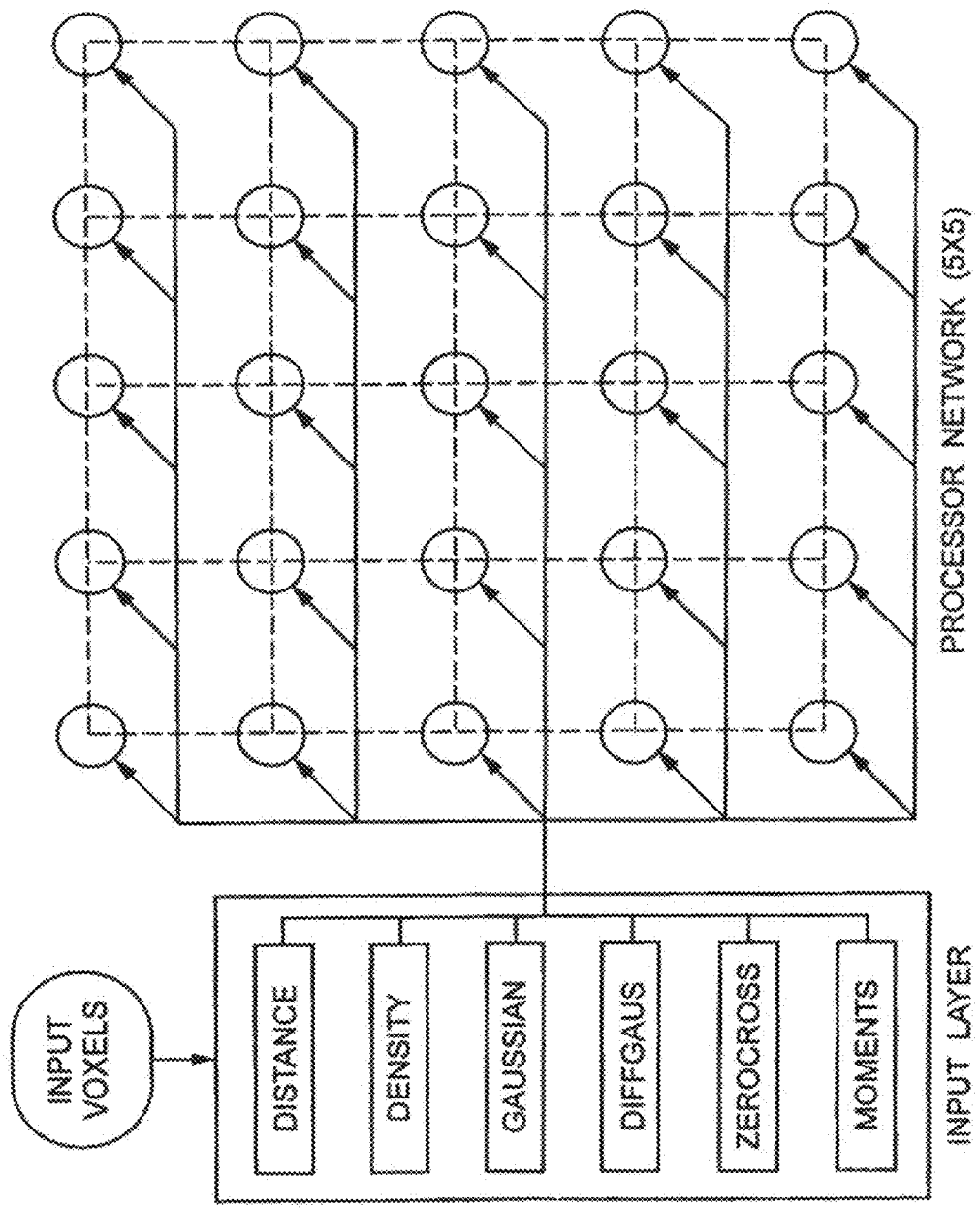
FIG. 5 illustrates a current implementation of a SOFM neural network configuration shown as flow of event space image element input to processor layer of neural network.
Figure 8:
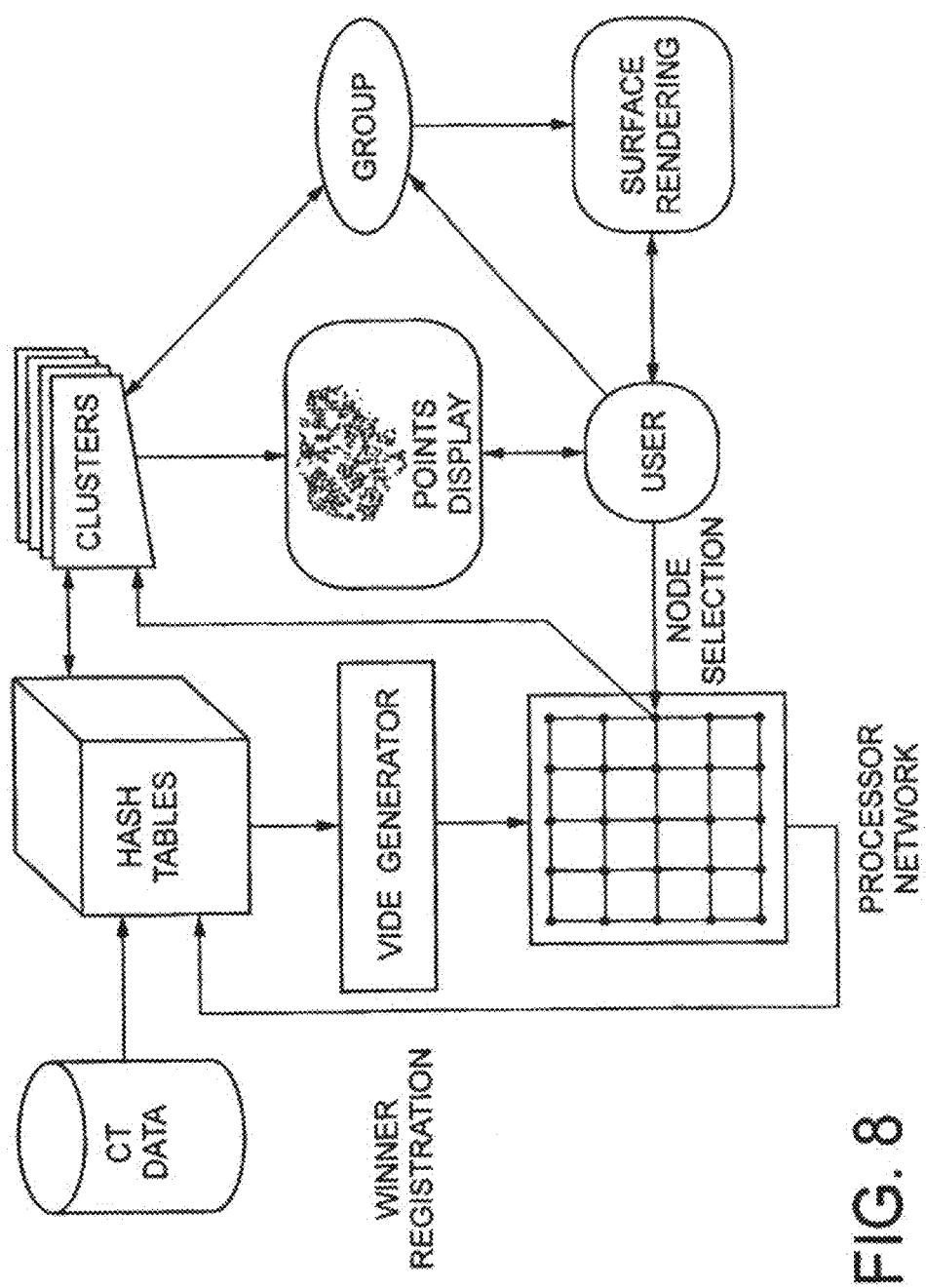
FIGS. 8 and 9 illustrate flowcharts of the segmentation process.

In the preferred embodiment, the SOFM neural network utilizes 4×4 to 16×16 processor network configurations in either a rectangular or a hexagonal grid formation (see FIG. 7). In a rectangular grid, each processor has four connections to its neighbors. In a hexagonal grid, each processor unit has six connections to its neighbors. The input layer, translates each voxel into a vector containing the VIDEs defined in Equation 4. The input layer has direct connection to all processors in the formative network configuration and is associated with a weight as shown in FIG. 5. A flowchart of the complete surface segmentation process is shown in FIG. 8.

A. Preprocessing to Remove Background Noise and Head Holder

The head holder and background noise are separated from the head object in a two step procedure. First, a grayscale threshold is manually set; next, a volumetric region growing method is applied. This removes voxels associated with the head bolder, background noise, and most metallic artifact outside the head; it also limits the voxels sent to the neural network to those relevant to the 3D surfaces internal to the head.

B. Randomization of Input Voxels

The randomization of the VIDE vectors in the input event space is necessary in order to obtain an ordered map. Each voxel intensity in the image volume is stored along with its position (i.e., x, y, z coordinates) in a randomly selected entry in a hash table (i.e., a register queue length N). The random position $R_p$ in the hash table is computed as $R_p$=hashTable[length×randNumber], where the hash table is initialized sequentially from 0 to the total number of voxels N. The random number is generated in a range between 0.0 and 1.0. The length of the hash table starts with value N. Subsequently, N decrements for each position computed and is swapped with entries for that position's current length in the hash table. This procedure ensures randomization of feature vectors in the input element event space and, subsequently, the map formation by adapting weights in the self organization process. The position of the intensity in the hash table entry is replaced during map formation with the processor identity; processors represent feature clusters of potential anatomical surfaces.

C. Self-Organizing Feature Map Algorithm

Figure 9:
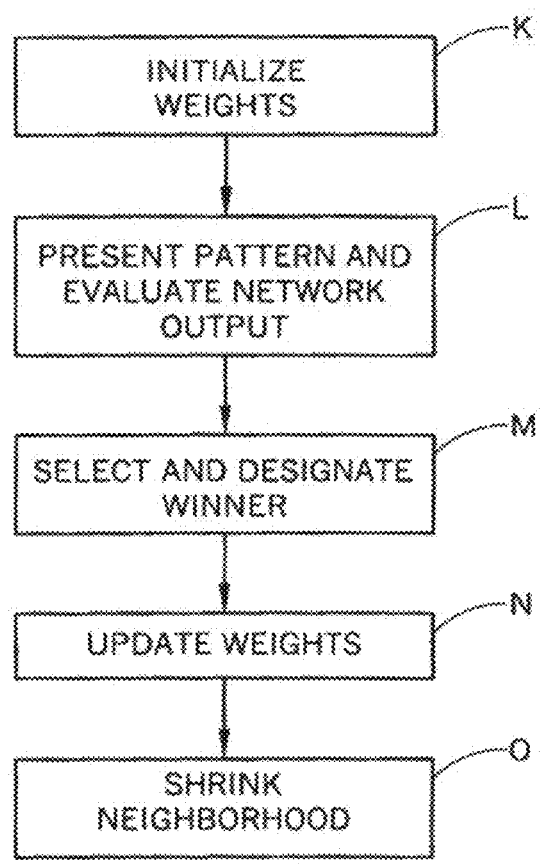

With reference to FIGS. 8 and 9, weights are randomly initialized around 0.5±x,x ∈ {0.0, . . . , 0.1}, in a step K, with default initial learning rate and neighborhood excitation parameters, set by the user.

A pattern $\xi$, a VIDE vector, is presented, and the network output is evaluated in a step L.

The unit (i,j) with the minimum output is selected and designate as a winner: $|p_{i,j}|_{winner}=\|\xi-W_{i,j}\|_{min}$, in a step M.

Weights are updated, in a step N, using a learning rule where neighbor excitement levels are a function of self and neighbor excitation rates $|W_{i,j}(t+1)|_{winner}=W_{i,j}(t)+\alpha_{i,j}(t)\cdot[\xi-W_{i,j}(t)]$, $$W_{m,n}(t+1) = \begin{cases} W_{m,n}(t) + \beta_{i,j}(t)\cdot[\xi - W_{i,j}(t)], & \text{if}((m,n) \in N_{i,j}(t) \\ W_{m,n}(t) & \end{cases},$$

where $N_{i,j}(t)$ is a neighborhood of (i,j) at time t; $\alpha_{i,j}(t)$, the learning rate for the winner processor; $\beta_{i,j}(t)$, is the rate at which its excitation influences its neighbors.

The value of $\alpha_{i,j}(t)$ and $\beta_{i,j}(t)$ is decreased, and the neighborhood, $N_{i,j}(t)$ is shrunk in a step O.

Steps K-O are repeated for all the VIDE vectors:

$Q_{i,j} = [w_1, w_2, w_3 \ldots w_6]$ $i = 1, 2, \ldots, I$ $j = 1, 2, \ldots I$ $I \times I$ $I \in \{4 \ldots 16\}$ $Q_{i,j} = \|\kappa F'_n - W_{i,j}\|$ $n \in \{1 \ldots N\}_N Q_{i,j}\alpha_{i,j}(t)\beta_{i,j}(t)\beta_{i,j}(t)\gamma_{i,j} id \in \{0 \ldots 255\}W_{i,jN}$.

3. Interactive Image Segmentation and Rendering

The SOFM 3D surface segmentation program integrates the SOFM algorithm, volumetric image reading, slice image display and editing, and graphical surface rendering of output feature cluster voxel data (i.e., obtained 3D surfaces).

Figure 10:
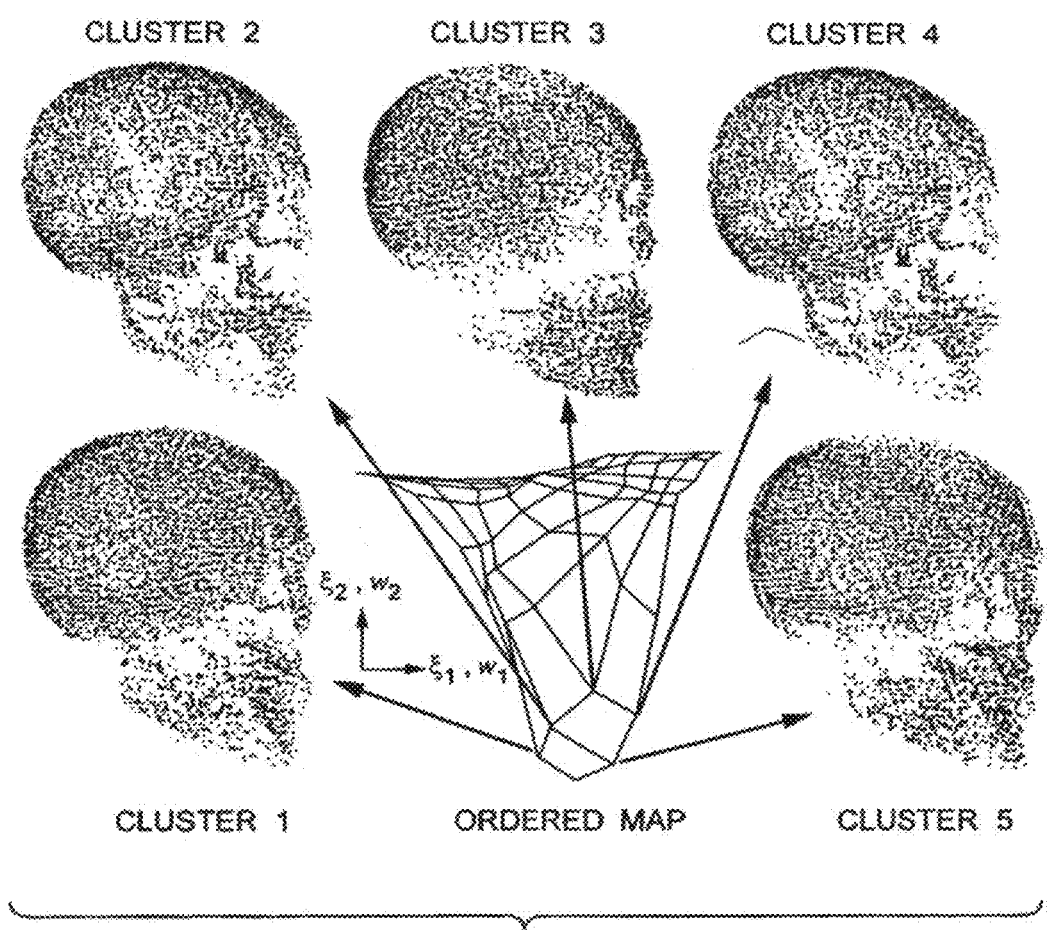
FIG. 10 illustrates multiple cluster back-projection from map nodes.
Figure 11:
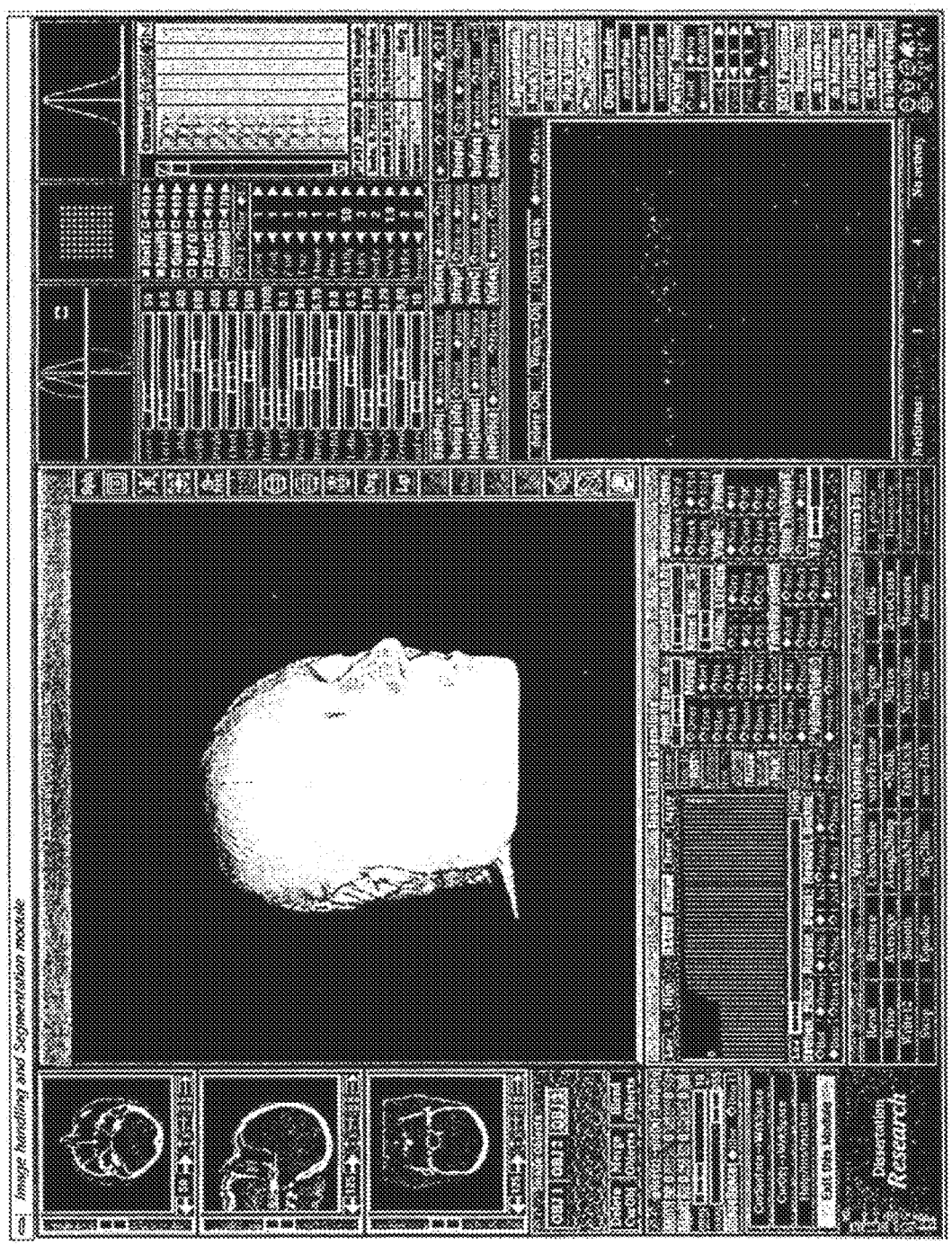
FIG. 11 illustrates a SOFM-based image segmentation and surface generation interface.
Figure 12A:
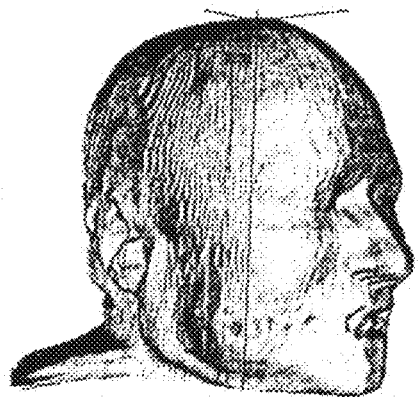
FIGS. 12A-12E illustrate a feature duster map, back projected pixels and triangulated surface rendering.
Figure 12B:
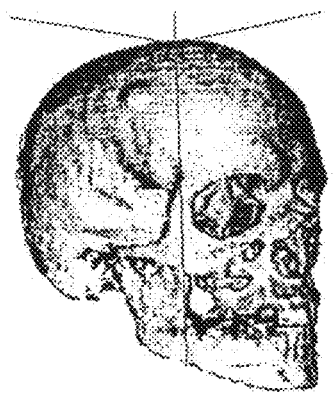
Figure 12C:
Figure 12D:
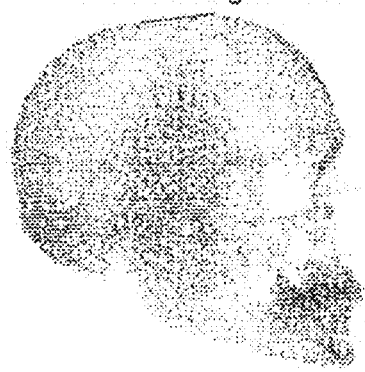
Figure 12E:
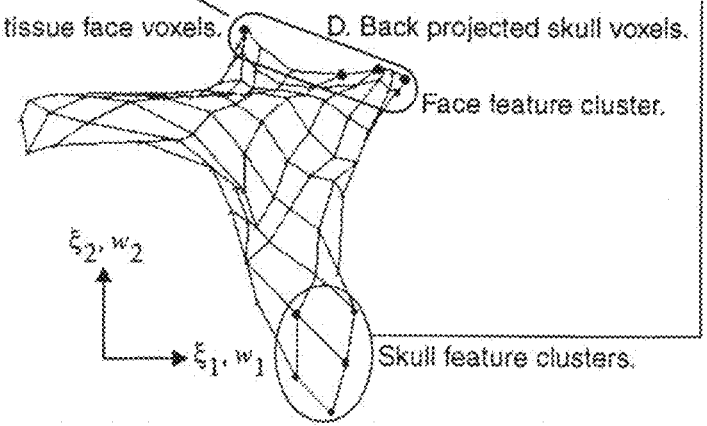

The 2D SOFM processor map displayed in the window (FIGS. 10, 11, and 12) allows the user to select voxel clusters associated with each processor. Clicking on a displayed node activates back projection of the associated voxels to a 3D graphics window. Successive feature clusters associated with desired surfaces may be accumulated, saved as a group, and back projected to the graphics display (FIG. 10). At this stage (i.e., selection of map nodes) no surface rendering is provided.

Our tests were with 3D head CT data. The voxel display of these data allows the user to quickly identify the processor nodes associated with skull, soft tissue face, oral, or cervical vertebral surfaces. After having identified the group of processors associated with the desired 3D surface, the voxels are triangulated for 3D surface rendering.

A. Self Organization (Ordering) Process

During the automated image segmentation process an ordering, from an initially random configuration of processors to a state of equilibrium of the self organizing feature map must occur. The weight vector of a processor is given by $W_{i,j}=[w_1, w_2, w_3, \ldots, w_6]$, where i=1, 2, . . . , I, j=1, 2, . . . , I, and I×I, is the number of processors assigned to the network configuration, where I ∈ {4 . . . 16}. A maximum of 256 processors were chosen, a condition which insures that the identity of a processor is always found in the range of 0 to 255. This allows each processor to be stored within one byte, thereby saving memory for further computation.

A VIDE is generated from each voxel in the input volume event space hash table and is sent to the processor layer. Once a processor captures a voxel, the cluster identity is placed back in the hash table register replacing the input voxel intensity cell datum. Later it will be displayed as part of a surface with all voxels belonging to this cluster. Voxel intensity information is obtained from the original input image volume via corresponding hash table registers. A processor's computed output is:

$$Q_{i,j} = \|\kappa F_n^n - W_{i,j}\| \qquad (12)$$

where $\xi = \kappa F_n^n$ is a VIDE vector, $n \in \{1 \ldots N\}$ and N is the total number of voxels. Among the processors a winner is identified. The distance measure $Q_{i,j}$ determines if it is lower than the initially chosen value. If so, the processor identity changes from its initial state; the new processor will continue to claim the voxel as long as no other processor claims it is the "winner." The winner successively strengthens its weight vector by a fraction of the input element values sampled by the $\alpha_{i,j}(t)$, a self excitation parameter. The value of $\alpha_{i,j}(t)$ is set and then decreased successively, eventually resulting in no change to the weight vector. This ensures that the network will reach an equilibrium. Another parameter, $\beta_{i,j}(t)$, influences neighborhood processor excitation and determines how much the winner can excite or inhibit its neighbor's weights. $\beta_{i,j}(t)$ is assigned a fixed value that decreases over time to avoid wide fluctuations in the organization process. Using neighborhood Gaussian function curves (See FIG. 3), defined by the parameter $\gamma_{i,j}$, the number of neighboring processors is successively decreased. This number is initialized with a default value at the beginning. The "winner" processor takes the current input voxel to its cluster along with its spatial coordinates. This update replaces the processor's identity, id $\in \{0 \ldots 255\}$, with the voxel density currently in the register.

Figure 13A:
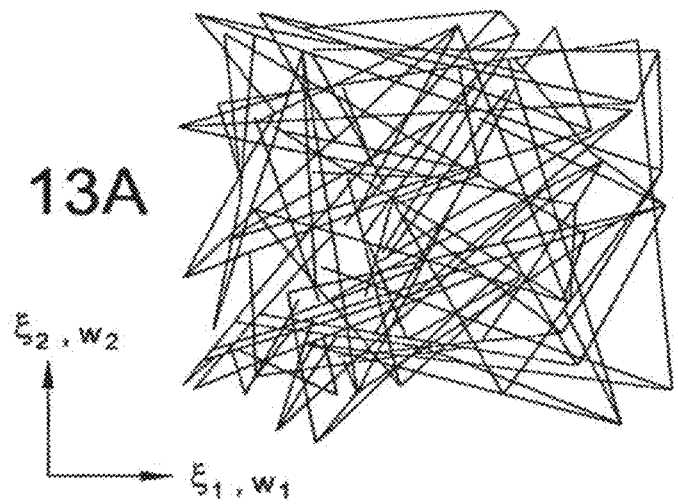
FIGS. 13A and 13B illustrates a self organizing feature map formation process in which an initial random processor location evolves into the intended grid-like structure as ordering is obtained by the neural network.

Prior to the mapping process the weight vectors, $W_{i,j}$ of each processor, are initialized with random values. Therefore, the initial topology of the axis spanned by connection strength between any two of the VIDE elements is unorganized. This is shown in FIG. 13A. The processor's physical connections remain constant throughout the process, processor 1's connections to processor 2 remain the same). However, the mapping topology with respect to each processor's connection strength changes throughout this process. The random starting topology, shown in FIG. 13A, is drawn by plotting each processor's weight vector, chosen two weight elements at a time, onto two dimensional axes. The initial pattern has no meaning, however the final pattern obtained presents processors (feature clusters) containing voxels representing 3D surfaces and similar 3D surfaces will be shown in the same SOFM map region. We have chosen voxel intensity and Euclidean distance and their corresponding members in processor weight vectors to plot the map topology in FIGS. 13, 10, and 11.

Figure 13B:
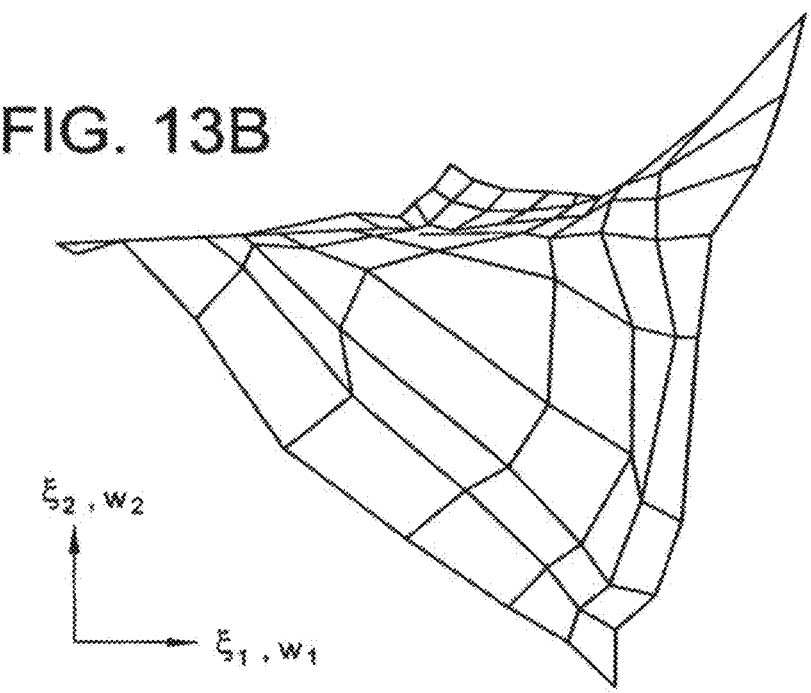

After N input VIDEs are fed through the input layer, producing each processor's final weight vector, the network adopts, approximately, the original "flattened" processor grid topology. The axis of the grid is spanned by processor connection strength values. This grid is a 2D projection image of the feature cluster VIDE hyperspace. An example is seen in FIG. 13B.

SOFM feature vector adaptation results from two basic mechanisms: (1) identifying a "winner" and allowing it to modify it's connection strengths; (2) allowing the winner to selectively excite/inhibit its neighbors. The first mechanism ensures connection strengths that reflect input event values. The second mechanism ensures that related processors, especially those representing anatomical surfaces, are mapped adjacently. The observed surfaces, displayed as point clusters from a set of neighboring processor nodes, illustrate the second mechanism in FIG. 10.

The voxels associated with the winners are clustered and classified as separate groups. These clusters are identified through the processor's identity, a unique value which is stored in the hash table during the self organization process. The resulting clusters capture continuous anatomical surfaces [FIG. 10] that exist in the 3D image volume as an intrinsic model of the VIDE event space. This approach differs from physically based models (prior information) or user-defined (algorithm assisted or manual selection) segmentation methods that rely on information extrinsic to the image volume. Our method adaptively locates surfaces captured in the image volume using voxel data intrinsic to the image volume. We involve the user to verify and determine the surface identity. This introduces supervised learning to the unsupervised neural network algorithm.

B. Surface Rendering

Two different types of surface rendering methods (i.e., triangulation of voxels associated with selected feature clusters) have been implemented. The first approach is primarily a contouring of the outermost voxels. Assuming the volume contains a thin boundary surface, all cells on the surface are classified as useful vertices. Each slice is divided into four quadrants, and each quadrant is swept by 256 lines from it's outer most volume boundary to the slice image centroid. In each ray, the first encounter with the boundary surface is defined as a boundary vertex. The remaining sweeps obtain subsequent vertices in each slice, resulting in a closed curve that traverses all of the detected slice vertices. Since the fine sweeps are produced at half degree angular rotation intervals, the points generated are aligned in the correct neighborhood. Next, four sided polygons are generated from all quadruples of neighboring vertices in a pair of consecutive closed curves. These polygons are degenerated to two triangular faces. This results in a complete triangulated surface of the segmented image object. This procedure is extremely fast and well suited to display simple surfaces such as the soft tissue face (see FIG. 12A). However, views of objects with complex topology, such as the skull, provide unsatisfactory results.

A second approach is taken to rendering complex surfaces such as the skull. We used a known method of decomposing volumetric data into tetrahedra. This approach takes two adjacent slices and traverses neighboring voxels eight at a time, treating them as a tetrahedron. The decomposition of tetrahedra produces the oriented cycles necessary to represent triangular faces of an isosurface. This approach yields, for example, a skull surface (see FIG. 12B). We also compared the Doi and Koide tetrahedral decomposition to the marching cubes algorithm. Both algorithms use bi-linear interpolation to compute partial voxel values. Computation of a complete skull surface rendering, took approximately 3 to 4 minutes as opposed to 2 to 3 minutes, on an SGI Octane workstation.

C. Combining Multiple Surfaces and Filling Holes

The user can combine the feature clusters associated with multiple SOFM processors. If unexpected holes are seen in the surface, perhaps due to partial voluming "drop out" of thin structures, the volume image region immediately around the missing area may be selected as a new region of interest (ROI). A new high resolution processor map of voxel clusters is generated for this zoomed-in ROI, allowing careful surface assembly in regions of thin bone or skin.

D. Partial Volume Error

Figure 14:
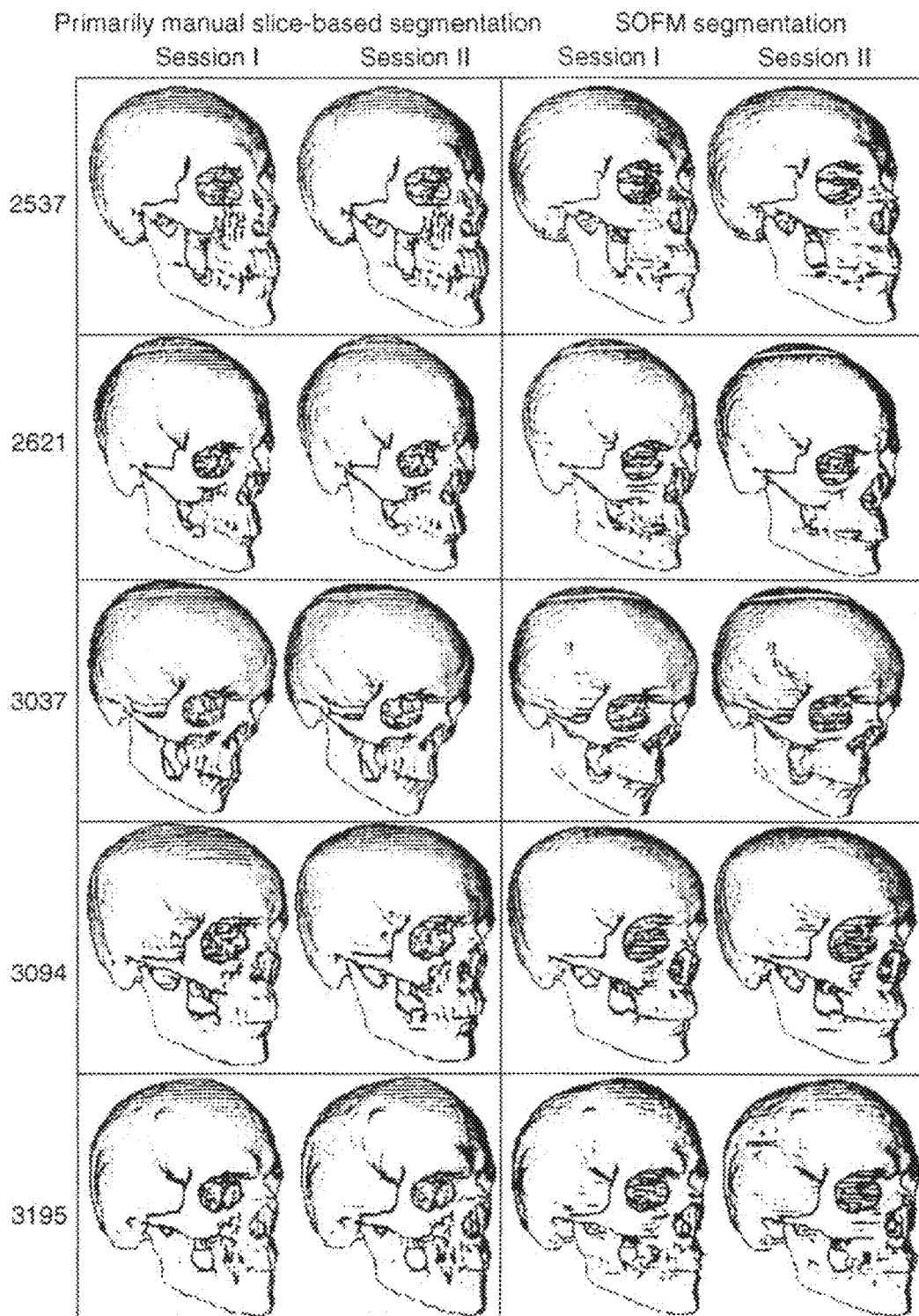
FIG. 14 illustrates both sessions of manual and SOFM segmented surfaces for skull surfaces.

This error results in surface "drop out" and is a well known cause of surface inaccuracy in 3D CT visualization of thin bone segments. The problem becomes more difficult where bone voxel intensities are reduced to tissue levels. Region growing and manual intensity thresholding techniques for isosurface generation cannot overcome these errors. We find that selecting a region presenting thin bone segments and assigning higher preferences to VIDEs 5 and 6 (i.e., Laplacian zero crossing and Invariant image moments) allows of local SOFM map to capture more of the desired voxels representing surfaces formed by thin bone. For example, the computationally expensive moment invariant was set at 10 weighting on this initial pass, then elevated to 40-60% in user-defined regions around thin bone structures such as the infra-orbital foramina and orbital walls (FIG. 14).

4. SOFM Precision Tests and Results

The SOFM program was tested with five 3D CT data sets (B2537, B2621, B3037, B3095, B3195) provided by a recall of subjects. All subjects are above 60 years in age, female, have dental fillings, and often have large oral prostheses (dentures). One operator (AM) segmented all the images twice by two methods; (1) slice-based methods intensity thresholding, manual pixel selection, and 2D and 3D region growing) in the AUTO program, and (2) Self Organizing Feature Map. Both the slice-based and SOFM tools provide orthogonally reformatted views of the original image and segmented pixels. More than a day passed between each segmentation session. Intra-operator variance (precision), using either segmentation method, was measured between the two segmentation attempts. In manual segmentation, skull and soft tissue face segmentations were separate activities. In SOFM experiments, the same ordered map was used to produce the skull and soft tissue surfaces in a single attempt.

The original, unsegmented CT data sets are 512×512×115 in dimension with 1.904 mm slice thickness and 0.5 mm pixel resolution. This scan protocol was chosen to provide accurate source data for boney skull and soft tissue face isosurface images. This data was reduced to 256×256×115 in dimension with 1.904 mm slice thickness and 1 mm pixel resolution. This resolution is sufficient in terms of the resulting surface segmentation and saves memory resources on the computer.

Five measures were used to determine both intra-operator within-method variance and between-method variance in the resulting segmented images. The former measures how reproducible the segmentation is; low variance implies high precision. The latter measures how different the results of the two methods are. We expect the differences to be local to regions of thin structures or metallic artifact where qualitative inspection suggests the greatest benefit from SOFM segmentation. These five measures are: (1) Visual comparison of the skull and soft tissue face surfaces obtained; (2) Difference of the overall volume of the segmented image; (3) Two dimensional difference images computed slice by slice for each slice image within the volume; (4) Three dimensional difference images viewed from three orthogonal eye points; and (5) Procrustes superimposition of manually located, highly reliable, single point anatomical landmarks. The last measure is similar to a qualitative visual determination of the completeness of anatomical features seen on the segmented surface. Clearer features will result in more easily, and more repeatably, detected anatomical landmark coordinates by trained workers.

Figure 15:
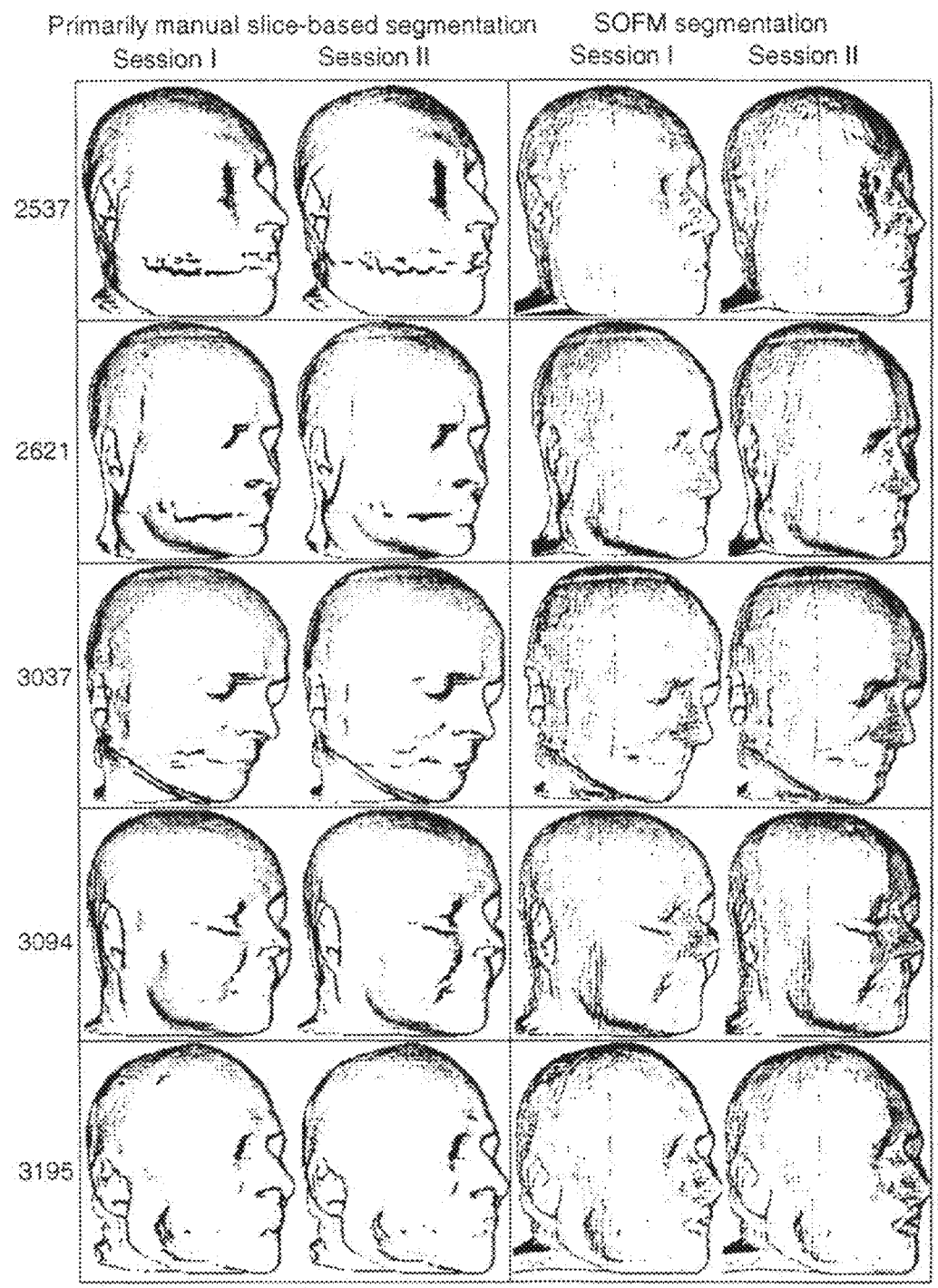
FIG. 15 illustrates both sessions of manual and SOFM segmented surfaces for soft tissue face surfaces.

A. Test 1: Visual Comparisons:

The left hand side of FIGS. 14 and 15 show both manual slice-based segmentation attempts. The right hand side shows both SOFM segmentation results. SOFM segmentation of soft tissue face recovers thin tissue structures around the nostrils, lips, and ears, producing an improved image. There is also dramatic improvement in reducing the effect of the metallic (dental filling) artifact around the lips. Note the variable posterior sagging of inframandibular soft tissue due to the affects of gravity on the supine individual within the head holder. SOFM skull segmentation (FIG. 14) improves areas of thin bone around the infraorbital and mental foramina and the thin posterior and medial orbital walls. These visual results indicate that the slice-based segmentation does not allow as effective a search for these surfaces.

B. Test 2: Volume Differences:

Table II presents volumetric differences between the soft tissue face obtained between an average of multiple attempts and each attempt in both manual and SOFM methods and between the two method averages. Table III presents the same data for the segmented skull image volumes. The difference image volumes were computed by multiplying the total number of voxels in each segmented image by voxel volume (1.904 mm3). SOFM segmentation results show less difference between sessions. Given the additional detail it is not surprising that in comparison with manual slice-based segmentation. SOFM segmentation results m an average of 3.9% more volume for skull segmentation and 0.5% more for soft tissue face segmentation. The higher difference for skull segmentation likely indicates greater reduction of partial volume error.

Figure 16A:
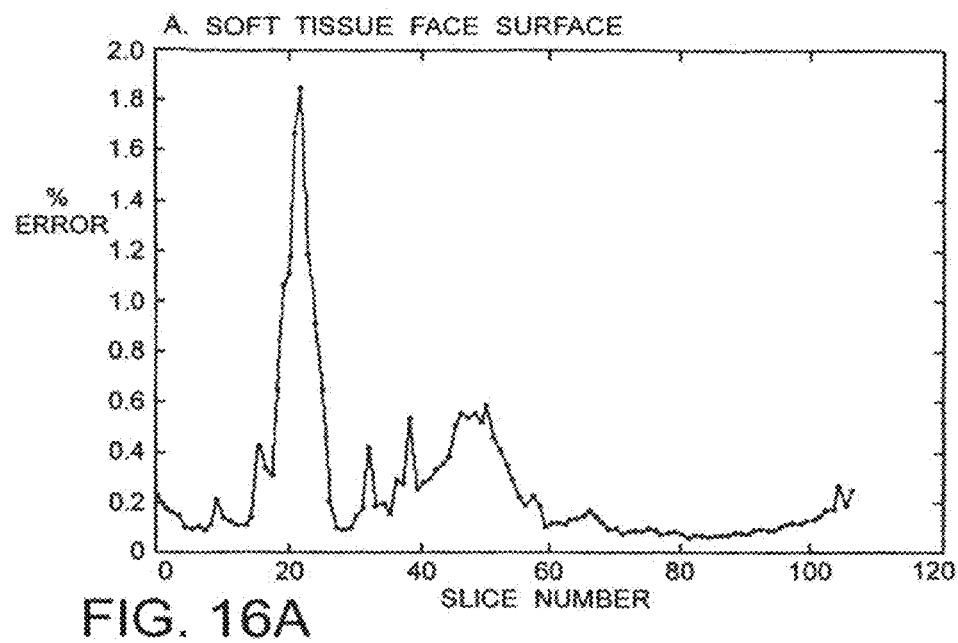
FIGS. 16A and 16B illustrate plots of accumulated differences across all five data sets per slice the soft tissue face surface and the skull surface, respectively.
Figure 16B:
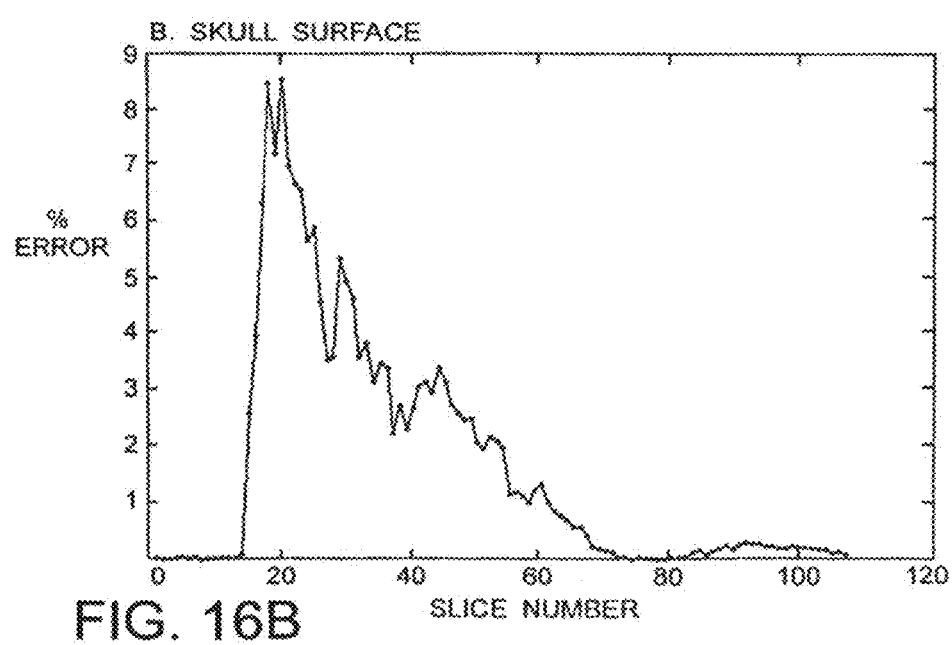

Test 3: 2D Slice Image Difference Data:

This test presents 2D slice by slice difference profiles for each image volume using either segmentation method. These difference profiles result from calculating the absolute difference between corresponding pixels in the homologous segmented slices. The accumulated difference across all five data sets are plotted per slice in FIG. 16A for the soft tissue fact surface and FIG. 16B for the skull surface. Regions where the slices contain thin bone and dental filling artifact require manual pixel selection during manual slice-based segmentation in AUTO. These are areas where the user must make many decisions that are not well replicated on subsequent segmentation attempts. Manual slice-based segmentation results in higher intra-operator variability. Regions with thin, soft tissue or bone, or dental artifact, contributed most to the difference plots (FIG. 16) between the slice-based manual and SOFM segmentation results, this suggests that the latter was more the reliable method.

Figure 17:
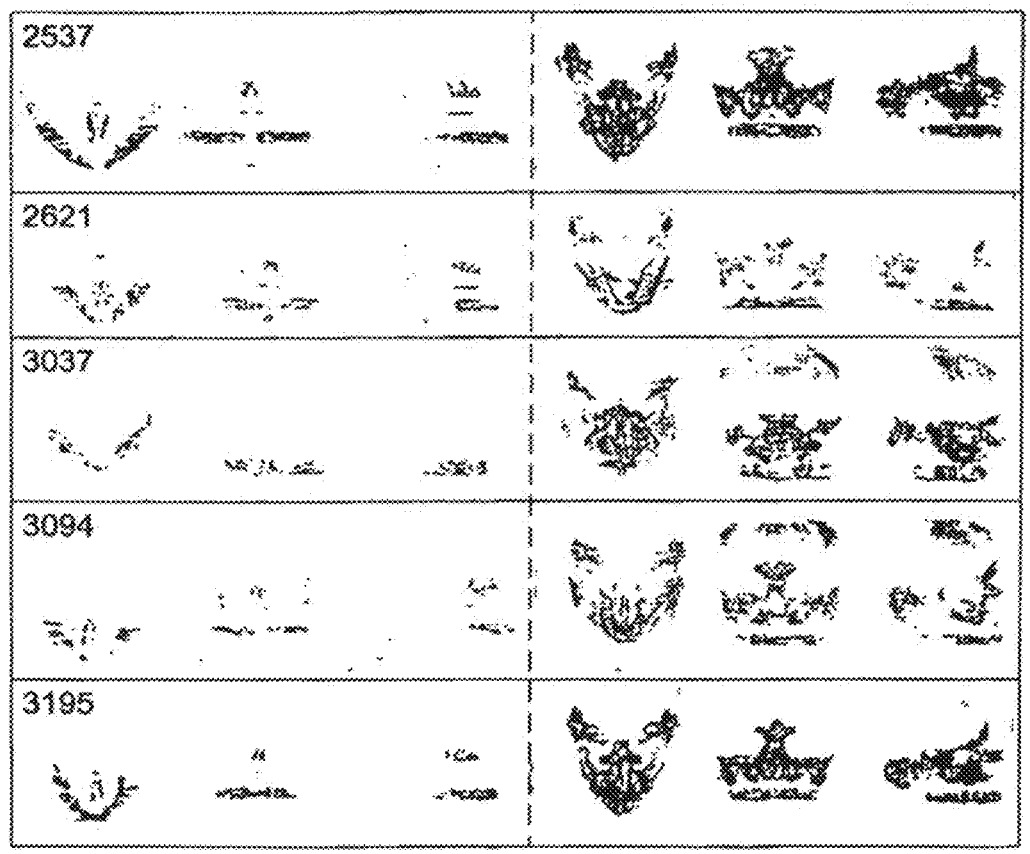
FIG. 17 illustrates orthogonal projections of 2D images.

D. Test 4: 3D Difference Images:

This test consists of 3D difference images computed between the volume image resulting from the two segmentation methods. The 3D difference images, seen in three orthogonal projections of 2D images in FIG. 17, graphically illustrate the affect of highly variable human decision making in the regions of metallic artifact and thin structures during manual slice-based segmentation. Note that thin areas of the skull surround the pneumatic sinuses (i.e., frontal, maxillary, ethmoid, sphenoid, and mastoid). Areas of thin soft tissue face structures (especially, the nostrils, eyelids, ears, and lips) are more fully extracted by SOFM than with slice-based manual methods.

E. Test 5: Anatomic Landmark Localization:

The user was asked to pick reliable anatomic landmarks twice on the soft tissue face and skull surface segmented either manually or by SOFM. These landmarks include 21 on the soft tissue face surface (Table IV) and 26 on the skull surface (Table V). The error found between landmark locations in these two sessions was determined via Procrustes fit. The error reported here is the average value across all 5 superimpositions. We contend that the improved quality of the imaged surface, especially in areas of artifact or thin structures, reduces intra-operator variance (i.e., raises precision) between landmarks picked on two attempts of either the soft tissue face or skull surfaces segmented via the SOFM method; the less ambiguous SOFM surface renderings allow our skilled operator to place these landmarks more precisely.

F. Time of Segmentation:

Skull and soft tissue face segmentation sessions (AM) were reduced from approximately 3 to approximately 0.5 hours. In either method, the majority of time is spent correcting dental artifact or partial volume error. We are aware that the skull is most often segmented at the CT console by intensity thresholding alone. This method may save time but results in the poor segmentation of thin structures or those near metallic artifact.

II. Warping

As described below, the step G of warping the template to an external surface of a normative shape of the bone of interest is preferably executed using a Simulated Annealing-based Surface Extraction (SASE) process.

In order to save time, improve precision (repeatability), and increase accuracy of the extracted anatomical surface, a ridge-curved based deformable template superimposition strategy combines simulated annealing of a ridge and tiling curve wireframe and subsequent surface normal based identification of surface tile points. The annealing algorithm searches the volume image and displays the result to the operator on a graphical manifold rendering of the surface of interest. Unlike energy minimization algorithms, which require a good initial parameter estimation to avoid converging to a misleading local minimum, annealing methods exploit stochastic search methods to locate a global minimum. Several stochastic methods form a basis for simulated annealing. Space curve fitting of 3D surfaces is a goal not uncommon in the field of computer vision. It is merely object recognition followed by shape registration.

B-spline space curve encoding of labeled surfaces has application beyond surface averaging and craniometrics or image co-registration. We seek highly accurate surface extractions to model cranial prosthetic implants for the skull. Homology mapped, B-spline space curve encoded surfaces prove useful in morphometric, biomechanical, and deformable model assessment of many organ systems. Additionally, parameterized surface extractions, especially of the external body surfaces, have application in animation.

1. Ridge Curve-Based Deformable Template Creating

Figure 18:
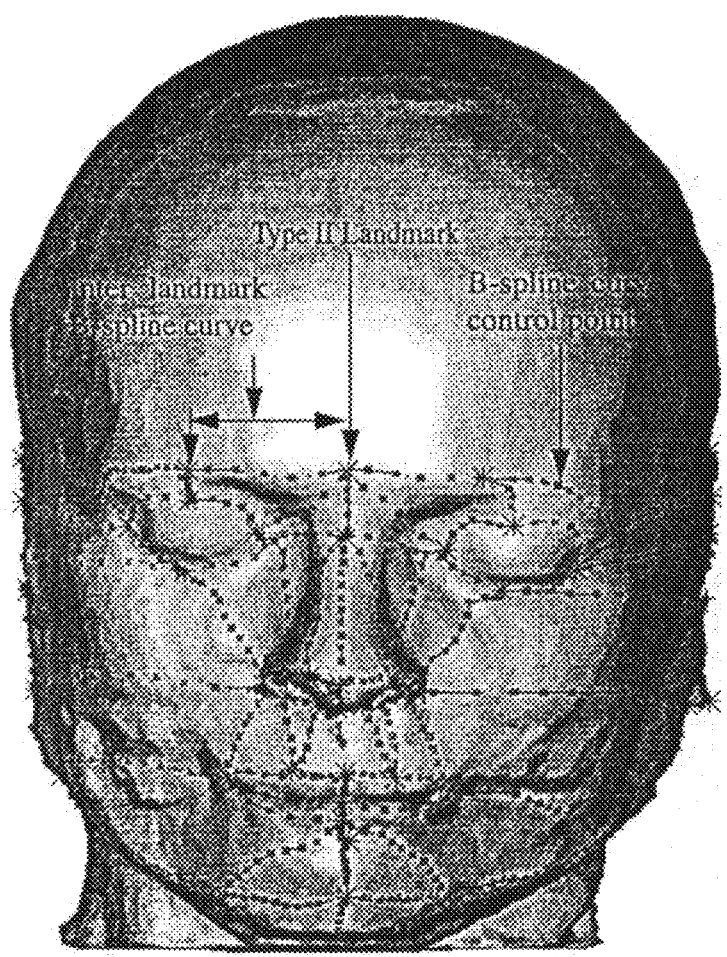
FIG. 18 illustrates a new ridge curve-based deformable template wireframes superimposed on a soft tissue face graphical manifold, with Type II landmarks, ridge curve arcs, and tiling curves indicated.

We chose to use B-spline surface encoding because it provides a smooth surface approximation, reduced data set, and easier assignment of labels to various components (see Appendix 2 for B-spline curve and surface construction). We have re-implemented skull and soft tissue face ridge curve-based deformable templates in this fashion. FIG. 18 shows one of these new ridge curve-based deformable template wireframes superimposed on a soft tissue face graphical manifold, with Type II landmarks, ridge curve arcs, and tiling curves indicated.

Tiling Curves:

Since ridge curves rarely intersect, additional space curves are necessary to tile the surface with a single enclosing wireframe. In order to identify a unique demarcating line within a search space we define tiling curves as space curves that: (a) traverse a low curvature area (i.e., flat surface), and (b) are weighted to pass close to a plane passing through the surface between the tiling curve end points and the center of mass of the entire image surface (See Sections II.2.C and II.2.G).

Initially, we approximate tiling curves as straight lines between endpoint landmarks. In FIG. 18, B-spline ridge and tiling curves are indicated by dotted lines while their control points are shown as small black cross-hatches. The Type II landmarks are shown as large black cross-hatches.

As one draws either a ridge or tiling curve, a corresponding 8-spline curve is fit to the surface via global curve interpolation to a set of control points sampled from the user drawn space curve. The B-spline interpolated 3D points collected are re-sampled and indexed to vertices on the graphical manifold surface and assigned a control point vector, $P_i$. In the case of ridge curves, our resampling maintains the curvature information along ridge curves when determining how to space the control points. On the other hand, tiling curve control points are equi-distantly spaced. The curve smoothness, set by the operator, further determines redistribution of control points, if necessary. Knot-vectors and knotspacing require a B-spline interpolation function assignment for each space curve, by the operator during the template creation process.

FIGS. 19A and 19B display the Type II landmarks and Appendix 1A and 1B list the non-landmark components of the soft tissue face and boney skull templates, respectively. The soft tissue face template consists of 56 Type II landmarks, 103 space curves (54 ridge curves and 49 tiling curves), and 44 surface tiles [FIG. 19A, Table VI]. The skull template consists of 54 Type II landmarks, 104 space curves (40 ridge curves and 64 tiling curves), and 47 surface tiles [FIG. 19B, Table VII].

2. Ride Curve-Based Deformable Template Superimposition

A. Graphical Surface and Volume Image Input:

The 3D surface input we use results from segmented volume images. The segmented voxels are rendered as a graphical manifold. Segmentation occurs via an unsupervised neural network program. The graphical manifold is built with sub-sampled voxels to provide an interactive context to the operator.

The simulated annealing ridge curve-based deformable template superimposition algorithm evaluates features found in the volume image, not on the graphical manifold surface. The unsubsampled volume image provides additional cues for best locating ridge or tiling curves. The result of the search is displayed on the graphical manifold surface where the operator can make manual corrections to algorithmic insufficiencies. The CT slice shown in FIG. 20A highlights the segmented surface voxels of interest which are indexed to the vertices (points) in the adjacent rendered manifold surface (FIG. 20B).

During loading of the graphical manifold surface data, a 3D lookup table (i.e., geometric hash-table) of spatial x,y,z and curvature metrics (Listed in Table 8) corresponding to each vertex is generated. This provides the simulated annealing based surface extraction complete indexing between the rendered graphical manifold and the source volume image.

Figure 21A:
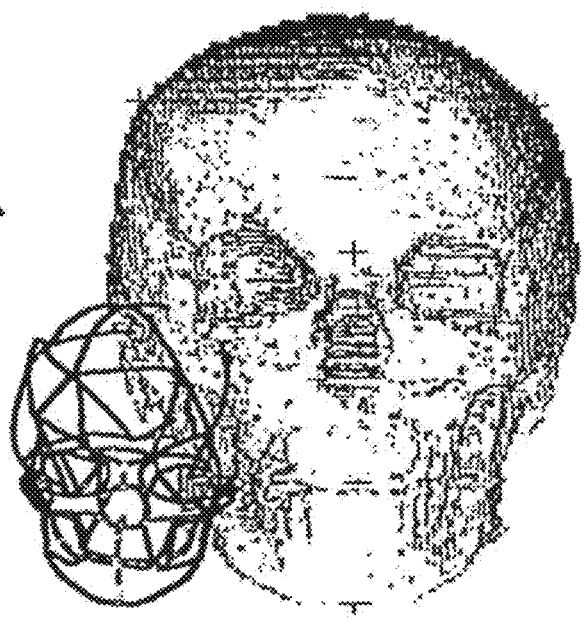
FIGS. 21A and 21B illustrate a candidate wireframe prior to the warp at lower left and the result of the thin plate spline warp of the wireframe onto the Type II landmarks, respectively.
Figure 21B:
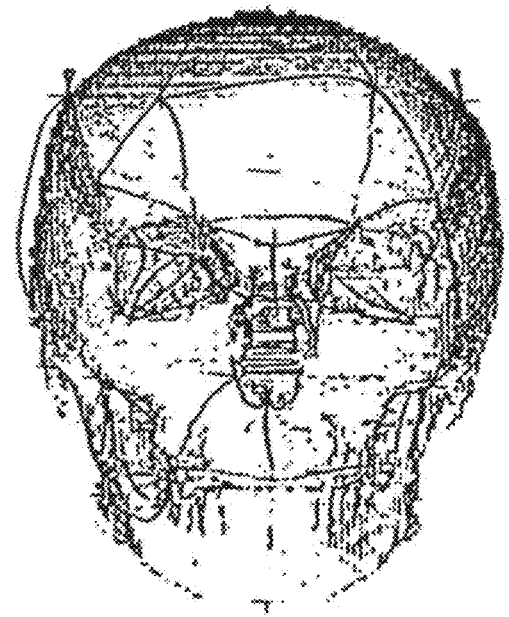

B. Candidate Wireframe:

The first step in the Simulated Annealing-based Surface Extraction (SASE) process is the operator's manual location of the Type II landmarks on the graphical manifold surface. These landmarks attach the ridge curve-based deformable template to the graphical manifold surface via a thin plate spline warp. FIG. 21A shows a candidate wireframe prior to the warp at lower left. FIG. 21B shows the result of the thin plate spline warp of the wireframe onto the Type II landmarks. Some of the landmarks (large cross-hatches) are visible. Note how the candidate wireframe undulates in and out of the surface.

C. Volume Image Features:

Simultaneous to loading of the graphical manifold data and lookup table generation, a set of surface geometry features are generated for use in the simulated annealing procedures. A method is known for computing principal directions and principal curvature values (FIG. 22) for any point on the segmented image surface directly from the input volume image data. In addition, the principal normal and tangent vectors are derived at the same time. These latter parameters, in addition to providing the basis for the simulated annealing process cost functions, are also used to bound the search space in the volume image linked to the graphical manifold surface displayed for the operator.

The search for volume image principal curvature normal vectors and principal curvature tangent vectors occurs initially at a point, I, a control point found on the B-spline space curve, defined at location $\{x_0,y_0,z_0\}$ to have normal vector $\tilde{N}$ on the volume image surface s defined as $I(x,y,z)=I(x_0, y_0,z_0)$. I lies m the same direction as the curvature gradient (i.e., changing surface normals) of the surface voxel data:

$$\nabla I=(I_x,I_y,I_z)|(\tilde{N}=(\nabla I)/\|\nabla I\|) \quad \text{(EQ 13)}$$

Figure 22A:
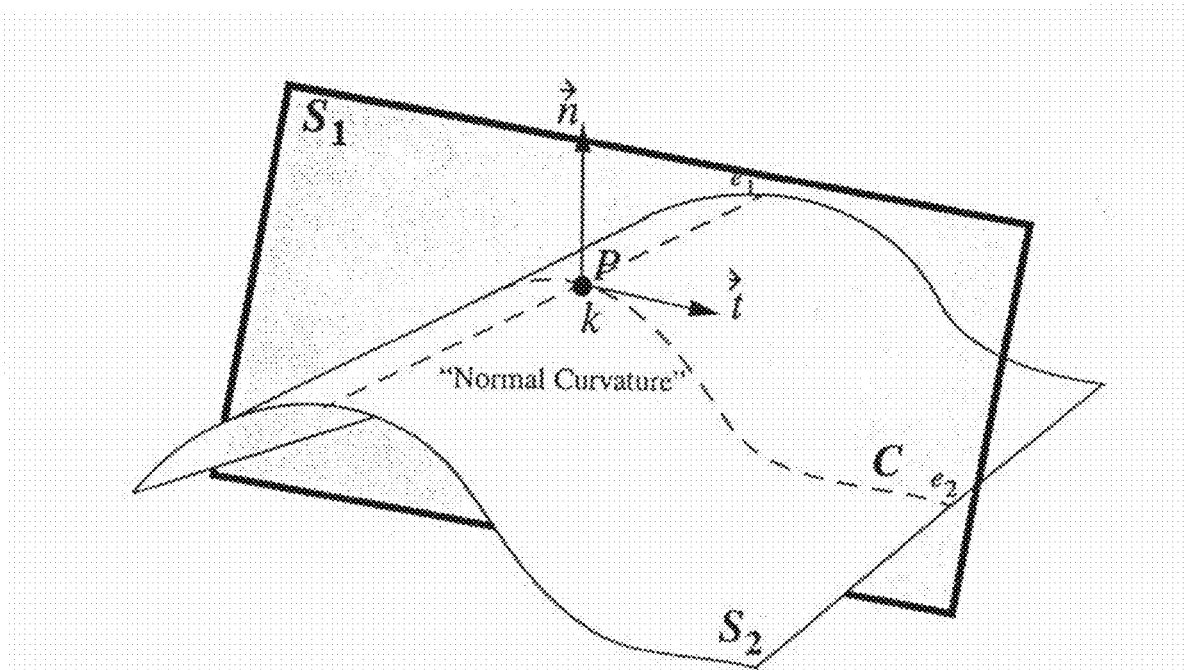
FIG. 22A illustrates a space curve c from a sweeping plane positioned at each control point, with tangent vector $\bar{t}$, along a normal section of segmented voxel surface s.
Figure 22B:
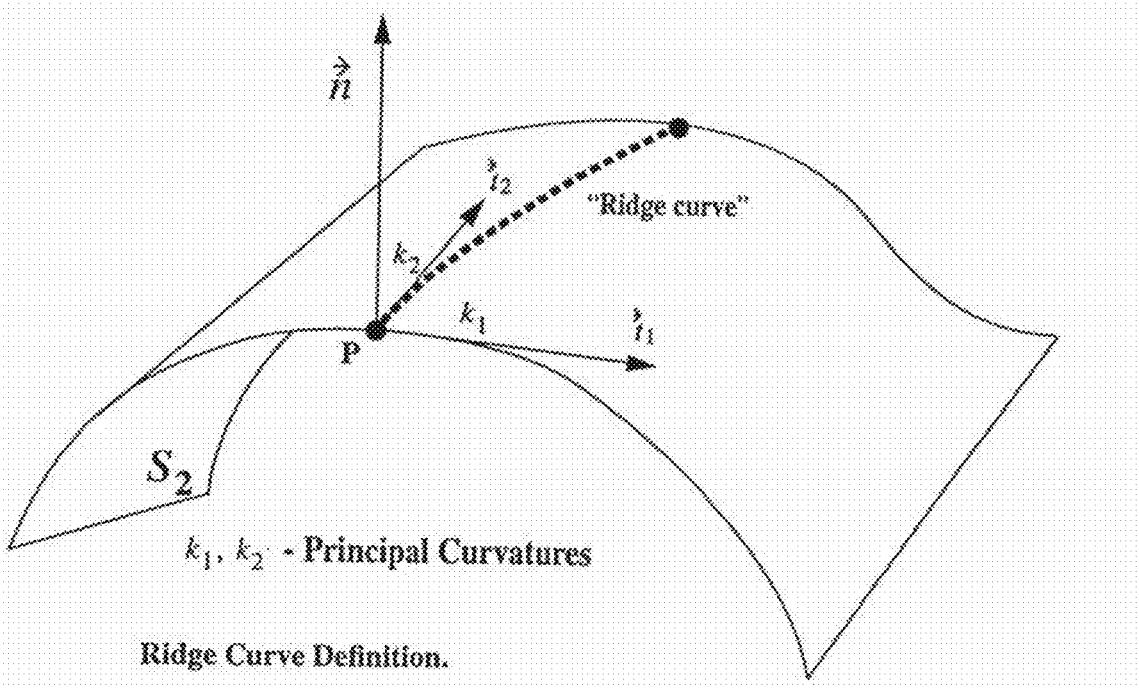
FIG. 22B illustrates a surface normal curvature $k''_n$ in direction $\bar{t}$ where $k_n$ attains principal curvature values $k_1$ and $k_2$.

In order to evaluate the local surface curvature we consider a space curve c from a sweeping plane positioned at each control point, with tangent vector $\bar{t}$, along a normal section of segmented voxel surface s (FIG. 22A). The normal vector at any point along c is $N=(n_x,n_y,n_z)$. Differentiation of $\nabla Iy=0$ yields surface normal curvature $k_n$ in direction $\bar{t}$, where $k_n$ attains principal curvature values $k_1$ and $k_2$. Principal directions $\bar{e}_1$ and $\bar{e}_2$ show the path of the principal curvatures (FIG. 22B).

On any surface, the local curvatures vary between the principal curvatures $k_1$ and $k_2$. Therefore, the curvature parameters we use combine these measures:

$$K=k_1 \cdot k_2 \quad \text{(EQ 14)}$$

$$M=\tfrac{1}{2}(k_1+k_2) \quad \text{(EQ 15)}$$

where K is Gaussian curvature, independent of principal directions and M is mean curvature changes sign with opposing principal directions.

Twelve feature dimensions are used for simulated annealing registration of ridge or tiling curves (Table VIII). The 3rd order image derivatives are obtained from image derivatives:

$$H = \begin{bmatrix} I_{xx} & I_{xy} & I_{xz} \\ I_{yz} & I_{yy} & I_{yz} \\ I_{zx} & I_{zy} & I_{zz} \end{bmatrix} \quad \text{(EQ 16)}$$

The Partial derivatives of H along each axis are $H_x, H_y, H_z$:

$$H_x = \begin{bmatrix} I_{xxx} & I_{xyz} & I_{xzx} \\ I_{yzx} & I_{yyx} & I_{yzx} \\ I_{zxx} & I_{xyx} & I_{zzx} \end{bmatrix}, \quad \text{(EQ 17)}$$

$$H_y = \begin{bmatrix} I_{xxy} & I_{xyy} & I_{zxy} \\ I_{yxy} & I_{yyy} & I_{yzy} \\ I_{zxy} & I_{zyy} & I_{zxy} \end{bmatrix},$$

$$H_z = \begin{bmatrix} I_{xxz} & I_{xyz} & I_{xzz} \\ I_{yxz} & I_{yyz} & I_{yzz} \\ I_{zzz} & I_{xyz} & I_{zzz} \end{bmatrix}$$

Among, these 27 third order partial derivatives, ten derivatives are chosen, $I_{zxs}, I_{xxy}, I_{xsx}, I_{syy}, I_{xyz}, I_{xsz}, I_{yyy}, I_{yxs}, I_{ysz}, I_{zxx}$, preferring derivatives along the three axes. Essentially, the maxima of these ten third order partial derivatives provide an indication of sharp geometric transition. A predetermined inter-knot spacing restricts any overlap of search space between any two control points. The Type II landmarks are used for ridge curve arc-separation and to anchor tiling curves.

Features for Ridge Curve Arcs:

We use Gaussian and mean curvatures, and ten third order partial image derivatives to obtain maximum curvature prescribing control points along the surface between ridge curve arc endpoints (i.e., Type II landmarks).

Figure 23A:
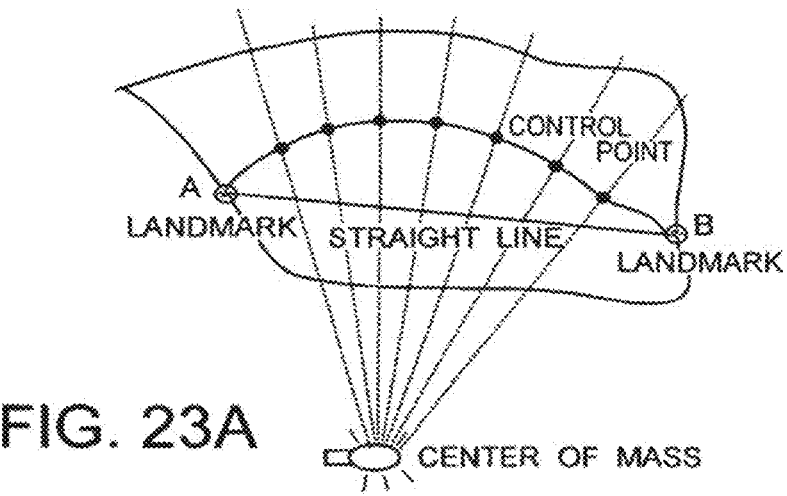
FIGS. 23A and 23B illustrate a plane constructed from the two endpoint landmarks and an object's center of mass.
Figure 23B:
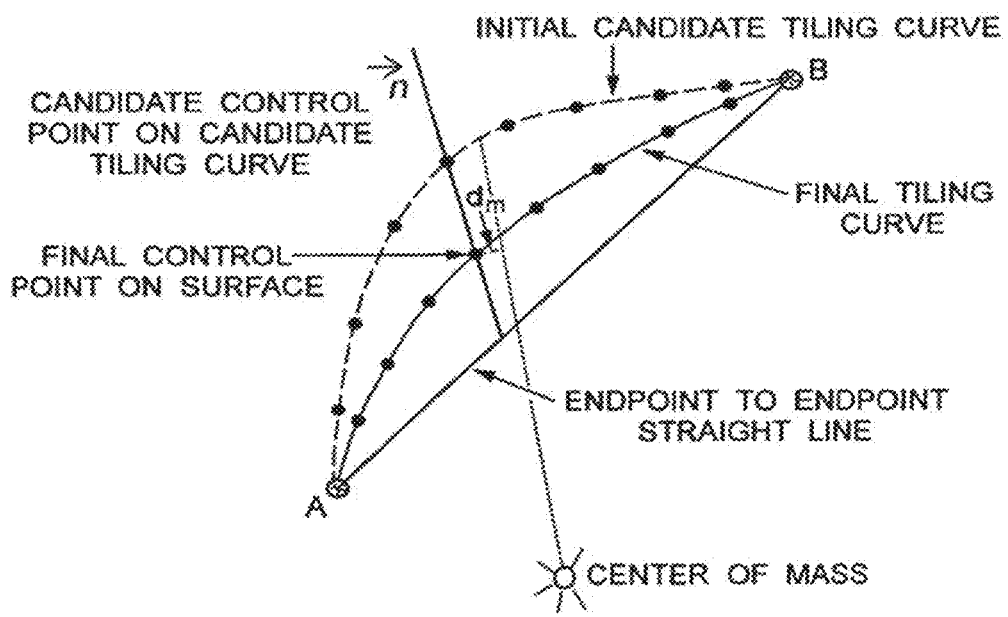

Features for Tiling Curves:

We use the same set of features to position tiling curve control points along lines of minimum curvature. In addition, we use a thirteenth feature, a deviation measure, $d_m$. It is found between the candidate control point normal and the nearest ray within a plane constructed from the two endpoint landmarks and the object's center of mass (FIG. 23). The deviation measure helps limit the tiling curve search space so that no boundaries overlap.

Figure 24:
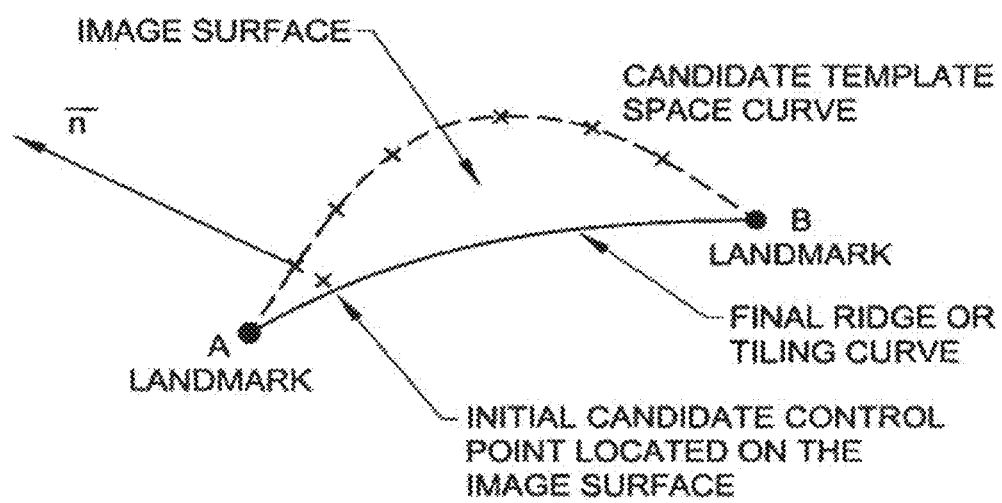
FIG. 24 illustrates a trace along the candidate template's control point to the image surface.

D. Initial Control Point Location:

When the template is warped to operator located landmarks on a patient image the candidate space curves connecting the Type II landmarks and their control points may not lie on the image surface. The true surface is located using a trace along the candidate control point normal. Thus, the initial candidate control point is assured to be on the image surface. FIG. 24 illustrates a trace along the candidate template's control point to the image surface. The annealing process starts with the first point found on the surface as an initial candidate control point.

Figure 25A:
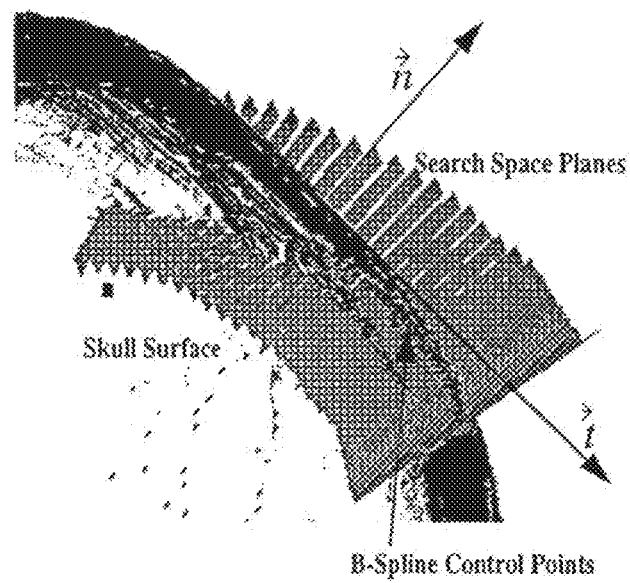
FIG. 25A illustrates a cross section on the top of the skull and tiling curve control point search planes intersecting that image surface.
Figure 25B:
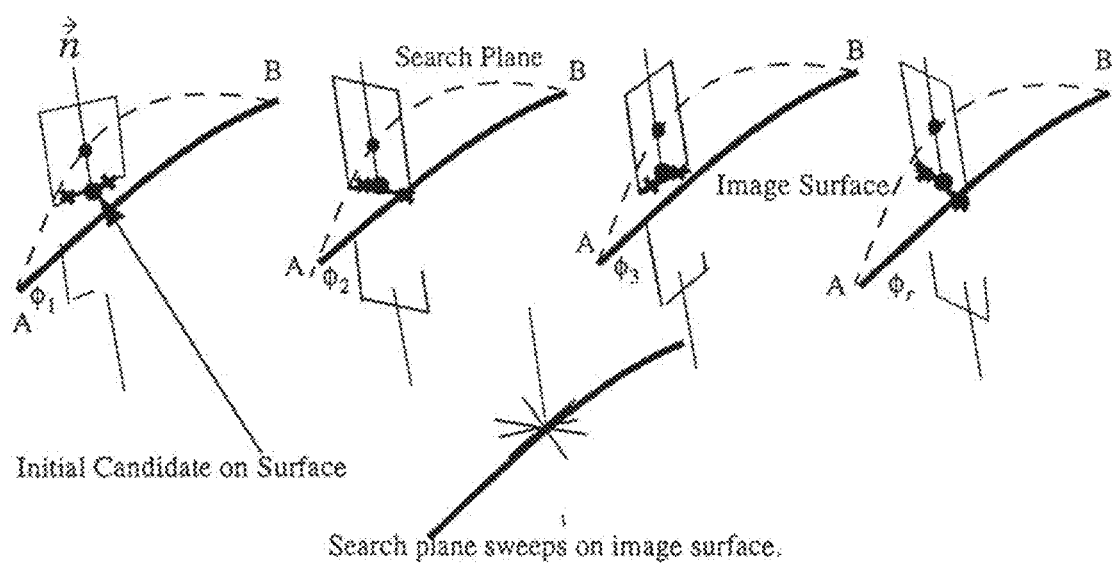
FIG. 25B illustrates a series of search plane iterations.

E. Search Plane:

A search plane is anchored to the candidate wireframe (i.e., ridge curve-based deformable template) and rotates about the axis of that point's surface normal in the volume image. Note that when ridge or tiling curves sit on a two sided tile boundary, these cut planes rotate a full 360 degrees (FIG. 25B). The sweep rotation about each control point normal is set to increment a default 45 degrees (operator chooses between 10 and 90 degrees). If search in one direction fails, an opposite direction search is attempted. This is important where a ridge arc is at the surface margin.

F. Random Candidate Control Point Generation:

The principal directions constrain the search space for each control point along the B-spline space curves. The maximum principal curvature bounds the space in which it is profitable to search for optimal B-spline space curve control points. The search space for each B-spline control point during ridge curve or tiling curve superimposition is defined from the point normals and tangents bounded by the principal directions. FIG. 25A shows a cross section on the top of the skull and tiling curve control point search planes intersecting that image surface. FIG. 25B shows a series of search plane iterations.

Candidate control points are evaluated during each search plane iteration. Search plane rotations select a randomly located set of M (chosen by operator, default is 2) candidate control points for k search iterations. Random candidate positions are selected from the space curves intersected by the search plane rotations through the image surface. Their features (Table VIII) are computed and evaluated by the cost function in comparison to the current candidate control point position, $\zeta$. The actual candidate locations on the image surface chosen for evaluation via variables r and s using reflection coefficient parameter $\alpha$:

$$r = \left(\frac{\alpha}{N\sqrt{2}}\right) \cdot \left(\sqrt{(N+1)} + N - 1.0\right) \quad \text{(EQ 18)}$$

$$s = \left(\frac{\alpha}{N\sqrt{2}}\right) \cdot \left(\sqrt{(N+1)} - 1.0\right) \quad \text{(EQ 19)}$$

where N is the number of dimensions (i.e., number of image features in the case presented). Randomly distributed position vectors ($I_p$) are computed by using r and s as:

$$Ip = S(h \cdot \text{rand}(r), w \cdot \text{rand}(s)) \quad \text{(EQ 20)}$$

where S is the search space spanned by width, w, and height, h, computed from the normal and tangent at the template B-spline space curve control point. The rand(r),rand(s) are the coordinates with the search plane. Each position within the search space plane carries a single vector for the three coordinate axes, which is indexed to a segmented surface voxel in the volume image space.

The probable distribution of positions are subsequently used in finding the best ridge or tiling curve control point candidate. The values for r and s are decreased after each iteration:

$$r = r - (r/k), s = s - (s/k) \quad \text{(EQ 21)}$$

and successively decreased, as k, the current iteration, approaches the maximum number of iterations, $k_{max}$.

G. Simulated Annealing Cost Functions:

The cost function evaluates the candidates for B-spline control points intersected by the search plane via simulated annealing. The procedure used here is based on the Metropolis algorithm.

Ridge Curve Cost Function:

The value of the ridge curve search space cost function is computed from the twelve features (Table VIII):

$$E(\zeta) = \sum_{feature\ i=0}^{12} F_{\zeta_i^{-2}} \quad \text{(EQ 22)}$$

where $\zeta$ is a candidate space curve control point. Since the ridge curve requires maximum curvature values, the inverse of these squared distance feature is minimized during simulated annealing.

Tiling Curve Cost Function:

For tiling curves, the cost function is defined as:

$$E(\zeta) = \sum_{feature\ i=0}^{13} F_{\zeta_i^{-2}} \quad \text{(EQ 23)}$$

The curvature-based features, as well as the deviation measure ($d_m$) are minimized directly as squared distance features for tiling curve control point identification (Table VIII).

Figure 26A:
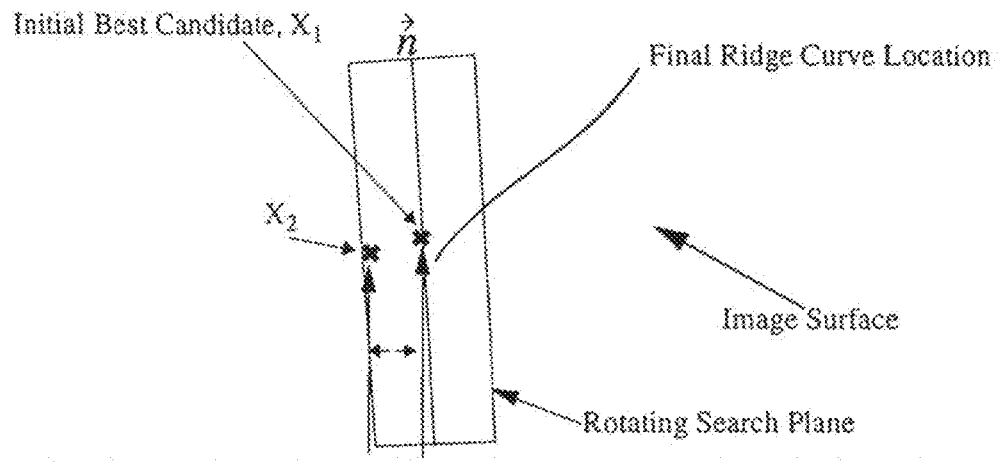
FIG. 26A illustrates rotating search planes.
Figure 26B:
FIG. 26B illustrates search planes for one ridge curve arrayed along a warped ridge curve-based deformable template space curve.
Figure 26C:
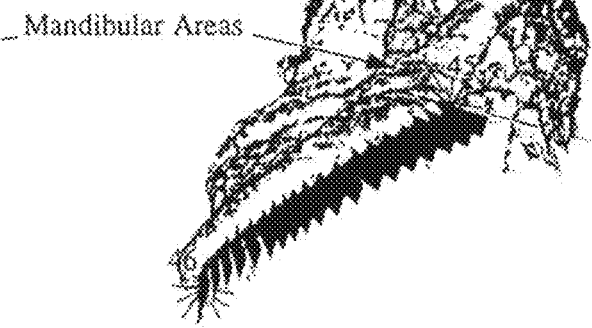
FIG. 26C illustrates a final ridge curve registration found by the simulated annealing algorithm.
Figure 26D:
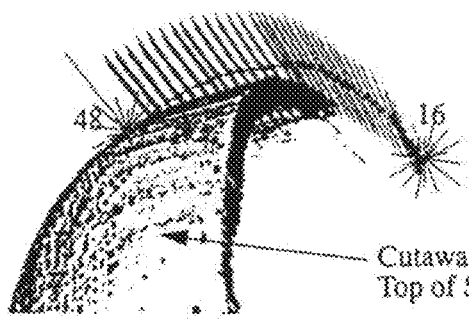
FIG. 26D illustrates a candidate tiling curve and its associated search planes.
Figure 26E:
FIG. 26E illustrates the fitted control points.
Figure 27:
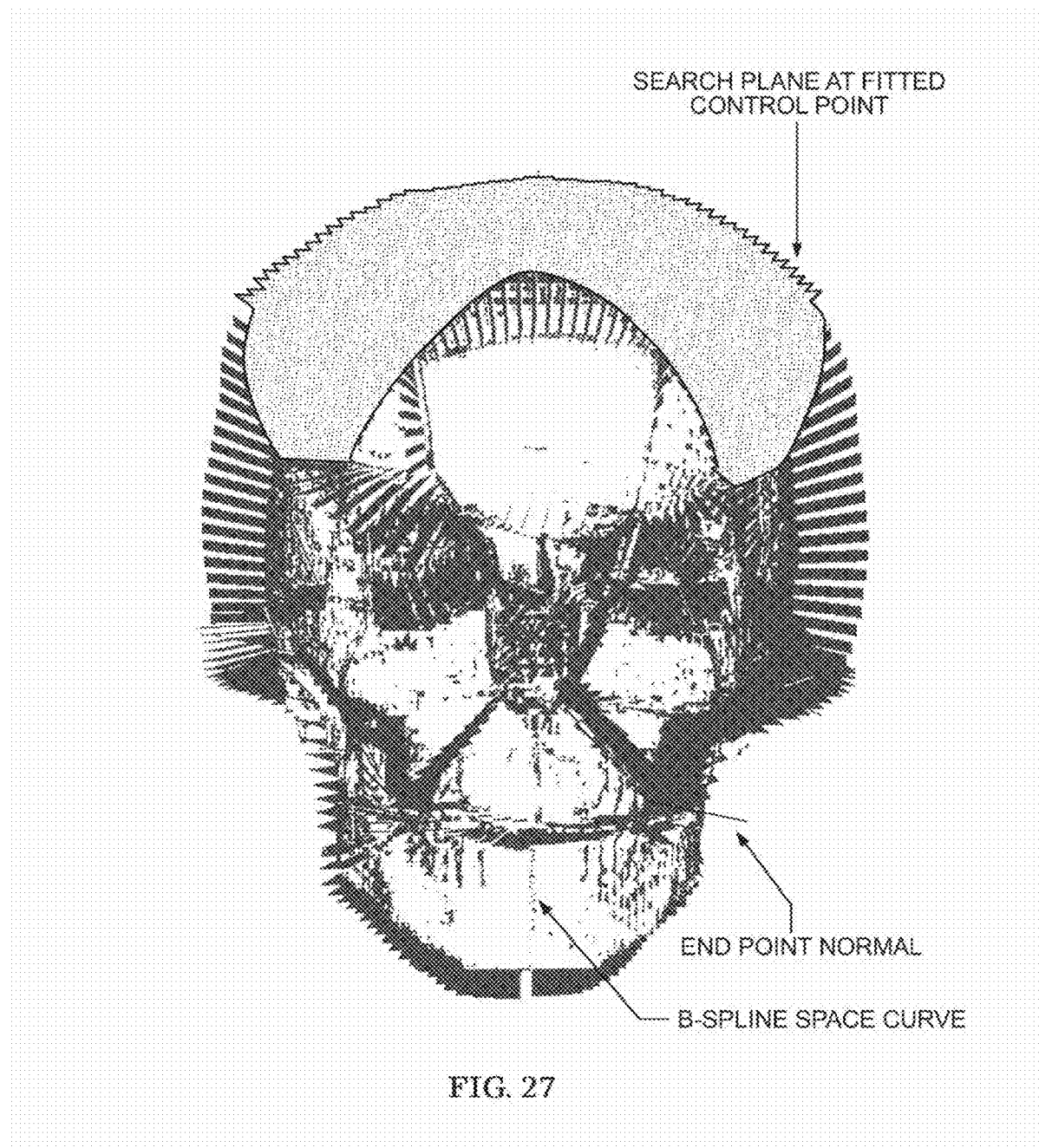
FIG. 27 illustrates an entire final ridge and tiling curve wireframe superimposed on the image surface.

H. Illustration of Control Point Location:

The rotating search planes are intended to identify optimal control point locations to assign to the ridge or tiling curve (FIG. 26A). For example, search planes for one ridge curve (i.e., menton_to_1_gonion) are arrayed along the warped ridge curve-based deformable template space curve in FIG. 26B. Here these search planes pass along the candidate ridge curve control point normal superiorly to find intersection with the voxels representing the base of the mandible. FIG. 26C, shows the final ridge curve registration found by the simulated annealing algorithm. Similarly, FIG. 26D shows a candidate tiling curve (i.e., r_ASSZ_to_r_PBP) and its associated search planes. FIG. 26E shows the fitted control points. FIG. 27 shows the entire final ridge and tiling curve wireframe superimposed on the image surface.

1. Simulated Annealing Algorithm Description: Four key elements are considered in our simulated annealing algorithm implementation: 1) The configuration definition; 2) Random candidate generation mechanism (i.e., definition of neighborhoods on the configuration space); 3) A cost function; and 4) A cooling schedule. In our implementation, we have first defined the configuration space with respect to the curvature features necessary to locate ridge or tiling curves on an image surface (Section II.2.C). Second, candidate control points are randomly generated from the search planes (Section II.2.F), Third, standard cost functions for location of ridge and tiling curves have been defined (Section II.2.G). Finally, the annealing procedure is described here.

Figure 28:
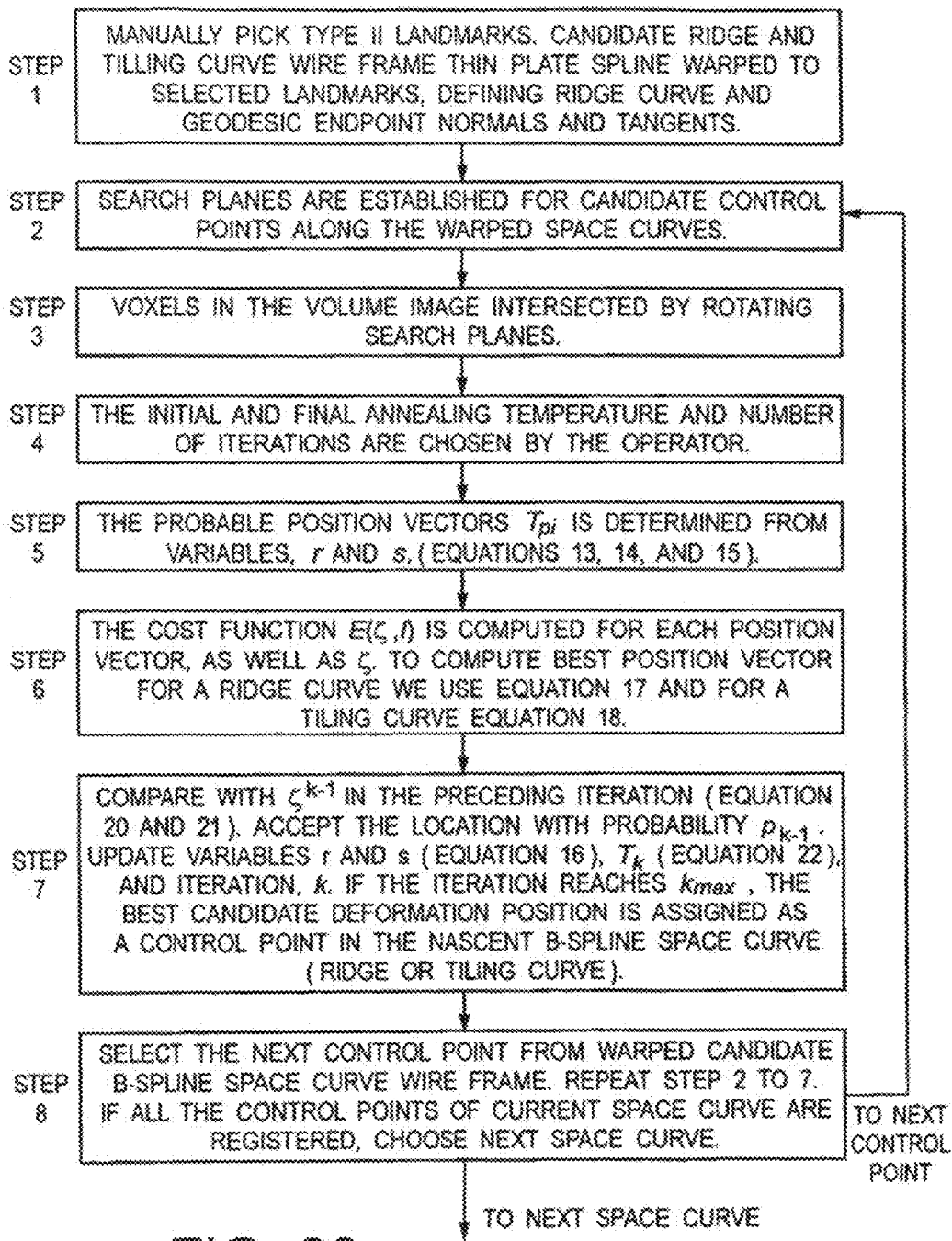
FIG. 28 illustrates a flowchart for minimizing the cost function.

The annealing algorithm (FIG. 28) attempts to minimize the cost function $E(\zeta)$ where $\zeta$ is a continuously modified candidate B-spline space curve control point, which lies in a search plane intersecting the surface. A set of cost functions are constructed from the sequence of template control point deformations $\zeta^1, \zeta^2$, to $\zeta^k$ starting from $\zeta^0$ at the initial ridge curve-based deformable template control point estimate. For each deformation, we have a set of P candidates $\zeta_0^k, \zeta_3^k, \ldots, \zeta_p^k$ within multiple search plane in current iteration, k. From the initial candidates, the best candidate $\hat{\zeta}^k$ is selected.

$$\hat{\zeta}^k = \zeta \text{ of } \|E_j(\zeta^k)\|_{min} \quad \text{(EQ 24)}$$

as k approaches the maximum number of iterations the cost function $E(\zeta)$ reaches a stable control point $\zeta^k$. Simultaneously, the temperature $T_k$, a component of the annealing procedure, is set to decrease monotonically. This parameter limits the search area and determines the probability of determining the best candidate between iterations. As the temperature lowers, the search area and number of probable candidates, narrows. At each iteration, k, the algorithm determines a new value of the B-spline control point deformation parameters, based on the previous value (i.e., $\zeta^{k-1}$) and compares it with the present value.

$\zeta^k$ is determined with probability $p_k$-1, which are defined as:

$$\zeta^k = \begin{cases} \hat{\zeta} \in p_k - 1 \\ \zeta_{k-1} \notin p_{k-1} \end{cases} \quad \text{(EQ 25)}$$

$$p_k - 1 = \min\left(\exp\left\{\frac{-[E(\hat{\zeta}) - E(\zeta^{k-1})]}{T_{k-1}}\right\}, 1\right) \quad \text{(EQ 26)}$$

$T_k$ is a monotonically decreasing temperature sequence, $E(\hat{\zeta})$ is the cost function computed at the current position l, and $E(\zeta^{k-1})$ is the cost function computed in the preceding iteration.

The temperature schedule $T_k$ [34]:

$$T_k = T_0 \left(\frac{T_f}{T_0}\right)^{\frac{k}{k_{max}}} \quad (EQ\ 27)$$

where $T_0$ is initial temperature, $T_f$ is final temperature, and $k_{max}$ is the number of maximum iterations allowed. FIG. 29 presents the temperature cooling schedule from the initial temperature 100 to the final temperature, −10. We set the number of iterations to 120 for our initial testing (see Section 4).

J. Final B-spline Ridge and Tiling Curve Registration:

FIG. 30 presents an overview of the ridge curve-based deformable template registration process in SASE. Manual editing of control point location is provided in the event that the simulated annealing algorithm fails to register a ridge curve arc to the operator's satisfaction. The operator may also locally vary the search parameters (i.e., sweep rotation degree, search plane height and width, or annealing temperature).

3. Surface Extraction

The registered R-spline control points are interpolated to produce a set of tile boundary points (i.e., smooth ridge or tiling curves). We set the default number of the boundary points for each space curve to 50, assuming this would be adequate in all cases. Each tile, therefore, consists of 2500 parametric points. Our soft tissue face ridge curve-based deformable template consists of 44 surface tiles [Tables VI and VII], 106376 the points. Our skull ridge curve-based deformable template consists of 47 surface tiles [Tables VI and VII], 113334 tile points. Note that some of the tiles are constructed with three bounding curves and the fourth side is a degenerate endpoint of the first and third sides. Since they are redundant, we can reduce the number of tile points encoded somewhat from the fully quadrilateral tile case of 110000 (soft tissue face) and 117,500 (skull).

Figure 30A:
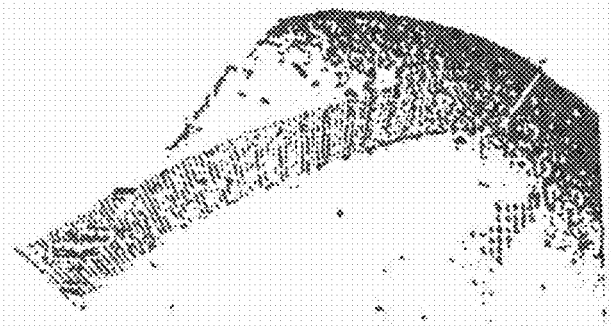
FIGS. 30A, 30B, and 30C illustrates an overview of a ridge curve based deformable template registration process in SASE.

A. Space Curve Registration To Volume Image Surface:

The trace of $I_n = \{I_{nx}, I_{ny}, I_{nz}\}$ provides the path along each tile boundary point normal to the voxel representing the segmented surface in the volume image. The position of the detected volume image surface point along the directed normal replaces the computed space curve point. FIG. 30A shows tiling space curve points registered onto the volume image surface via reference to the linked graphical manifold image. The surface normal at each point is seen as a single perpendicular line.

For each computed tile boundary point in a ridge curve or geodesic B-spline, a nearest point is located on the segmented surface voxels. The surface normal vectors, at current curve point I, are taken as the average of the local normal and interpolated end point normals:

$$I_{nx} = (((I_x - I_{cx})|xsize) + (e1_{nx} \cdot (1-p) + e2_{nx} \cdot p))/2 \quad (EQ\ 28)$$

$$I_{ny} = (((I_y - I_{cy})|ysize) + (e1_{ny} \cdot (1-p) + e2_{ny} \cdot p))/2 \quad (EQ\ 29)$$

$$I_{nz} = (((I_z - I_{cz})|zsize) + (e1_{nz} \cdot (1-p) + e2_{nz} \cdot p))/2 \quad (EQ\ 30)$$

where xsize, ysize, and zsize are the width, height and slices in the volume image. $I_{cx}$, $I_{cy}$, $I_{cz}$ is the midpoint of each coordinate, computed during the loading of a graphical manifold produced from the external tile boundary points.

The $I_{cx}$, $I_{cy}$, and $I_{cz}$ are:

$$I_{cx} = \frac{1}{T} \sum_{i=1}^{T} V_{ix}, \quad (EQ\ 31)$$

$$I_{cy} = \frac{1}{T} \sum_{i=1}^{T} V_{iy},$$

$$I_{cz} = \frac{1}{T} \sum_{i=1}^{T} V_{iz}$$

where $e1_n$ and $e2_n$ are the tiling space curve end point (i.e., Type II landmarks) normals, and p is the distance ratio of the current position I to the nearest space curve end point.

Figure 30B:
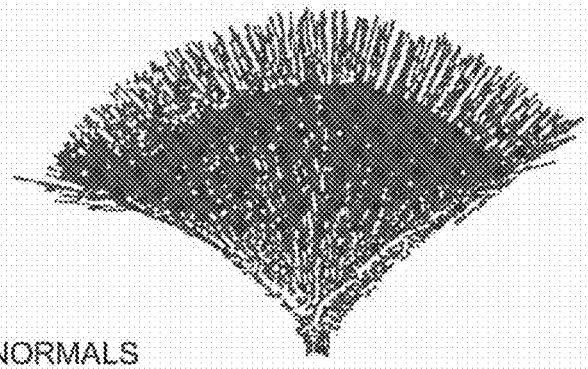
Figure 30C:
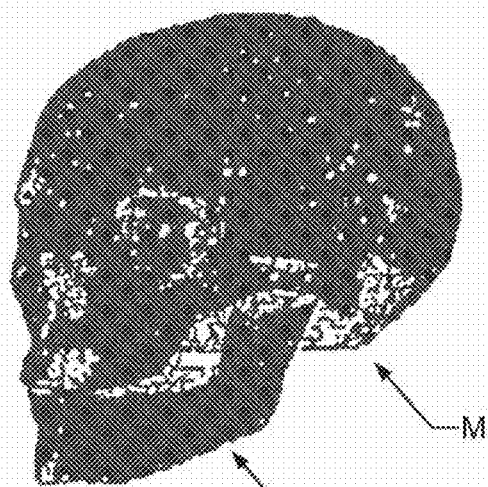

B. Interior Tile B-spline Space Curves Extraction:

The internal surface tile point vertices are determined via bi-linear Coons surface interpolation (equation 16). The Coons surface is converted into set of interior the B-spline space curves along u and v parametric directions. The normals of each surface the point are computed (equations 16, 28, 29, and 30). These normals are used to index the tile points to the volume image surface voxels (FIG. 30B). We compute the normal at each parametric surface tile point by directing a trace from the u, v location calculated from the Coon's surface to the voxels representing the segmented surface in the volume image. The detected volume image surface point replaces the Coons surface the point. FIG. 30C shows the extracted surface as it is displayed on the graphical manifold for the operator's approval.

4. Precision and Accuracy Tests and Results

The SASE 3D surface extraction program was written in C in the Silicon Graphics Unix (IRIX) environment and tested on a SGI Octane workstation (R10000 CPU, 256 Mbyte RAM). User interaction occurs via X11/Motif protocols.

We tested the SASE program with five 3D CT data sets (B2537, B2558, B2621, B3095, B3195) provided by a recall of subjects to the Bolton-Brush Growth Study Center at Case Western Reserve University. All subjects were females above 60 years in age. The boney skull and soft tissue face surfaces were segmented in a separate program. We measured the precision of our ridge curve-based deformable template registration and surface extraction by repetition. We compared both our surface extraction and that obtained by the toolkit to the segmented surface voxels in the volume image to test inter-method accuracy.

Figure 31:
FIG. 31 illustrates three orthogonal projection views showing direct differences between two surface extractions.

A. Precision Tests:

Intra-operator precision was tested by repeating the SASE, template registrations and surface extractions. Direct differences between the two surface extractions are projected into three orthogonal views (FIG. 31). Although, differences were minimal, most were localized to the oral and orbital regions. The oral region imprecision may be due to dental artifact. The orbital region imprecision may be due to surface ambiguity in thin bone structures. Operator manual effort in correcting ridge curve extraction varied requiring between 10% (soft tissue face) and 30% (skull) of the total surface extraction time in the SASE method. No tiling curve correction was necessary. We also computed the square root mean of sum of squared distance between all the points (Table IX).

Figure 32A:
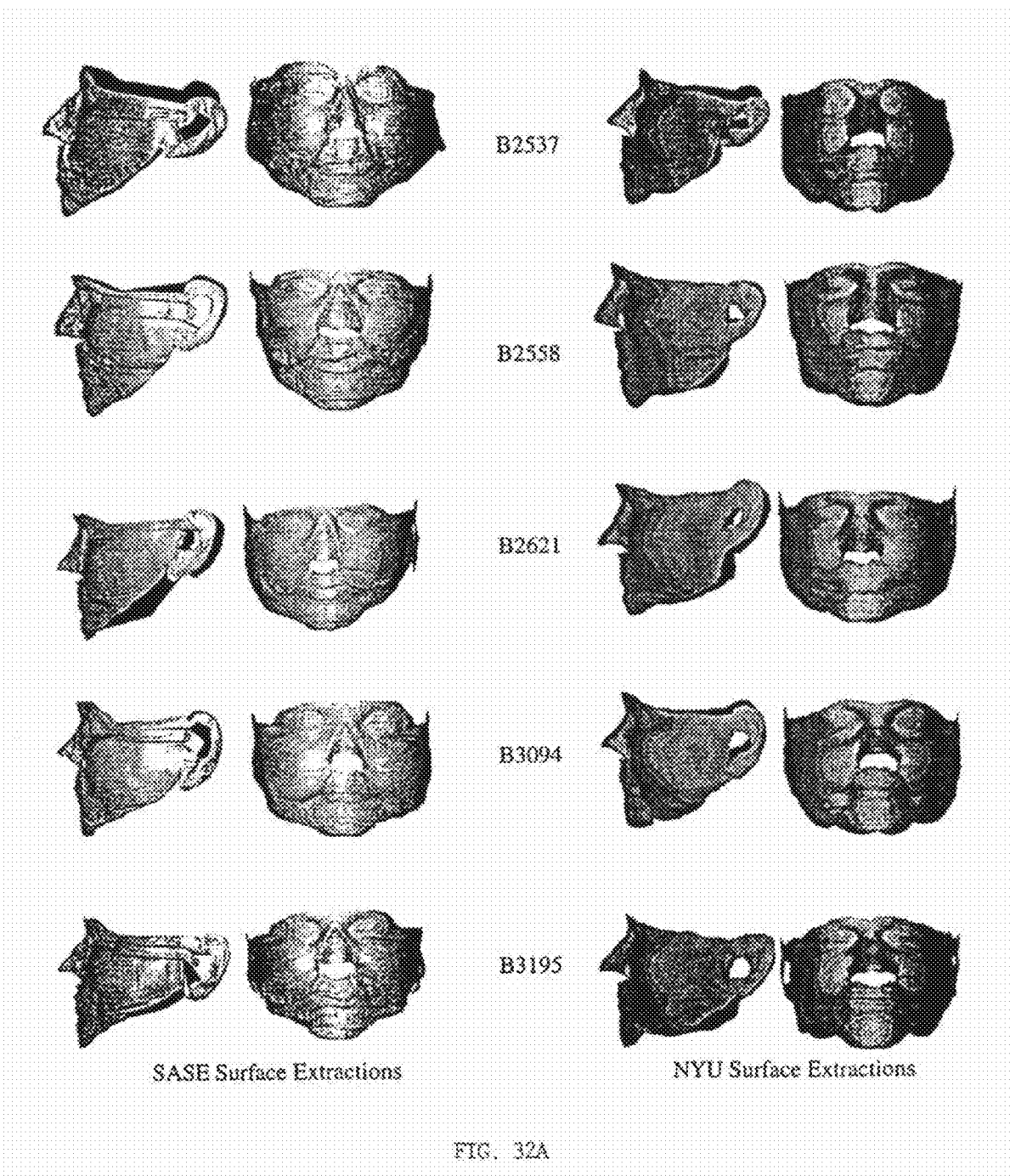
FIGS. 32A and 32B illustrate the soft tissue face surfaces and boney skulls, respectively, obtained via different methods versus the toolkit on the right side.
Figure 32B:
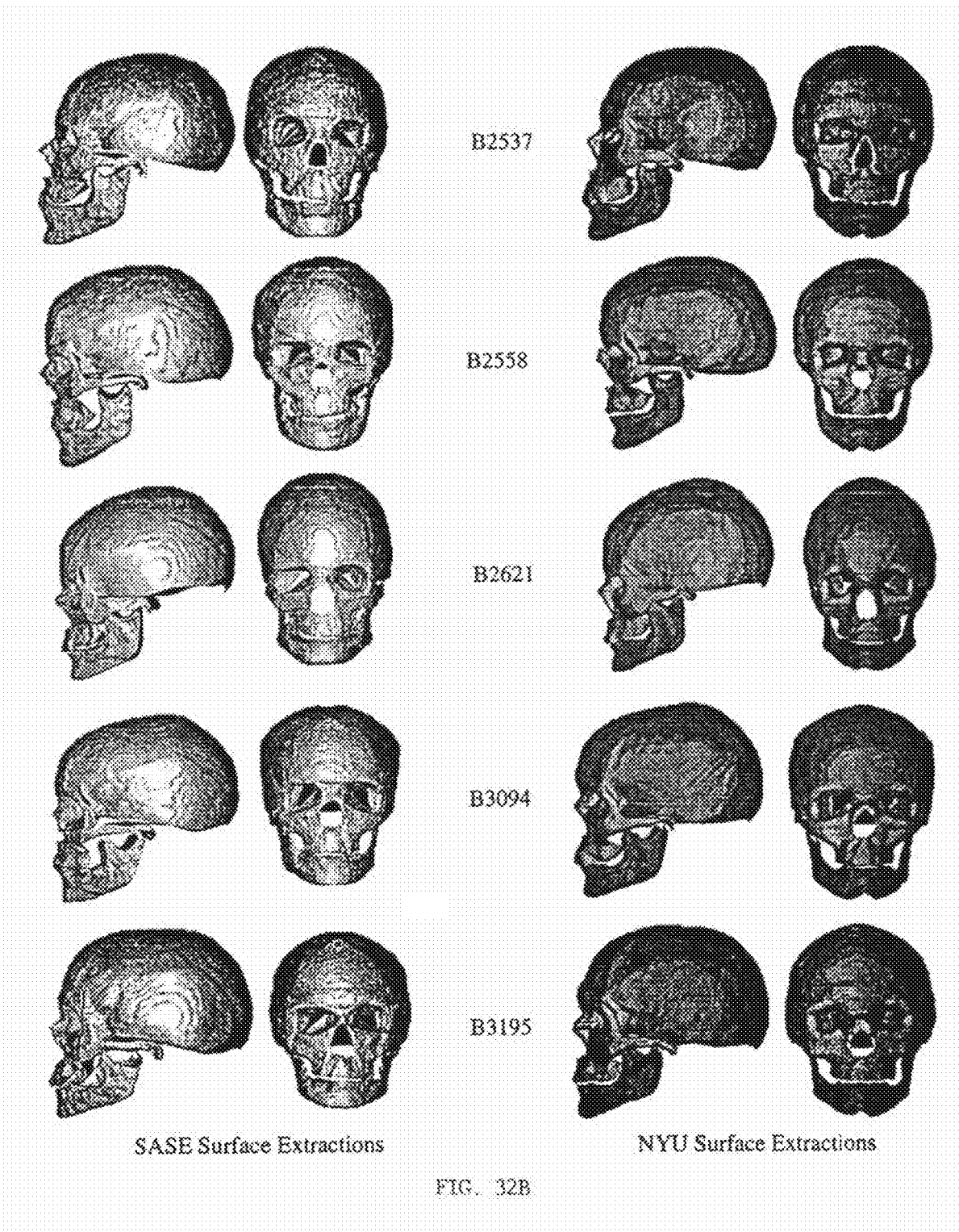

B. Inter-Method Accuracy Tests: 1. Visual Comparison:

The left side of FIG. 32A shows the soft tissue face surfaces obtained via the SASE methods versus the toolkit on the right side. FIG. 32B presents the same comparison for the boney skull.

2. Computed Differences:

The same segmented surface voxel volume image data were used for template registration and surface extraction by both the toolkit and the SASE program. This provides a baseline to compare how accurately the extracted surfaces match the volume image surface.

The toolkit generates an initial graphical manifold via the Wrapper and then converts it to Alligator/Winged Edge format. The Toolkits Alligator/Winged Edge graphical manifold is subsampled, first, during surface rendering from the segmented voxel step, introducing an error on the order of ±1 to ±3 mm for a constant sub-sampling rate of 2×2×2. Second, a wireframe is nudged into best position on this graphical manifold by interpolation. This step increases the error at each point by ±1 to ±3 mm depending on the variable level of parametric smoothing that the program automatically applies. The SASE surface extraction program indexes (links) the vertices of a less sub-sampled graphical manifold, used for operator interaction and approval, to the original segmented volume image voxels, where wireframe superimposition operations begin.

Figure 33A:
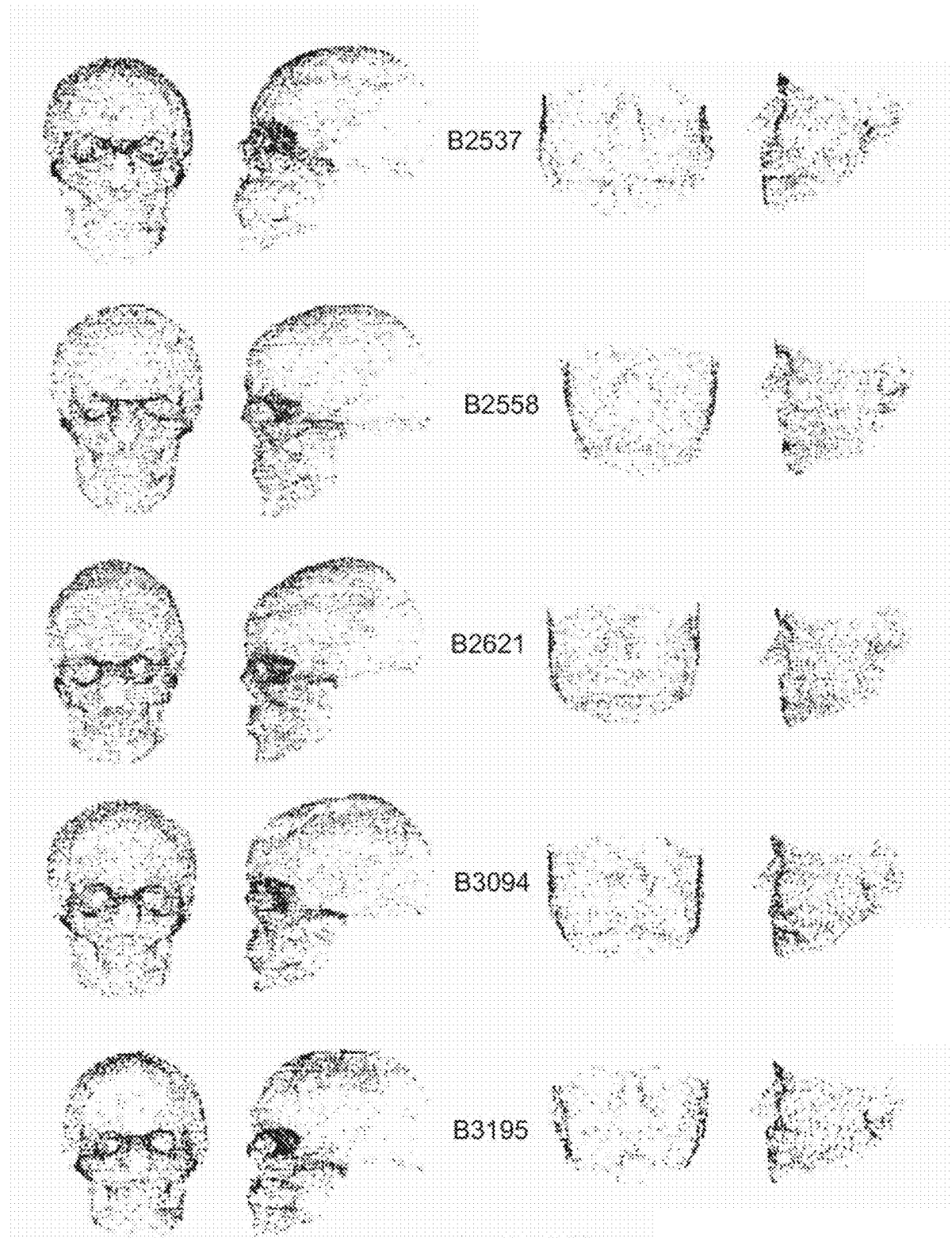
FIGS. 33A and 33B illustrate color coded difference images of the skull and soft tissue face surface extraction comparisons with the segmented voxel surface and color coded difference images of SASE skull and soft tissue face surface extractions, respectively.
Figure 33B:
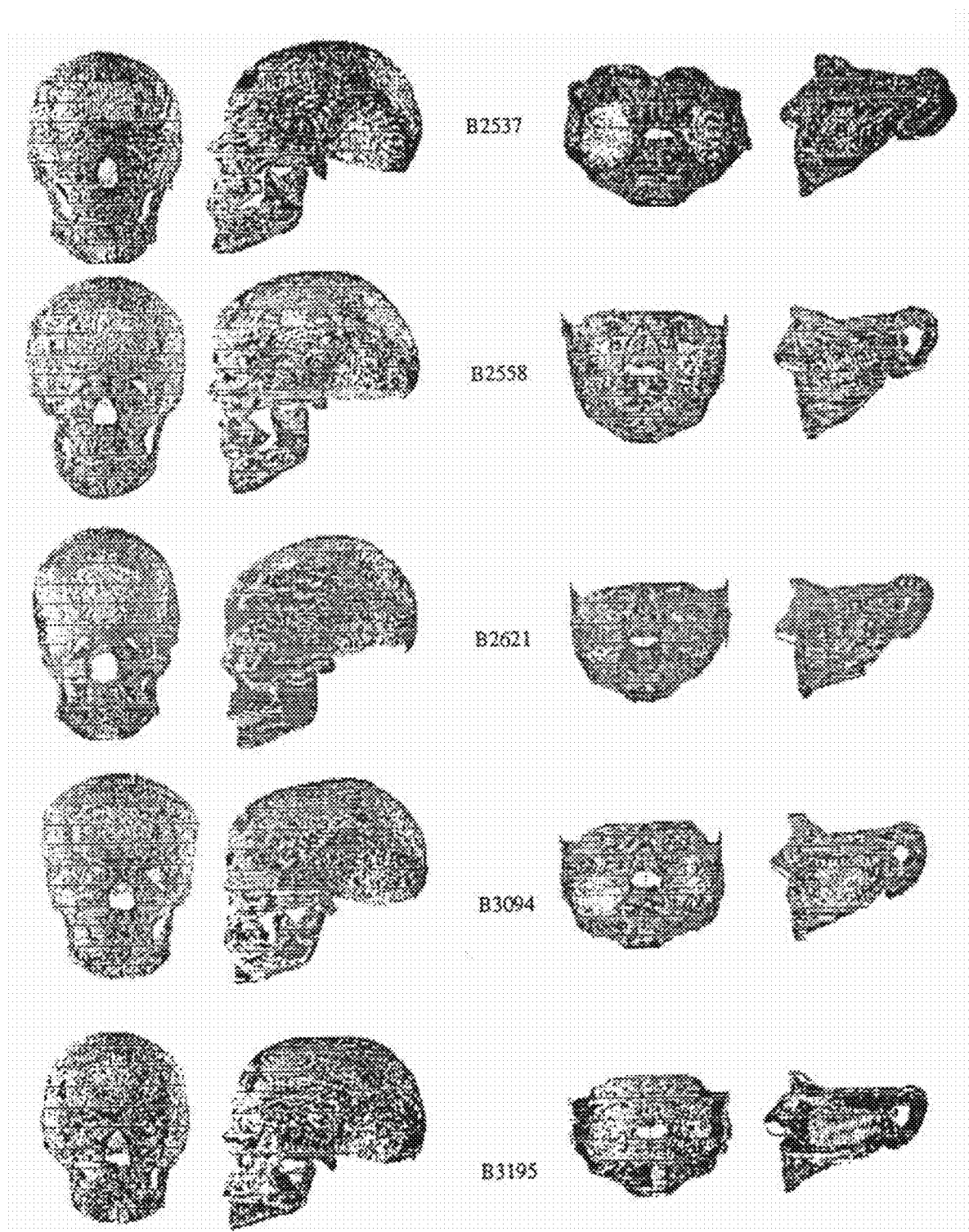

In our second inter-method test, the tile points m surfaces extracted by both methods were mapped to the segmented voxels in their shared source volume image space. The distances between the extracted surfaces and the nearest surface voxel in the volume image along the surface tile point normals were computed. Table X lists the square root of sum of squared distances for each method for all five CT data sets and both surface extraction methods. The surfaces, deviated from the original image voxels by an average of 6 mm for both the skull and soft tissue face surfaces. The SASE method average error was 0.47 mm for the soft tissue face and 0.46 mm for the boney skull (i.e., pixel resolution). FIG. 33A shows color coded difference images of the skull and soft tissue face surface extraction comparisons with the segmented voxel surface. Similarly, FIG. 33B shows the same color coded difference images of SASE skull and soft tissue face surface extractions. The error is scaled from lower difference in blue to larger differences in red. Note that despite higher sampling density the internal tile points are as true as the tile borders in the SASE extractions. Table XI presents the same results tile by tile. Note that the larger tiles have the greatest error in the toolkit extractions, especially on the calvarium.

Figure 34A:
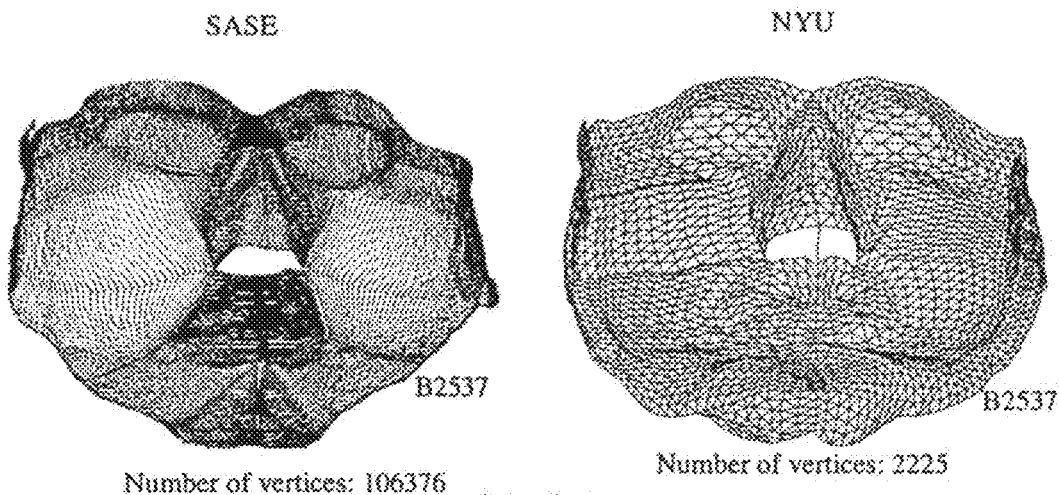
FIGS. 34A and 34B illustrate a tile point density.
Figure 34B:
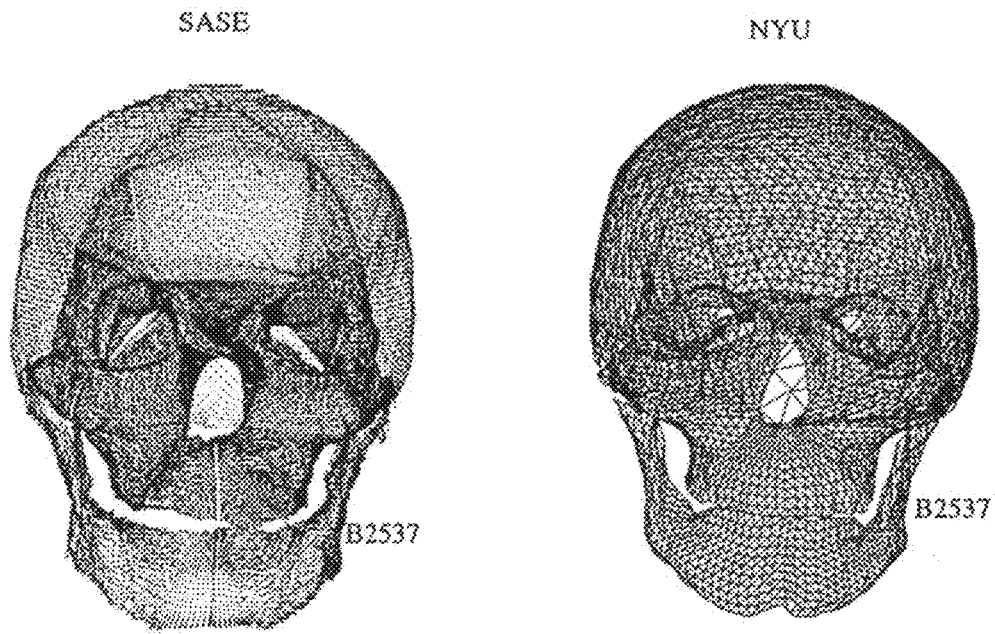

C. Other Inter-method Differences: 1. Tile Point Density:

FIG. 34 shows the tile point density. The toolkit extracts fewer points than the SASE program.

Figure 35:
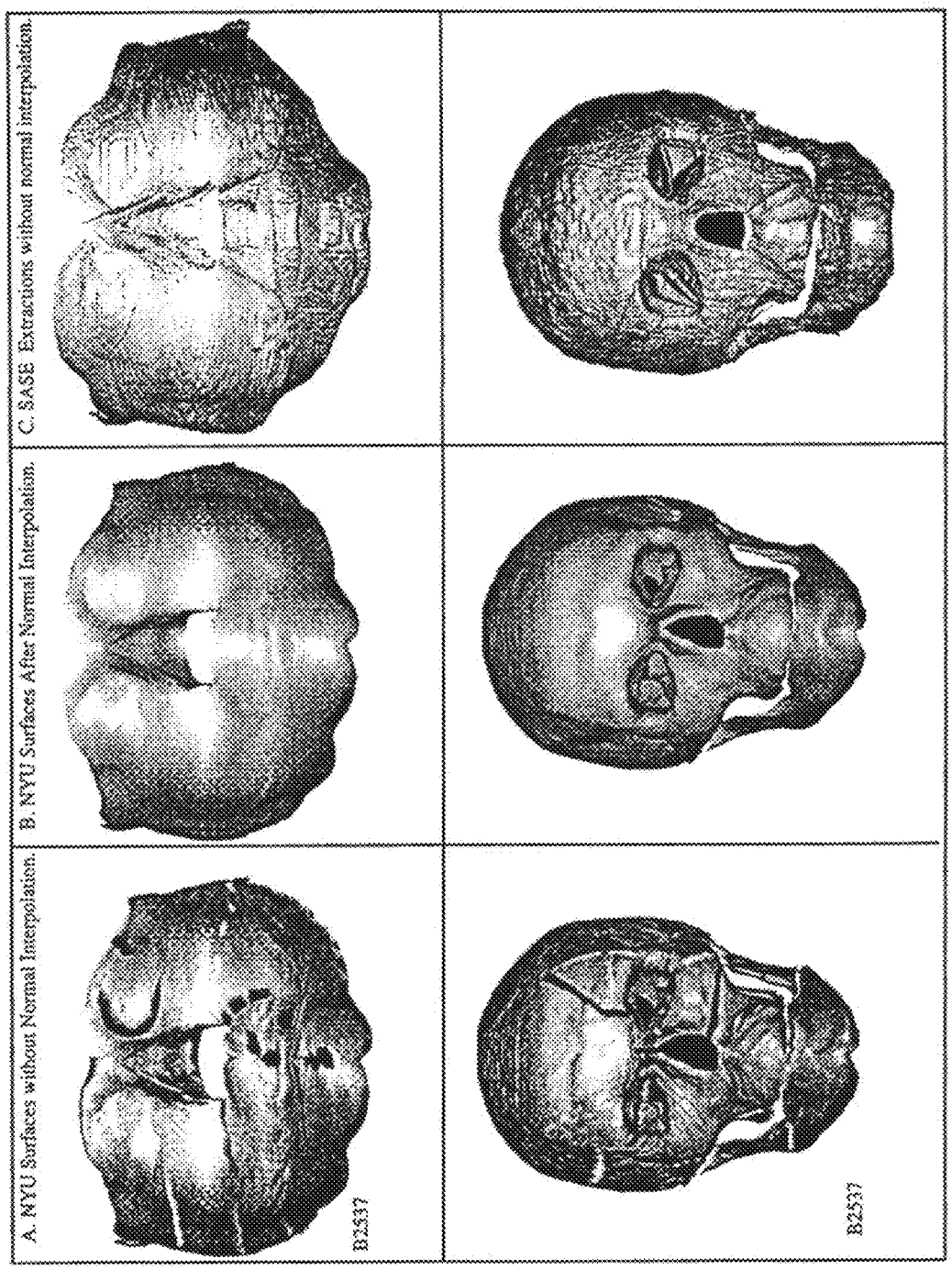
FIG. 35 illustrates the toolkit and SASE surface extractions.

2. Surface Patch Continuity:

Continuity of surface curvatures across surface tile boundaries is a critical rendering issue for parameterized ridge curve-based deformable template surface extraction. The toolkit interpolates surface normals providing smooth boundary transitions (i.e., no seam). FIG. 35 displays the toolkit and SASE surface extractions. The SASE program avoids interpolation, using the unaltered, detected segmented voxel surface normals.

3. Tendency of Toolkit to Enlarge Ridge Features:

As seen in FIG. 32, the toolkit tends to produce a bowing (see chin cleft, reduced nasal aperture, and reduced orbital aperture) of some ridge curves. This is primarily due to the interpolation process for surface tile boundary points beside Type II landmarks.

4. Time Taken:

Skull surface extraction with the toolkit for an experienced operator requires 2-3 hours. In the SASE interface, the operator may extract a skull surface in less than one hour, including the manual effort in correcting 10 to 30% of the automated ridge curve extractions.

III. Averaging

1. Parametric Surfaces and Surface Extractions

A. Surface Parameterization

We use a semi-automatic surface parameterization program, Simulated Annealing Surface Extraction (SASE), to homology map the segmented volume image surface. The SASE surface parameterization occurs via superimposition of a ridge curve-based deformable template to each sample member's surface of interest. The first step in the SASE method is manual location of Type II landmarks on a graphical manifold representation of the segmented surface voxels. Second, the candidate ridge curve-based deformable template is warped to these landmarks as in the toolkit. Finally, ridge and tiling curve superimposition occurs via a simulated annealing algorithm which primarily evaluates surface curvature information found in the unsubsampled volume image data. The superimposed ridge curve-based deformable template defines a homology mapped parametric surface that is encoded as a series of B-spline space curves. The toolkit does not use volume image data to superimpose ridge curve-based deformable templates, relying instead on the operator to manually nudge the ridge curve deformable template onto a graphical manifold.

B-Spline Ridge and Tiling Curve Wireframe

A B-spline space curve may be recorded as a set of 3D $\{Q_k\}$, ($k=1, \ldots, n$) points incrementally stacked along a sweep in 3D space represented as a $P$th degree non-rational B-spline. By assigning a parameter value, $u_k$, to each $\{Q_k\}$, with an appropriate knot vector $U=\{a, \ldots, a, u_{p+1}, \ldots, u_{m-p-1}, b, \ldots, b\}$, where a and b are initial and final conditions (i.e., $0, \ldots, 1$), and m is an ascending function, a B-spline space curve is:

$$Q_k = C(u_k) = \sum_{i=0}^{n} N_{i,p}(u_k) P_i \quad (EQ\ 32)$$

where $N_{i,p}(u_k)$ is the $P$th degree B-spline basis function. These basis functions define the non-periodic and non-uniform knot vector, U, and control points, $P_1$. We set the degree of interpolation components as 3, and order 4 (degree+1) for all space curves. B-spline basis functions of the 3rd degree are defined as:

$$N_{i,0}(u) = \begin{cases} 1, \ldots, u, < u < u_{i+1} \\ 0, \ldots, (u \leq u_i) \text{ or } (u \geq u_{i+1}) \end{cases} \quad (EQ\ 33)$$

$$N_{i,3}(u) = \frac{u - u_i}{u_{i+3} - u_i} N_{i,2}(u) + \frac{u_{i+4} - u}{u_{i+4} - u_{i+1}} N_{i+1,2}(u) \quad (EQ\ 34)$$

from the initial condition, these interpolant variables are computed with the knot vectors.

We use a chord length method to select each knot vector and a linear averaging method to determine knot spacing along the ridge curve and tiling curve B-spline space curves. Knot density is pre-determined by the operator. Since each axis is interpolated separately, as in the 2 dimensional case, the x, y, and z axes can be treated separately to encode each space curve.

C. B-Spline Surface Tile Grids

Figure 36A:
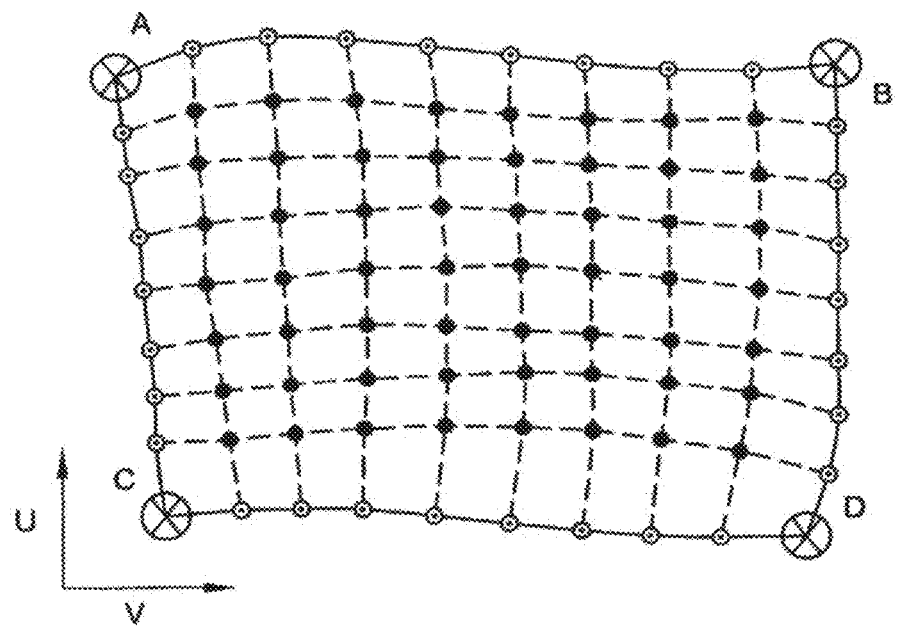
FIG. 36A illustrates an alignment of u and v internal tile curves in a 4 sided tile.
Figure 36B:
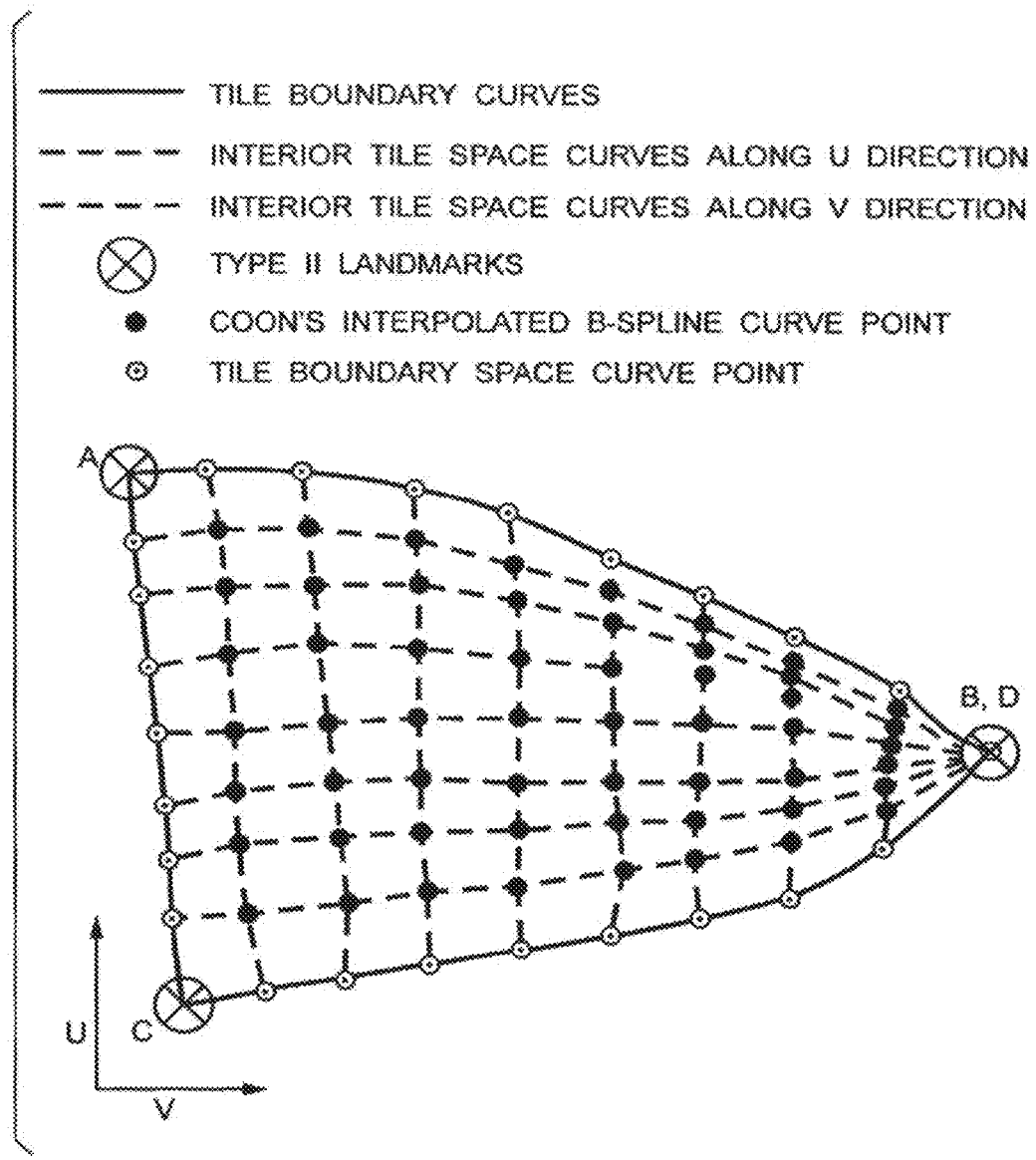
FIG. 36B illustrates an alignment of u and v internal tile curves in a 3 sided tile.

Based on ridge curve and geodesic the (tiling curve) boundaries alone, a surface tile is defined as a bi-linearly blended Coons surface. We extend this definition. We take the internal tile point grid and tie it to the surface voxels segmented from the original volume. Next, we encode these points as row and column B-spline curves in u, v space (FIG. 36A). This improved homology mapping prevents overlapping of internal tile points during averaging. Our surface tiles are either three or four sided. In the case of a three sided tile, the fourth side is generated by placing the same number of second side points, with each point filled by a common degenerate value from the intersection of the first and third boundary space curves (FIG. 36B).

Our template uses a bi-linear blending function to define location for interior tile points:

$$Q(u,w) = [1-u \quad u \quad 1] \begin{bmatrix} -P(0,0) & -P(0,1) & P(0,w) \\ -P(1,0) & -P(1,1) & P(1,w) \\ P(u,0) & P(u,1) & 0 \end{bmatrix} \begin{bmatrix} 1-w \\ w \\ 1 \end{bmatrix} \quad \text{(EQ 35)}$$

where the functions ((1-u), u, (1-w), w) (i.e., blending functions) blend the boundary space curves to produce the preliminary internal shape of the surface as a cosine function; P is the parametric function representing the interior tile points with respect to parametric values u and w. The surface points generated are fitted to the original image surface via a surface normal trace to the surface voxels segmented from the volume image. The trace modifies the shape of the tile by registering each final surface tile point to the original volume image surface (i.e., segmented voxels). The operator sees the result projected onto a graphical manifold surface. The surface tile points are recorded as rows of B-spline space curves spanning the two pairs of the tile bounding space curves (FIG. 36).

Figure 37A:
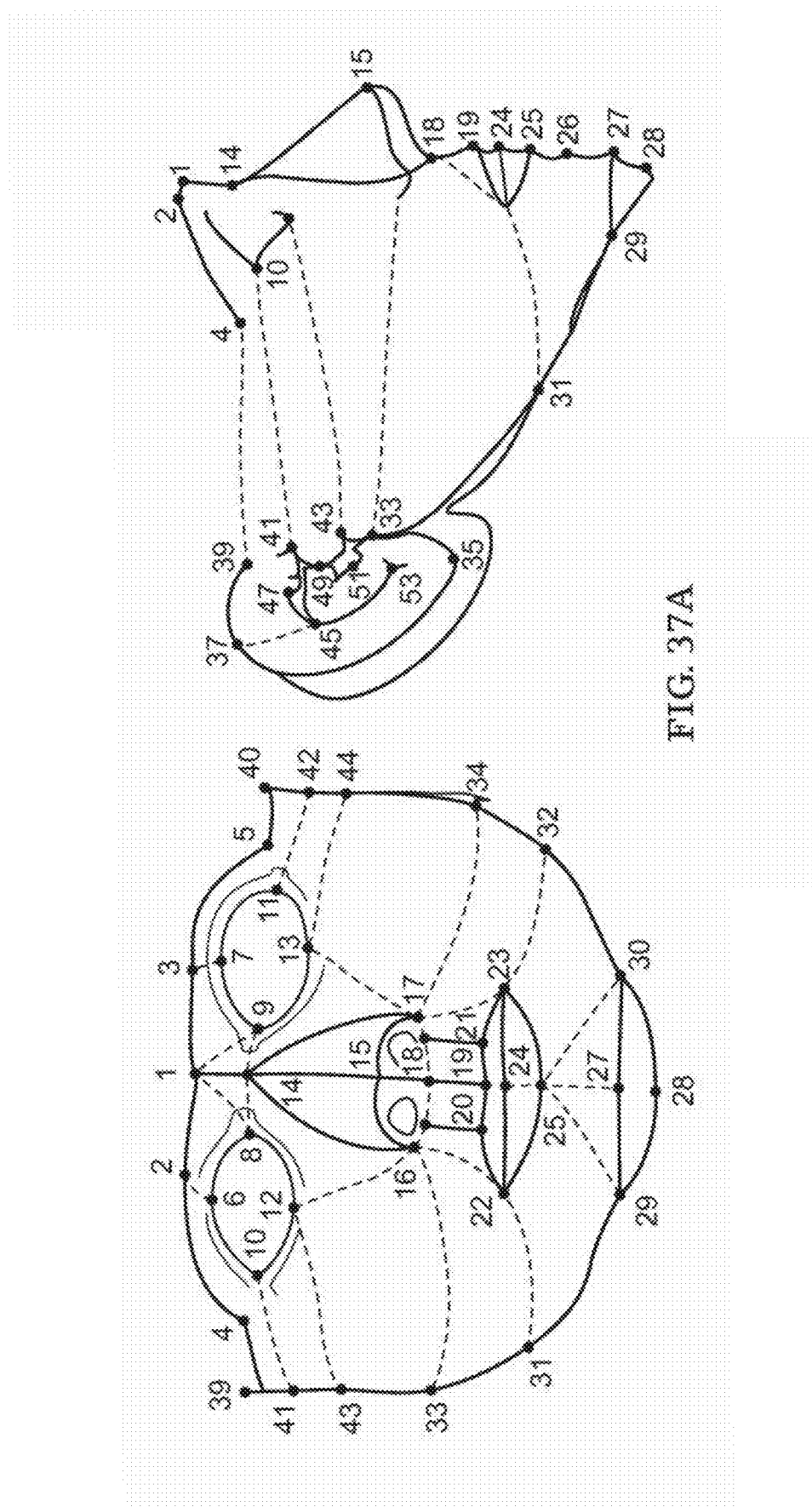
FIG. 37A illustrates a soft tissue face ridge curve-based deformable template definition.
Figure 37B:
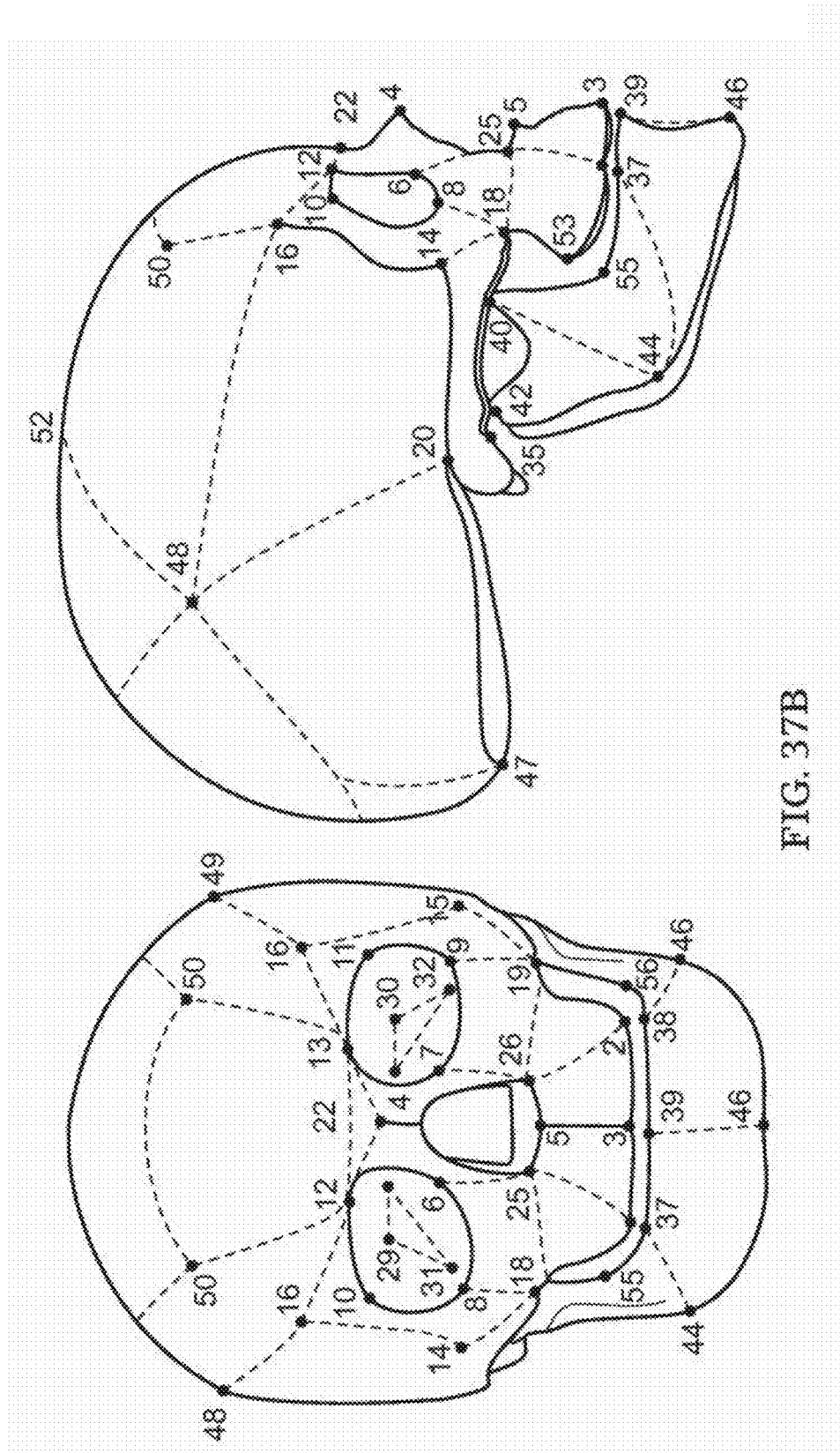
FIG. 37B illustrates a boney skull deformable template definition.

The caption to FIG. 37 lists the Type II landmarks found in both soft tissue face and boney skull surface templates. Our current soft tissue face template consists of 56 landmarks, 103 space curves (64 ridge curves and 49 geodesics), and 48 surface tiles (FIG. 37A). Our current skull template consists of 54 landmarks, 104 space curves (40 ridge curves and 64 geodesics), and 47 surface tiles.

2. Computational Tools for Average Generation

As with the toolkit, the first step in our surface averaging algorithm is the generation of an average Type II landmark configuration. We use the Procrustes superimposition method to produce an average Type II landmark configuration. The ridge and tiling space curve B-splines making up each sample member are globally warped to this average landmark shape and locally unwarped.

A. Procrustes Superimposition for Production of Average Type II Landmark Configuration The Procrustes superimposition method is applied to two landmark coordinate configurations at a time. The two homologous shapes are referred to as landmark configurations $X_1$ and $X_2$, are pxk matrices with $k$-dimensional coordinates of the p vertices of Type II landmarks. Since the geometric operations are linear, this could be extended to include any number of configurations, from $X_2$ to $X_N$. The order in which Procrustes Fitting occurs has no effect on the shape of the final configuration. A Procrustes fit attempts to minimize the sum of the squared distances between corresponding vertices of both configurations.

Translation: The coordinates of and $X_1$ and $X_2$ are translated to a shared origin, thereby k dimensions are reduced from the overall pk dimensions. This is achieved by subtracting the respective means of each axis from the $X_1$ and $X_2$ matrices. $X_1$ and $X_2$ are translated to the origin by pre-multiplying X by (1−P), where P is a px P identity matrix., and is a matrix with every element equal to 1/p. Therefore 1−P is:

$$\begin{bmatrix} 1-\frac{1}{p} & -\frac{1}{p} & -\frac{1}{p} & -\frac{1}{p} \\ -\frac{1}{p} & 1-\frac{1}{p} & -\frac{1}{p} & -\frac{1}{p} \\ -\frac{1}{p} & -\frac{1}{p} & 1-\frac{1}{p} & -\frac{1}{p} \\ -\frac{1}{p} & -\frac{1}{p} & -\frac{1}{p} & 1-\frac{1}{p} \end{bmatrix} \quad \text{(EQ 36)}$$

and the translation of $X_1$ and $X_2$ to a shared origin is computed as $X'_1=(1-P)\cdot X_1$, and $X'_2=(1-P)\cdot X_2$. This translation is shown in FIG. 38A.

Scaling:

A scalar value, called "Centroid Size," $S_1$ of $X_1$, is calculated by taking the square root of the sum of squared distances of each landmark to the centroid. Centroid size is computed for each axis separately and divided for each control point P:

$$S_1 = \sqrt{\text{trace}((1-P)X_1 X'_1(1-P))} \quad \text{EQ 37}$$

Similarly, $S_2$ of $X_2$ is calculated. The translated and scaled versions $$X_1^n = \frac{1}{S_1} \cdot X'_1$$

and $$X_2^n = \frac{1}{S_2} \cdot X'_2$$

are seen in FIG. 38B.

Rotation:

The translated and scaled configuration is next rotated to obtain a minimum root sum of square distance between corresponding points. The first step is to rotate all configurations about the first configuration. Next the "rough" average (FIG. 38) position of all the rotated configurations is determined. Finally, all configurations are rotated to the rough average position to obtain the final average configuration. The configuration $X''_1$ is rotated to overlay on configuration $X''_2$ so that the root sum of squared distances between the corresponding landmarks is minimized. First the $X''_1$ configuration is rotated by transposing it and pre-multiplying it by H, a k×k matrix. Therefore, the $X''_2$ configuration to rotated $X''_1$ is $$\hat{X}'_3 = X''_2 \cdot H \quad \text{(EQ 38)}$$

Where $\hat{X}'_2$ is rotated $X''_2$ configuration, 1 is the transpose operator and H is obtained by $H=VSU^1$ where V and U are obtained from the singular value decomposition of the product of transpose of $X''_1$ and $X''_2$ as:

$$X'''_1 X''_2 = U\Sigma V^1 \quad \text{(EQ 39)}$$

S is the matrix of diagonal elements of ±1 corresponding to the signs of the $\Sigma$ matrix in equation 39. The average configuration $X_A$ is the average of $X''_1, \hat{X}_2$. The rotation shown in FIG. 38C. For the multiple configuration average, we first compute the rough average $X'_A$ by rotating the configurations to the first configuration, one at a time;

$$X'_2=\{X''_1,X''_2\}, X'_3=\{X''_1,X''_3\} \ldots X'_N=\{X''_1,X''_N\} \quad (EQ\ 40)$$

where N is the number of configurations to be superimposed. $X'_A$ is computed as:

$$X_A = \frac{1}{N}\{X_1^n + \hat{X}'_2 + \ldots + \hat{X}'_N\} \quad (EQ\ 41)$$

To produce the final Type II landmark and tile boundary B-spline control point average, we rotate each configuration to the rough average configuration, $X_A$, one at a time:

$$\hat{X}_1=\{X'_A,X''_1\}, \hat{X}_2=\{X'_A,X''_2\} \ldots \hat{X}_N=\{X'_A,X''_N\} \quad (EQ\ 42)$$

The consensus average landmark configuration $X_A$ is computed from $\hat{X}_1, \hat{X}_2, \ldots, \hat{X}_N$ as:

$$X_A = \frac{1}{N}\{\hat{X}_1 + \hat{X}_2 + \ldots + \hat{X}_N\} \quad (EQ\ 43)$$

B. Thin Plate Splines

We use a thin plate spline to initially position all sample member surfaces at the average Type II landmark configurations. The first landmark transformations matched homologous regions of two and three dimensional wireframe drawings of organisms. A spatial interpolation routine, widely used in geology and metallurgy, the thin plate spline, was suitably modified and applied to this problem. A thin plate spline warp results in a bending energy matrix describing the shape deformation of the anchor points (i.e., control points and Type II landmarks). We use the thin plate spline to provide a global warp of sample members ridge, tiling curve, and internal tile 13-spline points to the rough average Type II landmark configuration.

Although the warp is based only on the Type II landmarks shared by all sample members, the appropriate position of all surface tile points is achieved via the mapping function $f(R^2-R^2)$ such that $f(S_1)=S_A$, based on the Type II landmarks. This function, a bi-harmonic equation $U(r)=r^2 \log r^2$, is a generalized solution. The basis function, $r=\sqrt{x^2+y^2}$ is limited to the two dimensional case. We extend it to three dimensional surfaces as $U(r)=r$, where $r=\sqrt{x^2+y^2+z^2}$. A 3D thin plate spline function can be generalized and interpreted visually as $\{(r,s,t,\delta(r,s,t)) \in R^4 \| r,s,t \in R\}$. If $S_A$ is our consensus average Type II landmark reference configuration, with k=3 dimensions and p vertices, (i.e., a k×p matrix), the matrix $S_A$ and function matrix K are defined as:

$$S'_A = \begin{bmatrix} 1 & 1 & 1 & \ldots & 1 \\ x_1 & x_2 & x_3 & \ldots & x_p \\ y_1 & y_2 & y_3 & \ldots & y_p \\ z_1 & z_2 & z_3 & \ldots & z_p \end{bmatrix}, 4\times p \quad (EQ\ 44)$$

$$K = \begin{bmatrix} 0 & U(r_{12}) & \ldots & u(r_{1p}) \\ U(r_{21}) & 0 & \ldots & U(r_{2p}) \\ \ldots & \ldots & \ldots & \ldots \\ U(r_{p1}) & U(r_{p2}) & \ldots & 0 \end{bmatrix}, p\times p \quad (EQ\ 45)$$

$U(r_c)$ is defined in 3D as the distance from the $i^{th}$ to $j^{th}$ the point in the reference configuration as:

$$U(r_c)=\sqrt{(x_i-x_j)+(y_i-y_j)+(z_i-z_j)} \quad EQ\ 46$$

Next, a projection operator L is defined as:

$$L = \begin{bmatrix} K & S_A \\ S'_A & O \end{bmatrix}, (p+4)\times(p+4) \quad (EQ\ 47)$$

O is a 4×4 null matrix. We use these mapping functions to globally warp a series of ridge curve based deformable template (i.e., ridge, tiling, and internal tile B-spline space curves) wireframes to the rough average Type II landmark configuration via a global warp. Once in position, each space curve is locally unwarped to begin the averaging process.

In general, thin plate spline warping is defined with a set of homologous points Y, as $L^{-1}Y$, and the transformation is defined:

$$S(X'_{ni}) = A[1 \ x \ y \ x]' \bigg|_{ni} + \sum_{j}^{p} n_j U(r_j), \quad (EQ\ 48)$$

$$n = 1 \ldots I$$

3. Average Surface Generation

Our space curve averaging is a two step process. The first step begins following the local unwarping of space curves that were globally thin plate spline warped to an average landmark configuration. Then all sample members are locally unwarped and averaged, B-spline sample by B-spline sample (i.e., each set of homologous ridge, tiling, or internal tile curves).

A. Average Type II Landmark Configuration

We use the Procrustes Superimposition method to align the sample member landmark configurations and compute an average configuration from them. Procrustes fitting removes variation due to position, orientation, and scale prior to our calculating a simple average. In equation 45 we see that the computed average configuration is set to $X_A$.

B. Average Space Curve Generation

Figure 39:
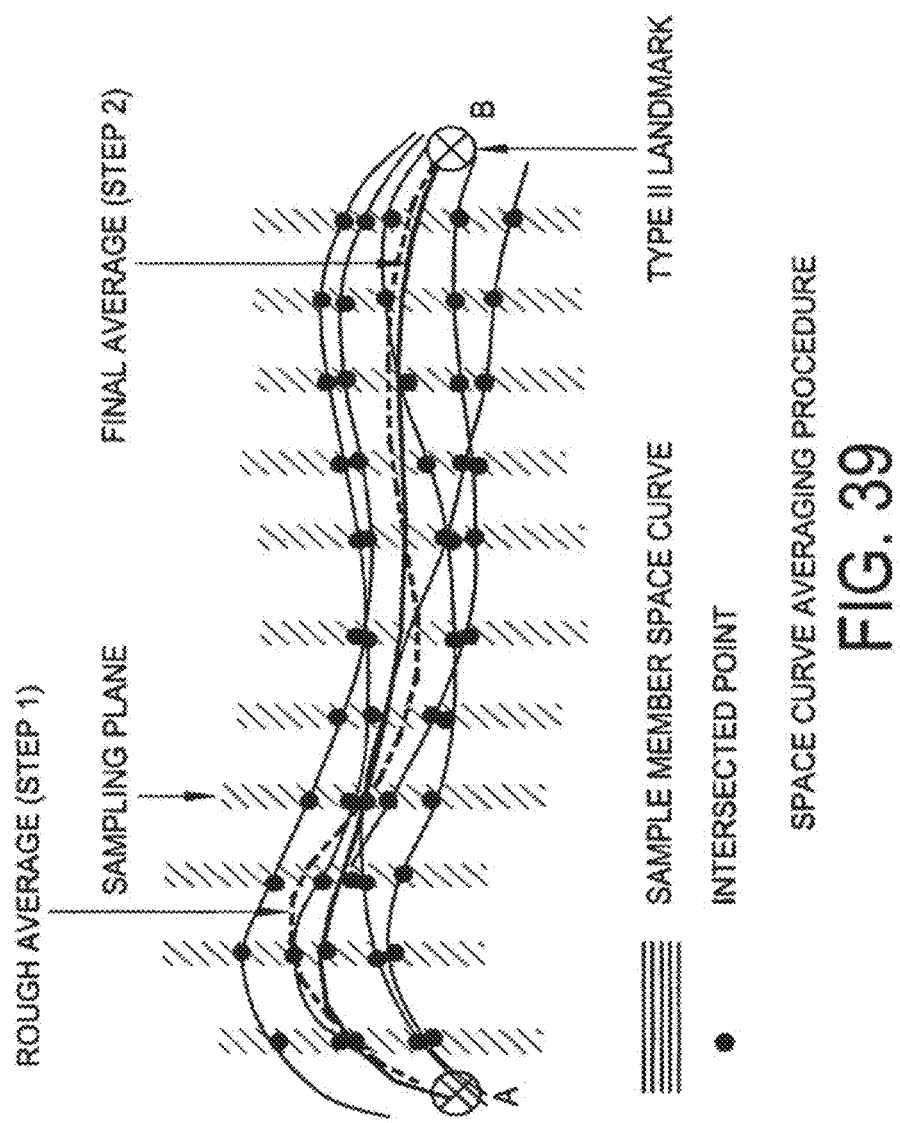
FIG. 39 illustrates a space curve averaging procedure.

This is accomplished algorithmically as follows: Let the configurations $S_n$ where n varies from 1 to N wireframe space curves (i.e., The wireframe consists of the tile boundary B-spline space curves). $X_A$ is an average landmark configuration (Equation 45). Each sample configuration $S_n$ is warped to $X_A$ landmarks. We refer to this sample of globally warped configurations as $\hat{S}_A$. Next, each member of $\hat{S}_n$ is locally unwarped to the original configuration $S_n$ for each space curve. The locally unwarped and assembled space curves are shown in FIG. 39 drawn between hypothetical Type II landmarks A and B. A "rough" average curve is produced as a direct average of the control point coordinates (note: this is possible for B-splines but not for Bezier splines where the control points may not lie on the encoded space curve). The rough average curve is then re-splined. The re-splined rough average curve is displayed as a dashed line in FIG. 39. The second step is the generation of final average space curves. Sampling planes (perpendicular bi-sectors) are positioned at regularly spaced intervals along the rough average curve. A control point for each sampling plane is produced from the average of intercepted points. Finally, a B-spline space curve is generated from the average intercept points (FIG. 39, thick dark line).

The space curve averaging is done separately for each type of space curve (i.e., ridge, tiling, and internal tile curves). Ridge curves are further divided into arc-segments between Type II landmarks for averaging. The complete set of average space curves represents the average surface.

C. Internal Tile Curve Averaging

Internal tile curves have either u or v orientation (see FIG. 36). Therefore each internal tile point belongs to two B-splines. We compute the average u and v internal tile B-spline space curves separately. The average of these two points is then substituted back to internal tile vertices, in order to prepare a triangulated (graphical manifold) surface. Algorithmically, B-spline internal the curve segments in the u and v direction may be represented as matrices:

$$S_i(C_u) = \begin{bmatrix} C_{1,1} & C_{1,2} & \ldots & C_{1,v} \\ C_{2,1} & C_{2,2} & \ldots & C_{2,v} \\ \ldots & \ldots & \ldots & \ldots \\ C_{u,1} & C_{u,2} & \ldots & C_{u,v} \end{bmatrix}$$ (EQ 49)

$$S_i(C_v) = \begin{bmatrix} C_{1,1} & C_{1,2} & \ldots & C_{1,u} \\ C_{2,1} & C_{2,2} & \ldots & C_{2,u} \\ \ldots & \ldots & \ldots & \ldots \\ C_{u,1} & C_{v,2} & \ldots & C_{v,u} \end{bmatrix}$$

The computed interior surface tile control points thus are the average of the above two matrices, $S_t(C_v)$ and $S_t(C_u)$:

$$S_i(C) = S_i(C_u) + S_i(C_v)'$$ (EQ 50)

$$= \begin{bmatrix} C_{1,1} & C_{1,2} & \ldots & C_{1,v} \\ C_{2,1} & C_{2,2} & \ldots & C_{2,v} \\ \ldots & \ldots & \ldots & \ldots \\ C_{u,1} & C_{u,2} & \ldots & C_{u,v} \end{bmatrix} + \begin{bmatrix} C_{1,1} & C_{1,2} & \ldots & C_{1,u} \\ C_{2,1} & C_{2,2} & \ldots & C_{2,u} \\ \ldots & \ldots & \ldots & \ldots \\ C_{u,1} & C_{v,2} & \ldots & C_{v,u} \end{bmatrix}$$

where t varies from 1 to the number of tiles in the whole sample surface.

4. Precision and Inter-Method Tests and Results

The SSA program was written in C in the Silicon Graphics Unix (IRIX) environment. It was tested on a SGI Octane workstation (R10000 CPU, 256M byte RAM). The program interface integrates Procrustes superimposition, thin plate spline warp, and surface averaging methods with graphical manifold surface rendering operator feed hack. User interaction occurs via X11/Motif protocols.

To test the SSA program, we averaged soft tissue face surfaces (FIG. 40A) and skull surfaces (FIG. 40B) from segmented from 3D CT volume images. These five 3D CT data sets (B2537, B2621, B3037, B3095, B3195) were provided by a recall of subjects. All subjects are above 60 years in age, female, have dental fillings, and often have large oral prostheses (dentures). The soft tissue face and skull surface segmentation of the volume images was performed in a separate program, SOFM. The ridge curve-based deformable template superimposition and surface parameterization was done in an another program, SASE.

A. Intra-Operator Precision Test

We conducted a precision test of the SSA methods between two sessions by one operator. The operator introduces variation through initial seeding and subsequent fine tuning of the ridge and tiling curve template, superimposition. The overall root mean square error between the surface the points of two averaging sessions, of the boney skull surface average was 0.0 mm and for the soft tissue face surface average was 0.0 mm. This is complete agreement between sessions. This intraoperator reproducibility result (i.e., precision) provides evidence that the SSA method is reliable.

B. Inter-Method Tests

We next compared the surface sampling used to produce average surfaces by the SSA program versus that of the toolkit using the same segmented voxel data obtained from the SOFM program. We hypothesize that improved homology of tiling and internal tile curves in the SSA method will reduce the variance of the sample members about the average.

i. Visual Comparison

Figure 42A:
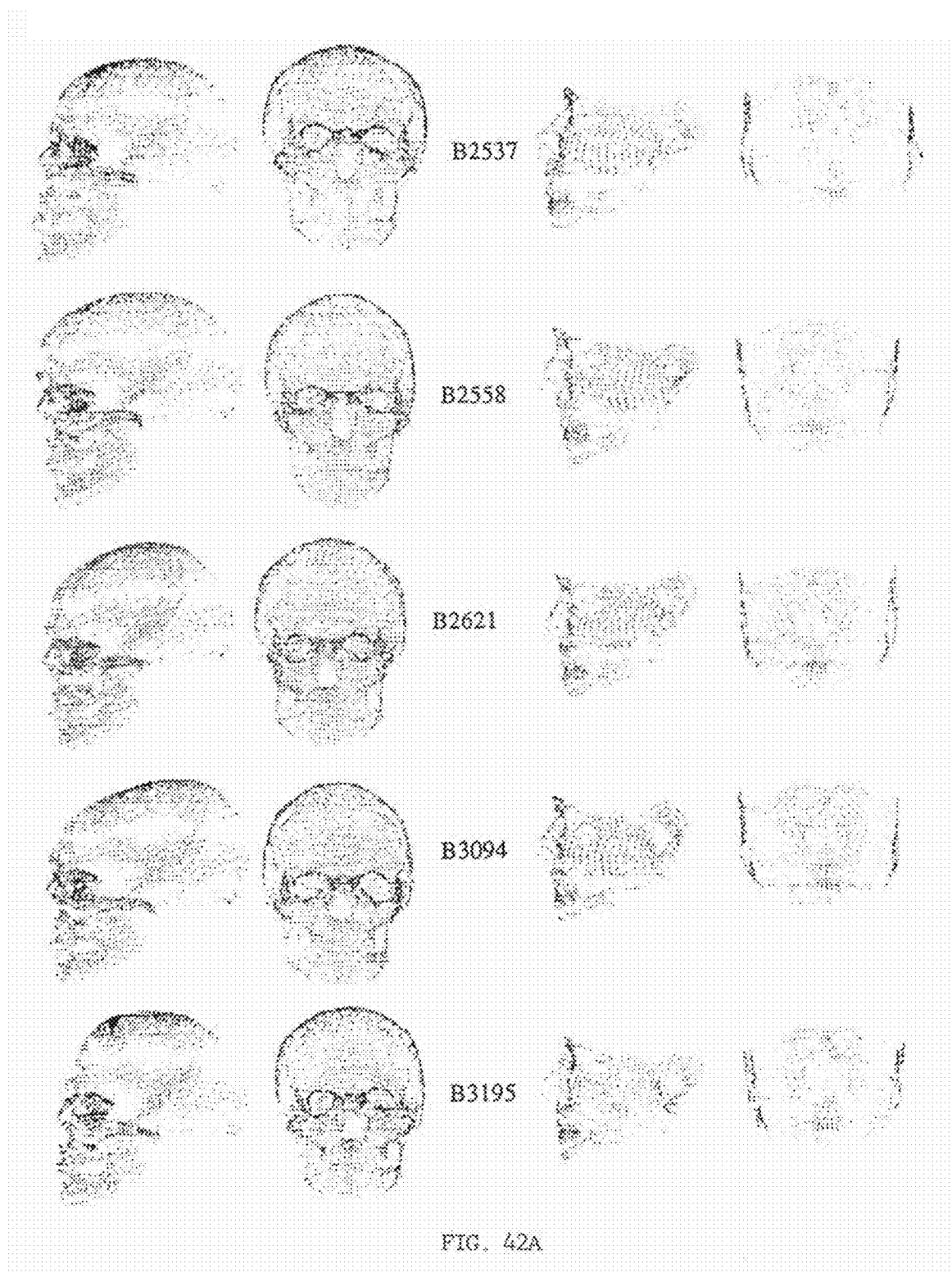
FIG. 42A illustrates a surface average tile-by-tile color coded error maps for skull and soft tissue face surface extractions.
Figure 42B:
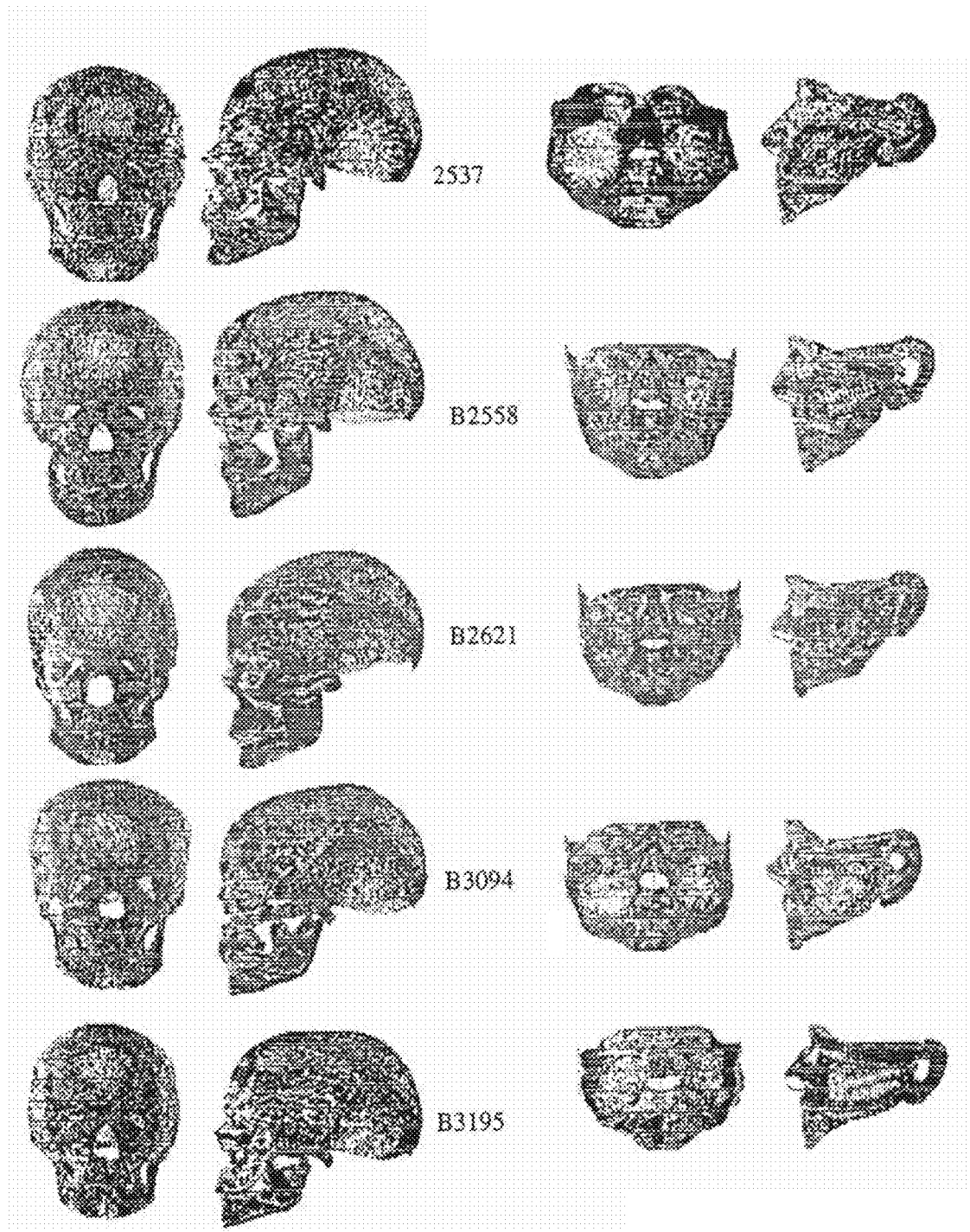
FIG. 42B illustrates an SSA surface average tile-by-tile color coded error maps for skull and soft tissue face surface extraction.

We parameterized all 10 surfaces with both the SASE and the toolkit for the soft tissue face (FIG. 41A) and the boney skull (FIG. 41B). Note that the toolkit sample and average surface images appear to bow along every ridge curve edge (e.g., orbits and nasal regions). Under the chin, we note that this problem has exaggerated a notch not seen in the SSA average. This bulging also results in smaller orbital and nasal apertures relative to the shape seen in the original segmented surface voxels. This and the smoother surface may be an artifact of splining a lesser number of points than in the SSA method.

ii. Inter-Method Comparison of Average Surface Warped to Members' Original Segmented Voxel Surface We thin plate spline warped the average surface to the Type II landmark configuration of it's member surfaces. Then, we traced each fitted average surface tile point to the segmented surface image. Both averaging methods (i.e., toolkit and SSA) used surfaces extracted from the same segmented volume image, providing a common basis for comparison between the two methods. The computed square root of sum of squared differences are listed in Table XII. Note, the number of tile points in the toolkit surface extractions is well below that used in the SSA method. Given this difference, we observed an average of 6 mm distance for the toolkit averaging method for all points in the soft tissue face and skull surfaces, whereas the average SSA distance were 0.448 mm in the case of the soft tissue average and 0.419 mm in the case of the skull average. Table XIII presents these results tile by tile. FIG. 42A displays color coded difference images of toolkit skull and soft tissue face surface averages with their source segmented voxel surfaces. Similarly FIG. 42B shows the same color coded difference images of the SSA skull and soft tissue face surface averages. The same range of difference is scaled from lowest difference in blue to largest difference in red in both images. Note that despite higher sampling density the internal tile points are as true as the tile borders in the SSA extractions.

iii. Results

Figure 43A:
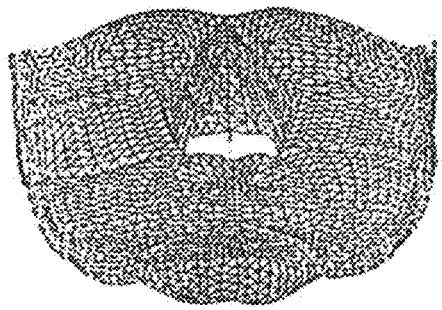
FIG. 43A illustrates a tile point density for soft tissue face average.
Figure 43B:
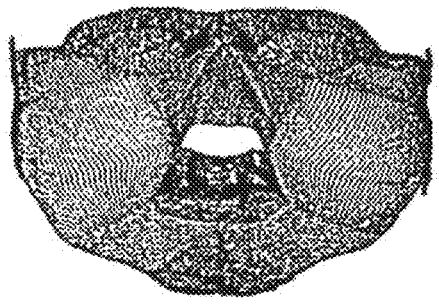
FIG. 43B illustrates an SSA method tile point density.
Figure 43C:
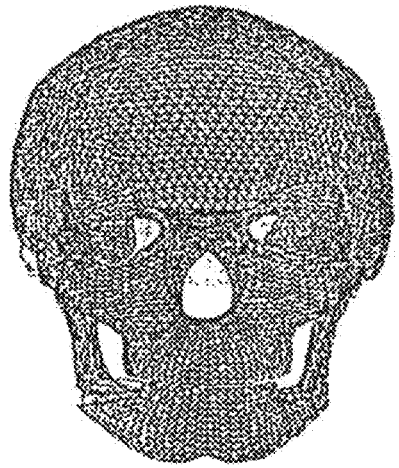
FIG. 43C illustrates a boney skull surface average.
Figure 43D:
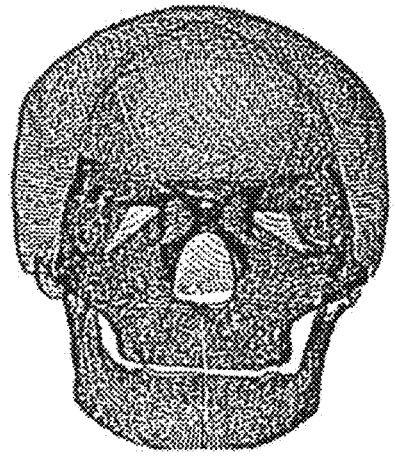
FIG. 43D illustrates an SSA method skull the point density.

In FIG. 43A, we see the toolkit average surface prior to the final step of normal interpolation and averaging. FIG. 43B presents the same surfaces afterward. FIG. 43C presents the final SSA average surface; the SSA algorithm does not average surface normals. Note that seams are present but they less disturb the continuity of surface curvature, between the tile surfaces. In both cases these are graphical rendering artifacts, not an indication of inaccuracy in surface parameterization or a non-shape preserving average.

5. Conclusion

One reason that the SSA average surface results better preserve surface curvature continuity, and reduce variance about the average, is the higher sampling density (FIG. 44). The toolkit's graphical manifold is subsampled at four stages. Surface rendering of the segmented voxels introduces an error of ±1 to ±3 mm assuming a sub-sampling rate of 2×2×2.

Second, a wireframe is manually nudged into best position on this graphical manifold and then interpolated. This step increases the error at each point by ±1 to ±3 mm depending on the variable level of parametric smoothing that the program automatically applies. Third, the surface is sparsely encoded. This may eliminate some otherwise useful information from the patient surface image.

Finally when generating the average, only the surface tile boundaries (i.e., ridge curve and geodesic lines) are truly averaged in the toolkit. The average interior tile points are assigned, not found. Overall, the errors accumulated at each surface the point vary from 3 to 6 mm.

It appears to us that the SSA method improves tiling and internal tile curve homology assignment. The SSA method better preserves overall shape of 3D surfaces during averaging because of (1) the improved homology assignment of internal tile points, and (2) the extension of the original space curve averaging method to the entire surface.

The utility of average surface images for clinical diagnosis needs validation. Their use for boney prosthetic design is apparent. These methods were originally developed to quantify diagnostic morphometric differences of clinical populations, however we expect these data have applications at every stage of patient care, as well as other deformable model applications including animation.

Figure 45:
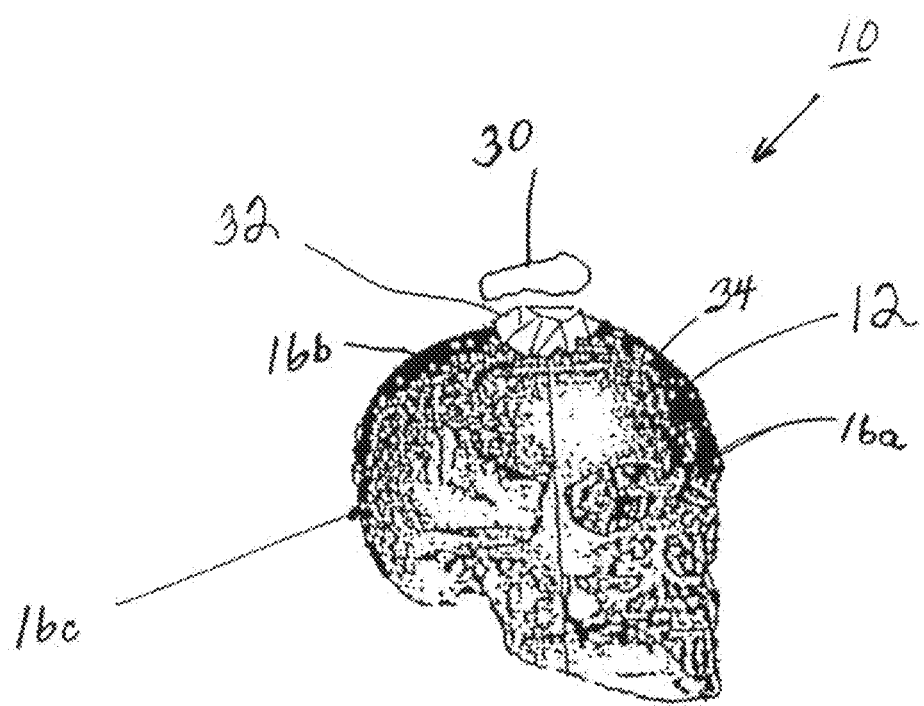
FIG. 45 illustrates a three-dimensional model according to the present invention.
Figure 46:
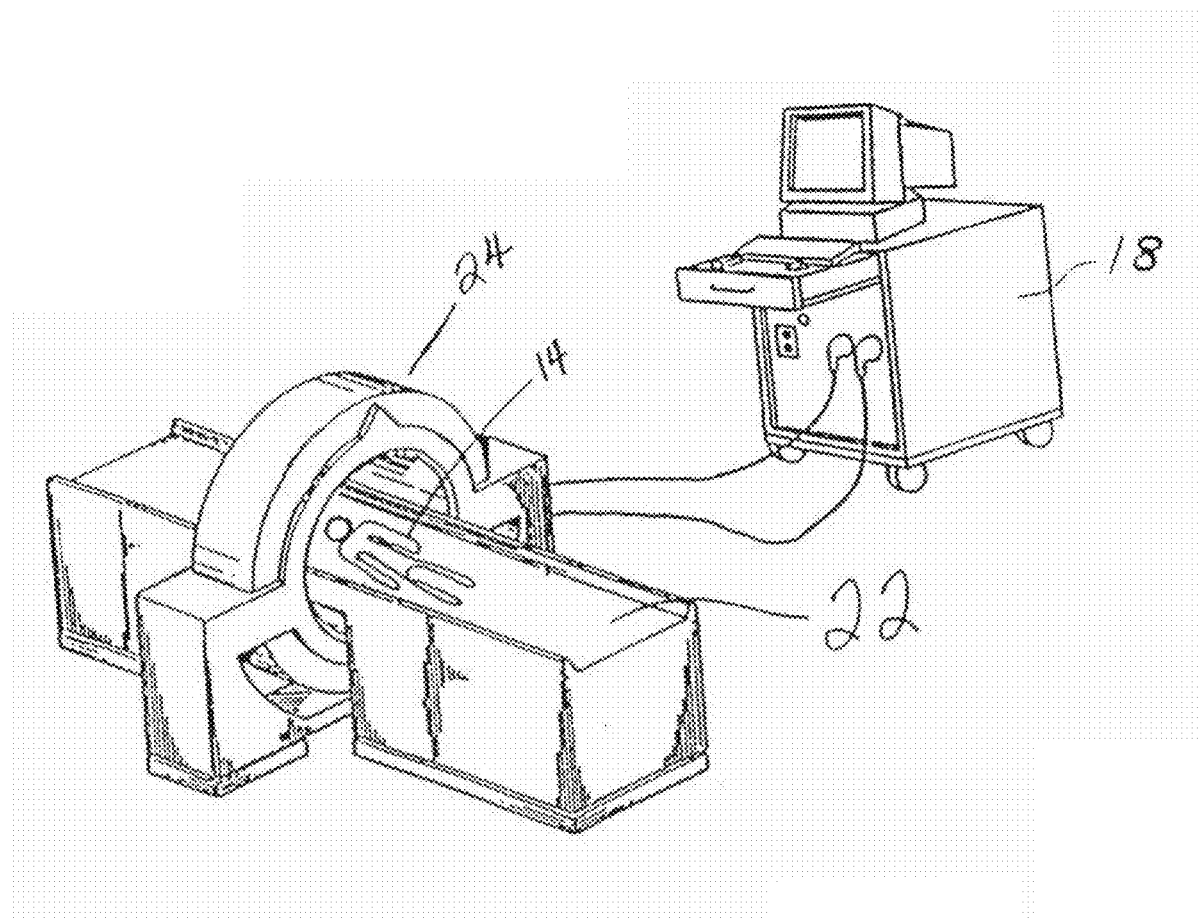
FIG. 46 illustrates a system for acquiring a three-dimensional image as source data for a hard model of the patient's anatomy according to the present invention.
Figure 47:
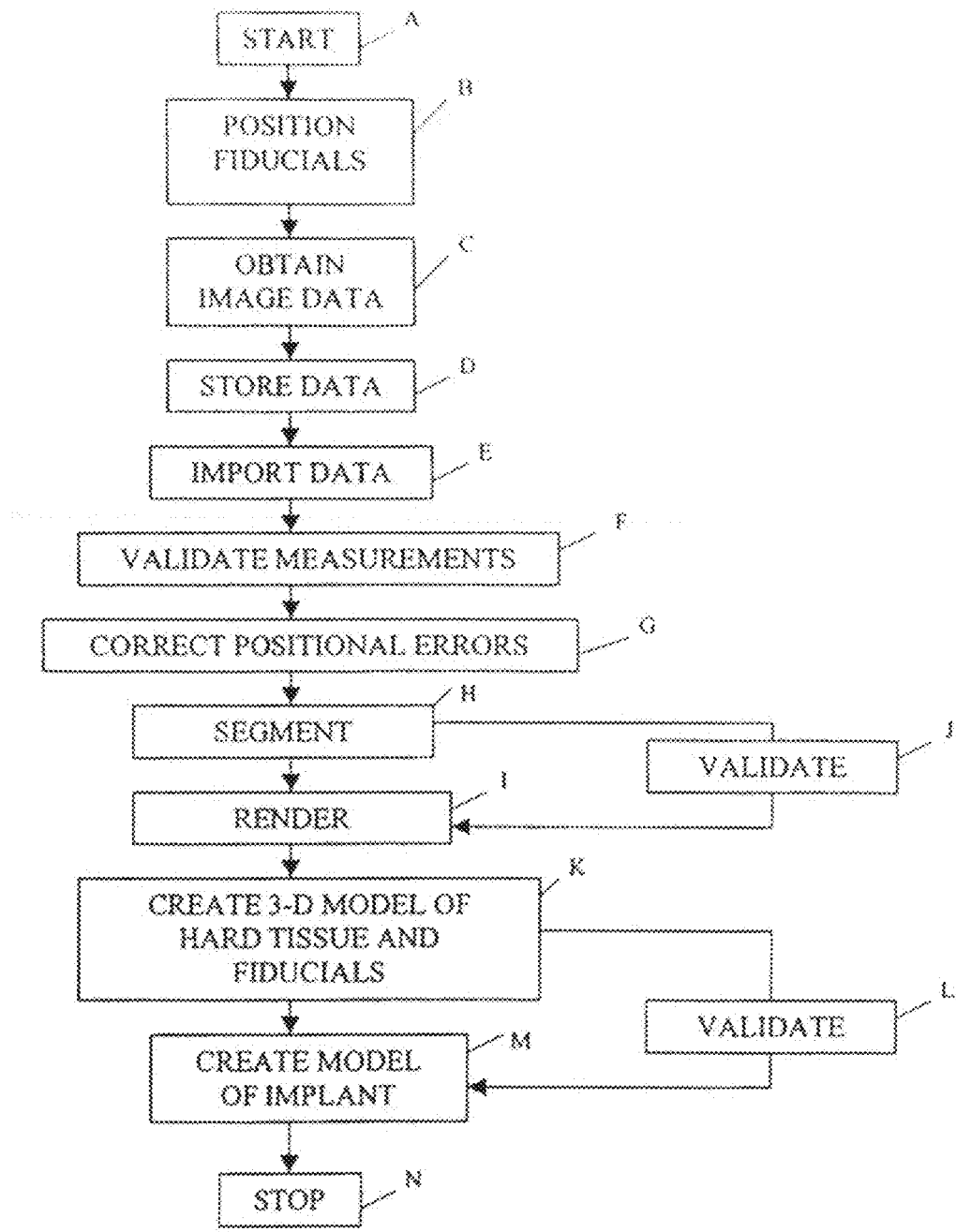
FIG. 47 illustrates a flowchart for creating a three-dimensional model according to the present invention.
Figure 48:
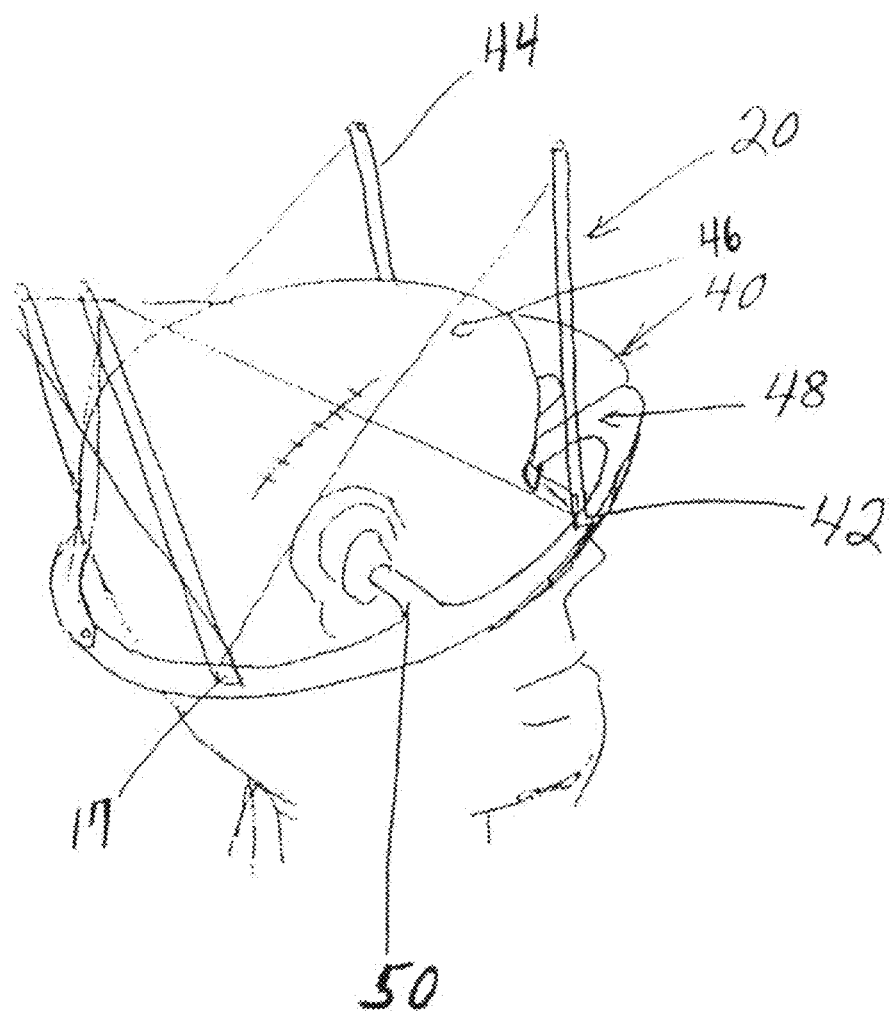
FIG. 48 illustrates a frame to which fiducials are attached according to the present invention.

With reference to FIGS. 45-47, a method for creating a 3-dimensional model 10 of a hard tissue of interest 12, which is included within a subject 14, and a plurality of fiducials 16a, 16b, 16c begins in a step A. The hard tissue of interest 12 may include bony structure (e.g., a skull) in the subject 14. The frameless approach to creating fiduciary distances is to position fiducial markers 16, in a step B, in a fixed relationship to the subject 14. In the preferred embodiment (i.e., a frameless technique), the fiducials 16 are spherical markers (e.g., about 1.5 mm thick and including a lead material) placed (adhesed) around a defect 32 on the subject 14. In the preferred embodiment, three (3) fiducials 16 are used. However, additional fiducials may be used, especially if there is any concern that muscles of the subject's 14 facial expression might twitch the marker site daring a scan. Alternatively, with reference to FIG. 48, which will be discussed in more detail below, fiducials 17 are included as markers secured to a frame 20 that is placed around the hard tissue of interest 12. In either embodiment, it is to be understood that the fiducials, 16, 17 have a density that is high enough to create an identifiable spot in an image volume. Once the fiducials 16, 17 are positioned, precise measurements of the distances between the markers is recorded using, for example, calipers.

With reference again to FIGS. 45-47, a processing system 18 obtains and processes data for producing images of the subject 14 and an implant, which will be discussed below. Data, which represents a volume (3-dimensional) image of the fiducials 16 and the hard tissue of interest 12, is obtained during a scan in a step C. Because the image data represents a 3-dimensional image, it may be referred to as voxel data. Preferably, the step C of obtaining the image data includes imaging the subject 14, which is positioned on a table 22 in a gantry 24, using a computerized-tomography (CT) scanner according to a particular protocol. The table 22 and gantry 24 are controlled by the processing system 18. In the preferred embodiment, selected parameters of the protocol include: a 1.5 mm slice thickness with a 1.5 mm table increment, 256 mm field-of-view; gantry tilt of zero (0) degrees; and kVp and mAs settings chosen by a trained technician to highlight hard tissue (e.g., bone) details in the subject 14. Other aspects of the scan are also part of the preferred protocol. The CT data is typically about 512×512 by 100 slices at 12-bit resolution and represents about 50 MBytes of data. It is important to realize that subject movement during the step C (i.e., during the imaging process), may cause positional errors between the fiducials 16 in the image data. Therefore, if a subject is restless or likely to fidget (e.g., if the subject is a your child or unable to hold sufficiently still), twilight sleep (e.g., light sedation), or if necessary general anesthetic, may be used.

Once the image data (e.g., the CT image data) is captured in the step C, it is stored on a transportable medium in a step D. Alternatively, the image data are also transferred over a network where physically possible and security concerns allow. Then, the image data is imported, in a step E, into a computerized 3-dimensional segmentation process, which occurs here in the AUTO program. More details of the AUTO program will be discussed in more detail below. It is to be understood that the image data is typically converted into a form that is compatible with the AUTO program.

Respective measurements between the fiducials 16, or on an imaging frame, in the fixed relationship to the subject 18 and in the image data are validated (confirmed) in a step F. More specifically, comparisons of respective distances are made between the markers 16 in the fixed relationship to the subject 18 and in the image data to insure that the segmentation exercise has not introduced any inaccuracies in the image data that proceeds to the next step. The comparisons made during the step F may indicate that positional errors are present in the image data (e.g., if the distances between the fiducials 16 in the image data do not correspond to the distances between the fiducials 16 around the subject 14). If such inaccuracies are present in the image data, mathematical operations are performed, in a step G, for correcting the positional errors.

The tissue, in this example the bony skull, of interest 12 and the fiducials 16 are segmented (identified) from the image data in a step H. More specifically, an operator uses the AUTO program to segment the hard tissue of interest 12 (bony structure) of the subject 14 and the fiducials 16 away from the non-hard tissue material (non-bony structure). An operator of the system 18 manually marks (identifies) (e.g., with a pointing device such as a mouse) pixels within the image data that represent the hard tissue 12, fiducials 16, and/or frame 20. In, for example, the image shown in FIG. 45, only pixels included in the skull 12 are marked while the pixels included in interior sinus surfaces, the cranial base, zygoma, etc. are unmarked.

The operator may use a 3-D region-growing algorithm to segment the bony objects in the volume and to label the fiducial markers 16. The operator reviews the segmentation results slice-by-slice. If needed, the operator uses 2-D region growing algorithms and manual methods to add or remove regions from the 3-D automatic segmentation. The operator adds bridges to connect the segmented fiducial markers to the segmented skull. Initially, the region-growing algorithms will be based on voxel intensity. A later algorithm will use the zero-crossing of the second derivative of voxel intensity. Initially, the segmentation will be voxel-by-voxel. Since the resolution of the CT data is artificially increased, this simulates sub-pixel segmentation. Later methods will use vectors to describe the segmented region boundaries. These later methods will permit sub-pixel segmentation without artificially increasing the resolution.

The AUTO program includes additional operations that apply to the entire image volume:

NEGATE VOLUME: Reverses the data values for all voxels. If $v_{xyz}$ is the internal representation of a voxel value, the new voxel value is ($254-v_{xyz}$), where grayscale is encoded from 0-255 (other grayscale ranges would work equally well).

MIRROR VOLUME: Reverses the order of the voxels in the x-dimension. Normally, the x-dimension is aligned with the subjects left-right axis. If so, this is the same as a left-to-right reversal of the volume. If the x-dimension corresponds to some other patient axis, this is the same as a left-to-right reversal and volume rotation.

UNMARK MASK LAYER: Convert marked voxels (i.e., those with data value 255) to data value 254.

SWAP BACKUP: Exchanges the working copy of the volume with the backup copy.

RESTORE BACKUP: Replaces the working copy of the volume with the backup copy.

ASSIGN TO BACKUP: Replaces the backup copy of the volume with the working copy.

ETCH VOLUME Sets all unmarked voxels (i.e. those with data values other than 255) to data value 0. The resultant volume consists only of the marked voxels.

NON-ETCH VOLUME: Sets all marked voxels (i.e. those with data value 255) to data value 0. In essence, this removes the marked voxels from the volume.

AVERAGE VOLUME: Performs a linear smoothing operation on the voxel data values in each slice of the volume. The kernel size varies from "3" to "15" The kernel is three-dimensional and all components of the filter have equal weighting. For example, if the kernel size is 5, the kernel is a 5×5×5 matrix and each component has a value of $0.008(=1/125)$. It is not known if such a filter compensates for non-isotropic volumes.

SMOOTH VOLUME: Performs a non-linear smoothing operation on the voxel data values m each slice of the volume. The nonlinear smoothing operation appears to be the median value of the voxels considered, but it may be a morphological operation. The behavior of this operation does not appear to be affected by the setting of the Kernel Size slider.

EQUALIZE VOLUME: By itself, this has no noticeable effect on the volume data. This is used in conjunction with Normalize Volume.

NORMALIZE VOLUME: Performs a histogram equalization of the voxel values. If EQUALIZE VOLUME has been executed prior to this operation, the background voxels are ignored, producing a visually more pleasing result.

ALIGN SLICES. This operation does not produce any observable results. This may be a disabled or abandoned feature or it may be a placeholder for a future volume operation.

Although the AUTO program is predominately run in a "manual mode," the program includes several algorithmic techniques for speeding the segmentation process (e.g., volume editing). Volume editing may include volumetric region growing, volume ROI and volume non-ROI, and replanarization:

VOLUMETRIC REGION GROWING: After selecting a voxel from an image in the work window, the AUTO program can find all connected voxels with similar data values. The algorithm looks not only within the image in the work window, but through the entire volume. A GROWTH FACTOR slider is available to control the meaning of "similar." All selected voxels are marked (i.e. their data value is set to 255).

VOLUME ROI and VOLUME NON-ROI: It is expected that this should apply an image editing operation (such as mark, erase, boost, et cetera) across the full volume, but these controls do not have any visible effect. These functions may be disabled or the rules for using these may not be understood yet.

REPLANARIZATION: The AUTO program can produce planar images orthogonal to any of the orthogonal MPR views along arbitrary cuts. The range of angles supported is restricted. Currently, no 3-axis oblique cuts are permitted, but are envisioned. Only one planar image is produced.

The AUTO program includes any options for an operator to display and manipulate an image:

Look-Up Tables

A plurality of Look-up Tables (LUTs) are used to map the image data values to the colors displayed on the screen. A Normal LUT maps ascending data values to grayscale values from black to white; a Pseudo LUT maps ascending data values to a color ramp that varies smoothly from black to rose to blue, to violet to green to yellow to cyan to white. Reversed versions of both of these LUTs are available.

MPR Views

The volume data is presented in three orthogonal views, commonly called an orthogonal Multi-Planar Reconstruction (MPR). The X-Y plane presents the individual slices from the volume. The Y-Z and X-Z planes show orthogonal planes perpendicular to the X-Y plane and aligned with the image matrix axes. The Y-Z and X-Z planes are sealed according to the value of the slice-per-pixel ratio. Linear interpolation is used to expand the orthogonal views if the volume is non-isotropic.

The operator can scroll or loop through the volume in any of the MPR views. The operator may also automatically scroll through the volume in any of the MPR views. The operator may select the range of slices (or cross-sections) covered by the scrolling operations.

The operator may get a quick, reduced resolution view of all of the slices in the volume. The slices are shown starting with the first slice of the scroll range.

Any image in any one of the MPR views may be "ported" to the image work window for editing.

Working View

The working view, also referred to as the work window, is where all image editing operations are performed. The work window has controls for:

Enlarging or decreasing the size of the image in the work window. There are constraints on the maximum and minimum sizes.

The overall brightness of the image may be raised or lowered.

Changing the view to the next or previous image in the volume.

Planar region growing.

Committing the changes made to the image in the work window. This replaces the slice in the volume with the edited version in the work window.

Restoring slice image. This replaces the image in the work window with the image from the work volume. This undoes any edits made since porting the image to the work window.

Histogram View

The histogram view shows both a cumulative histogram and a binning histogram of the image in the work window. The cumulative histogram shows a plot of the percentage of pixels at a given pixel value or lower. The binning histogram shows a plot of the pixels at a given pixel value.

The operator may select the pixel data value range depicted by the histogram plots. When adjusting the range, the image in the work window is modified to show only the pixels in that range. Pixels with data values below the selected range are displayed as a first color and pixels with data values above the selected range are displayed as a second color.

Image Operations

These operations pertain to the image slice in the image work window.

EQUALIZE SLICE: By itself, this has no noticeable effect on the pixel data. This is used in conjunction with Normalize Slice.

NORMALIZE SLICE: Performs a histogram equalization of the pixel values. If EQUALIZE SLICES has been executed prior to this operation, the background pixels are ignored, producing a visually more pleasing result.

Image Editing

PLANAR REGION GROWING: After selecting a pixel of an image in the work window, the AUTO program c in find all connected pixels with similar data values. A GROWTH FACTOR slider is available to control the meaning of "similar." All selected pixels are marked (i.e. their data value is set to 255).

ROI EDITING: The operator may define a rectangular or irregularly-shaped Region Of Interest (ROI). The operator may apply one of five editing operations to the pixels contained with the ROI. The editing operations are Mark (set value to 255), Erase (set value to 0), RubOut (restore pixel value), Backup (restore pixel value from backup volume), and I3oost (increase pixel data value).

BRUSH EDITING: The operator may use a square brush, sued from 1×1 to 5×5 pixels, to "paint" areas of the image. One of five editing operations is applied to the pixels under the brush. The editing operations are Mark (set value to 255), Erase (set value to 0), RubOut (restore pixel value), Backup (restore pixel value from backup volume), and Boost (increase pixel data value).

Isolated points of the hard tissue of interest 12 and the fiducials 16 are rendered as a 3-dimensional surface representation in a step I. The rendering algorithm used in the preferred embodiment creates a manifold surface (e.g., iso-surface) image using triangulation imaging techniques. In an alternate embodiment, ray tracing or volume rendering is also contemplated. Furthermore, it is also contemplated to render other objects along with the surface of interest (e.g., an external surface of the hard tissue of interest 12 and the fiducials 16) to judge the fit of the implant within the defect site. For example, it is important not to excessively press on the brain or protrude the overlying scalp, either may result in failure to heal, pain, and eventual extrusion of the implant. The surface of the segmented voxels are abstracted and converted to a triangular mesh representation. Triangle simplification methods are used to reduce the number of triangles. It is expected that this will produce an anti-aliased, triangulated surface mesh.

To assist the triangulation process, the slice data may be interpolated so as to increase the number of slices by a factor of four (4) or more. Linear interpolation is preferably used because of the convex-hull property. To assist the segmentation process, the slice data may be interpolated so as to increase the pixel resolution by a factor of four (4) or more. A cubic interpolation method, such as B-spline or cubic-spline, is contemplated. In order to reduce the machine requirements, it is contemplated to perform these operations on-the-fly during the segmentation process.

Optionally, the respective measurements between the fiducials 16 in the fixed relationship to the subject 14 and in the surface representation are validated in a step J in order to verify that the surface rendering process has not compromised the image's accuracy. After the surface representation is rendered, the voxel data corresponding to the surface representation is prepared to produce a physical rendering, a hard model, of the defect site and as much surrounding anatomy as is necessary to design the prosthesis. This hard model is produced by a stereolithography (STL) process. As will be described below, the STL process is used for building a physical model of a medical device 30 (e.g., an implant), which fits (i.e., "drops") into a defect 32 of the hard tissue of interest 12. The implant is typically about 100 $cm^2$ and has tapered edges. Manual repair methods suffice for most defects less than half this size, however these methods are optimum for defects this size or larger. The implants have tapered edges to provide unambiguous seating and ease of fixation by microplating or suturing.

Then, a 3-dimensional model 34 of the hard tissue of interest 12 and the fiducials 16 is created in a step K. It is to be understood that the model 34 substantially represents the hard tissue of interest 12, including the defect 32; therefore, the reference numeral 34 has been included in FIG. 45. Optionally, the respective measurements between the fiducials 16 in the fixed relationship to the subject 14 and in the 3-dimensional model are validated in a step L to insure accuracy for the last time of the STL, produced patient model with dimensions taken from the patient prior to imaging. Then, a 3-dimensional model of the medical device 30 (e.g., an implant), which is to be implanted into the subject, is created in a step N. The process stops in a step N. The process of creating the implant 30 is discussed in more detail below.

Once created, the model of the implant 30 is given to a skilled anaplast for preparation of an implant, that may be seated in the subject 14, using an acrylic material, PMMA (polymethylmethacrylate). These methods apply to any material that the surgeon and anaplast agree to use. Currently only bioinert (biocompatible) materials such as silastic, titanium, or PMMA have been considered appropriate, however the correct implant configuration for tissue engineered (i.e., resorbable) implants can be obtained with the same methods. The anaplast feathers the edge of the implant so that it fits unambiguously against the defect 32 in the subject's tissue of interest 12. The thickness of a PMMA implant is typically about six mm thick. The curvature of the implant 30 is designed to conform to the subject's anatomy 12. A good fit is necessary for cranial implants in order to insure protection of the underlying brain from trauma and infection and that the overlying scalp receives a sufficient blood supply. Optionally, the implant 30 and model 34 of the hard tissue of interest 12 are gas sterilized for later use by a surgeon. Sterilization would not be necessary if a sterile production process were used.

The anaplast manually identifies and labels anatomical landmarks. It is expected that later techniques will use computer-assisted landmark labeling. As time permits, the anatomical ridge curves and geodesics are also identified. The SASE program uses landmarks, ridge curves, and geodesics.

To warp a mirrored skull, three-dimensional regions containing the landmarks are constructed to create a mirrored version of the skull. The mirrored version to the original skull shape and matching landmarks are warped (morphed).

This will get the surfaces close to their desired position. The warp is refined to fit the surfaces to each other. As time permits, the ridge curves and geodesics in the skull shape (and its mirror image) are also identified. This information is used to warp (morph) the mirrored skull to the original. This will give a better initial fit. This method, or similar methods, have been implemented in the SASE program.

If the defect spans the midline, standard skull data is warped (morphed) to the subject skull shape and matching landmarks. As time permits, the ridge curves and geodesics are also used in addition to the landmarks. Standard skull data may be used in place of or as a supplement to, mirrored skull data.

An implant shape is defined by finding a defect margin in a skull surface and transferring the defect margin to the warped skull surface. The warped skull surface is pinned down at the defect margin and all points exterior to the defect region. The warped skull surface tangents are also pinned down at the defect margin. An outer surface shape is determined by using the warped skull surface in the defect region to estimate the original patient skull surface. The maximum curvature is reduced while keeping the internal volume constant. If the subject has reduced brain volume and correspondingly less overlaying skin, the defect surface is flattened, thereby reducing the internal volume.

Optionally, an inner, ball-bearing surface that is about 6 mm from the warped outer surface is determined to add thickness treatment.

Edge Seating and taper treatment are applied at the defect margin by trimming the outer surface where the subject's skull falls about 1 mm below the warped outer surface. From this point, a smooth taper is made to the timer, ball-beating surface. The taper is about 1 cm long. Walls are formed at the edges for resulting in the desired implant shape.

During an implantation process, the surgeon first test-fits the implant 30 against the defect 32. If necessary, the surgeon adjusts the dimensions of the implant 30 by grinding away excess material. Tapered edges facilitate these types of adjustments. If desired, the surgeon drills pairs of holes in a middle portion of the implant 30 for a suturing thread. For example, holes in the implant allow placement of sutures through the subject's tissue 12, the suture thread is pulled tight and tied, thus raising dura mater (internally) or the temporalis muscle sleave (externally) to the implant 30, or placement of temporary or permanent drains into the implant site. The implant 30 is secured to the subject's tissue 12 using titanium buttress plates and screws or sutures. Screw holes are optionally predrilled to reduce stress on the tissue 12 (e.g., bone) and the implant.

It is to be understood that the image data is converted to respective file formats at appropriate steps in the method discussed above. For example, image data is converted to a format for the rendering algorithm before the rendering step I. Also, the data representing the surface representation is formatted to the STL, machine, using appropriate software, before the 3-dimensional models are created.

It is to be understood that corrections may be made (e.g., mathematically) to the 3-dimensional surface representation and the 3-dimensional model if it is determined that inaccuracies (image acquisition errors) are included in the measurements between the fiducials after the respective steps. As a general rule, however, the earlier the corrections are made in the process, the less expensive it is to implement. For example, it is less expensive to correct image acquisition errors in the 3-dimensional surface representation than in the 3-dimensional model. Corrections avoid the expense and inconvenience of acquiring a new volume image.

It is contemplated in alternative embodiments to create a computerized model of the implant from the segmentation data created by the AUTO program, thereby eliminating the need to create a physical model of the part of the body where the implant 30 is to be installed. One way in which this may be accomplished is to transmit the data created by the segmentation step H to an algorithm that uses normative sampling data (e.g., from humans) on a particular part of the subject where the implant 30 is to be installed. Such an algorithm best fits or warps the normalized data sampling to the scanned, segmented data from the segmentation algorithm to create a computer model of the implant 30. Then, the implant 30 (or a mold of the implant 30) is created using a 3-dimensional manufacturing tool.

Normative images are used by first gathering appropriate information about the subject (e.g., sex, race, and date of birth). Then, an operator locates appropriate x-ray images. Fiducial pin-holes are placed in a known geometry in the lateral and frontal x-ray images. The operator aligns a reference grid associated with the subject to the fiducial pin-holes in lateral and front views of the image. Landmark registration is performed by causing a mesh of anatomical reference points to be superimposed upon the lateral and frontal x-ray images. More specifically, using a knowledge of the anatomy depicted in the x-ray image, the operator moves the vertices of the mesh to the appropriate anatomical features. Alternatively, automatic landmark detection is available. Furthermore, it is contemplated to use previously stored images and/or permit the current image (or portions thereof) to be stored.

The key aspect of the preferred protocol that enables the development of a precisely aligned implant (i.e., a "drop-in" implant) is the use of the fiducials 16. Note, however, that the invention is not specifically limited to lead fiducials as described here, but also encompasses other techniques of providing a precise reference marker on the subject's image, which can be subsequently used to verify the dimensions of the implant. The imaging of the fiducials and the data representing the geometry of these elements with respect to each other is used by the steps in the method to ensure that the implant has proper dimensions.

With reference again to FIG. 48, the frame 20 provides a defined geometrical reference for three-dimensional Computed Tomography (3D CT) to be used to create verified 3D spatial coordinates. 3D CT is a medical imaging technique that uses x-ray radiation to view cross sectional slices of the subject's 14 anatomy. The slices are assembled to form a 3D representation of the subject's 14 anatomy. To ensure that the digital representation of the subject's 14 anatomy is the correct size, the defined reference frame 20 is established within the imaged field of view. This reference frame 20 requires no relative movement between markers 17. The frame 20 is rigidly attached to the subject 14 so that movement can be detected. Movement of the subject 14 during a scan may result in inaccuracies. The defined reference frame 30 is used to verify anatomical dimensions used for the production of correctly sized implants. Due to the scheduling of the scans, simple pre-scan patient preparation is desired. Post-scan confirmation of the measurements of the reference frame should be easy. The geometrical reference frame 20 is preferably used on the subject's 14 head or face, for use with the design of cranial-facial implants.

The practice of comparing the physical model produced by the STL machine with inter-fiducial distances measured on the subject 14 must be revised accordingly because the new fiducials are not as close to the skull. As discussed below, bridges are created between each fiducial 17 and the hard tissue of interest 12 (skull) so that the inter-fiducial distances may be verified on the model 34 produced by the STL machine. With the use of the fiducials 17 that are further away from the skull 12, pseudo-fiducials are added by the operator during segmentation so that those inter-pseudo-fiducial measurements may be verified on the 3D model 34. After the inter-fiducial distances are verified to be correct, pseudo-fiducials are created and compared throughout the remainder of the model production procedure.

The frame 20 may be assembled using an existing dental facebow 40 (Whip Mix), which may be made of aluminum. Modifications are made to rigidly attach at least four (4) non-coplanar radiographic points 42. The fiducials 17 (e.g., lead spots) (Beckley) or other markers are attached to the points 42. Rigid attachment of the fiducials 17 may present a problem as the width and height of the facebow 40 vanes to accommodate sizing for different subjects A separate assembly can be attached to the facebow 40 that would define fiducials with out reference to the geometry of the facebow 40. Rods 44 and/or cross rods 46 may be attached to the facebow to help detect subject notion.

The facebows 40 are readily available from various dental supply companies. The point markers 42, which are attached to the facebow 40, must not move in relation to each other and, when the scan is taking place, cannot move with respect to the subject 14. The relative location of the markers 42 may vary from subject to subject. Facebows 40 typically attach to, the subject on the nasion 48 (bridge of nose) and external auditory meati 50. A hand tightening screw preferably secures the nasion attachment. By tightening the nasion pad to the nasion, the external auditory meati (external ear holes) pads are pulled forward and secured by pressure.

Figure 49:
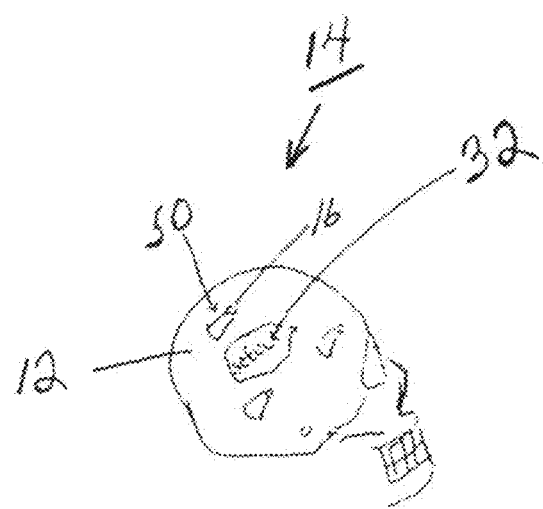
FIG. 49 illustrates a manually constructed budge between the fiducials and the hard tissue of interest added to the image according to the present invention.

Optionally, with reference to FIGS. 47 and 49, in addition to the segmentation step H, the operator marks the position of the fiducials 16 for creating a bridge 50. It is to be understood that FIG. 49 represents an exaggerated depiction of the subject 14 including the hard tissue of interest 12. The bridges 50 represent links or leads between the fiducials 16, which are located on or above the surface of the subject's skin, and the hard tissue of interest 12, which may be located below the surface of the skin.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A computer implemented method of obtaining data for determining a three-dimensional shape of a medical device, the method comprising:
    rendering a computer-generated three-dimensional representation of a target tissue from computer readable image data of the target tissue wherein the target tissue comprises two portions, a portion with a defect and a portion without a defect;
    identifying anatomical landmarks on the computer-generated three-dimensional representation of the target tissue;
    superimposing onto the rendered computer-generated three-dimensional representation of the target tissue a three-dimensional template to span the defective portion;
    deforming the three-dimensional template to match the identified anatomical landmarks to determine the three-dimensional shape of the medical device.

2. The method as set forth in claim 1, wherein the three-dimensional image data is obtained from image slices of the target tissue.

3. The method as set forth in claim 1, wherein the three-dimensional image data is obtained as one or more voxels of the target tissue.

4. The method of claim 1, wherein the medical device is an implant to be implanted in a subject.

5. The method of claim 1, further comprising fabricating the 3-dimensional shape of the medical device.

6. The method of claim 1, wherein deforming the three-dimensional template to match the identified anatomical landmarks to determine the three-dimensional shape of the medical device comprises determining the three-dimensional shape of the medical device based on the deformed template that spans the defective portion.

7. The method of claim 1, wherein the anatomical landmarks are present on an external surface of the non-defective portion.

8. The method of claim 1, further comprising generating the computer-readable image data of the target tissue.

9. The method of claim 8, further comprising fabricating the 3-dimensional shape of the medical device.

* * * * *